US009718668B2

(12) United States Patent
Tung et al.

(10) Patent No.: US 9,718,668 B2
(45) Date of Patent: Aug. 1, 2017

(54) METHOD OF FABRICATING A NANOCHANNEL SYSTEM FOR DNA SEQUENCING AND NANOPARTICLE CHARACTERIZATION

(71) Applicants: Chao-Hung Steve Tung, Fayetteville, AR (US); Jin-Woo Kim, Fayetteville, AR (US); Taylor Busch, Richardson, TX (US)

(72) Inventors: Chao-Hung Steve Tung, Fayetteville, AR (US); Jin-Woo Kim, Fayetteville, AR (US); Taylor Busch, Richardson, TX (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 951 days.

(21) Appl. No.: 13/951,664

(22) Filed: Jul. 26, 2013

(65) Prior Publication Data
US 2014/0231254 A1    Aug. 21, 2014
US 2017/0152134 A9    Jun. 1, 2017

Related U.S. Application Data

(63) Continuation-in-part of application No. 13/768,960, filed on Feb. 15, 2013, now abandoned.
(Continued)

(51) Int. Cl.
*B81B 1/00* (2006.01)
*C12Q 1/68* (2006.01)
(Continued)

(52) U.S. Cl.
CPC ............ *B81B 1/00* (2013.01); *B81C 1/00071* (2013.01); *B81C 3/001* (2013.01); *C03C 15/00* (2013.01);
(Continued)

(58) Field of Classification Search
None
See application file for complete search history.

(56) References Cited

U.S. PATENT DOCUMENTS 6,280,939 B1    8/2001  Allen
2003/0141189 A1  7/2003  Lee et al.
(Continued)

FOREIGN PATENT DOCUMENTS

JP    2002257824 A    9/2002
SG        173398 A1    8/2011
(Continued)

OTHER PUBLICATIONS

Zhiqian Wang; A Nanochannel System Fabricated by MEMS Microbabrication and Atomic Force Microscopy; Feb. 20, 2011; 5 pages.*
(Continued)

*Primary Examiner* — Linda L Gray
(74) *Attorney, Agent, or Firm* — Richard Blakely Glasgow

(57) ABSTRACT

A process for fabricating a nanochannel system using a combination of microelectromechanical system (MEMS) microfabrication techniques, atomic force microscopy (AFM) nanolithography, and focused ion beam (FIB). The nanochannel system, fabricated on either a glass or silicon substrate, has channel heights and widths on the order of single to tens of nanometers. The channel length is in the micrometer range. The nanochannel system is equipped with embedded micro and nanoscale electrodes, positioned along the length of the nanochannel for electron tunneling based characterization of nanoscale particles in the channel. Anodic bonding is used to cap off the nanochannel with a cover chip.

20 Claims, 39 Drawing Sheets

Related U.S. Application Data

(60) Provisional application No. 61/633,712, filed on Feb. 16, 2012.

(51) Int. Cl.

| | | |
|---|---|---|
| *C03C 27/06* | (2006.01) | |
| *G01N 33/487* | (2006.01) | |
| *B32B 38/04* | (2006.01) | |
| *B81C 1/00* | (2006.01) | |
| *C03C 15/00* | (2006.01) | |
| *C03C 17/00* | (2006.01) | |
| *C03C 27/00* | (2006.01) | |
| *B81C 3/00* | (2006.01) | |
| *B82Y 15/00* | (2011.01) | |
| *B82Y 40/00* | (2011.01) | |

(52) U.S. Cl.
CPC ............ *C03C 17/001* (2013.01); *C03C 27/00* (2013.01); *C03C 27/06* (2013.01); *C12Q 1/6869* (2013.01); *G01N 33/48721* (2013.01); *B82Y 15/00* (2013.01); *B82Y 40/00* (2013.01); *Y10S 977/924* (2013.01); *Y10T 156/1056* (2015.01); *Y10T 156/1064* (2015.01); *Y10T 156/1074* (2015.01); *Y10T 156/1082* (2015.01); *Y10T 156/1309* (2015.01)

(56) References Cited

U.S. PATENT DOCUMENTS

| | | |
|---|---|---|
| 2004/0219596 A1 | 11/2004 | Sundararajan et al. |
| 2007/0082352 A1 | 4/2007 | Cumpson |
| 2008/0213923 A1 | 9/2008 | Boland et al. |
| 2009/0227040 A1 | 9/2009 | Sahin et al. |
| 2009/0305273 A1 | 12/2009 | Cao et al. |
| 2010/0120023 A1 | 5/2010 | Sahin et al. |
| 2011/0053805 A1 | 3/2011 | Riedo et al. |
| 2011/0168562 A1 | 7/2011 | Nuckolls et al. |
| 2011/0177498 A1 | 7/2011 | Clarke et al. |
| 2011/0236984 A1 | 9/2011 | Sun et al. |

FOREIGN PATENT DOCUMENTS

| | | |
|---|---|---|
| TW | 200907068 A | 2/2009 |
| WO | 2008132643 A1 | 11/2008 |
| WO | 2010062903 A2 | 6/2010 |
| WO | 2011047582 A1 | 4/2011 |
| WO | 2011136527 A2 | 11/2011 |
| WO | 2011142614 A2 | 11/2011 |
| WO | 2011143340 A2 | 11/2011 |

OTHER PUBLICATIONS

Taylor Busch, Design and Fabrication of Nanofluidic Systems with Integrated Sensing Electrodes for Rapid Biomolecule Characterization, Thesis, May 2013, University of Arkansas.

Shahid Qamar, et al., Can an Atomic Force Microscope Sequence DNA Using a Nanopore?, Biophys. Journal, 94 (4), p. 1233-1240 (Feb. 15, 2008).

Nathaniel L. Rosi and Chad A. Mirkin, Nanostructures in Biodiagnostics, Chem. Rev. 2005, 105, p. 1547-1562 (2005).

Karolyn M. Hansen, et al., Cantilever-Based Optical Deflection Assay for Discrimination of DNA Single-Nucleotide Mismatches, Anal. Chem. 2001, 73, p. 1567-1571.

J. M. Kim, et al., Simultaneous Topographic and Fluorescence Imaging of Single DNA Molecules for DNA Analysis with a Scanning Near-Field Optical/Atomic Force Microscope, Anal. Chem. 2001, 73, p. 5984-5991.

Vinod Kumar Khanna, Existing and emerging detection technologies for DNA (Deoxyribonucleic Acid) finger printing, sequencing, bio- and analytical chips: A multidisciplinary development unifying molecular biology, chemical and electronics engineering, Biotechnology Advances 25 (2007), p. 85-98.

Larry J. Kricka, et al., Miniaturized detection technology in molecular diagnostics, Expert Review of Molecular Diagnostics (2005), 5(4), p. 549-559.

Michael D. Garrison, et al., Scanning Probe Microscopy for the Characterization of Biomaterials and Biological Interactions, Annals of the New York Academy of Sciences 831, p. 101-113, (Dec. 1997).

Anne-Sophie Duwez, Molecular cranes swing into action, Nature Nanotechnology, 3, p. 188-189 (2008).

Wen-Hsin Han, et al., Enhanced Recognition of Single-Base Mismatch Using Locked Nucleic Acid-Integrated Hairpin DNA Probes Revealed by Atomic Force Microscopy Nanolithography, Anal. Chem. 2010, 82, p. 2395-2400 (2010).

Ozge Akbulut, et al., Application of Supramolecular Nanostamping to the Replication of DNA Nanoarrays, Nano Letters, 7(11), p. 3493-3498 (2007).

Hong Min, et al., Research Progress in Application of Nanomaterials for Deoxyribonucleic Acid Detection, Chinese Journal of Analytical Chemistry, 39(1), p. 146-154 (2011).

Kato, Z., et al., Nanopatterning on aluminum surfaces with AFM probe, Surface and Coatings Technology, 169-170, p. 195-198 (2003).

Rosa, J.C., et al., Direct patterning of surface quantum wells with an atomic force microscope, Applied Physics Letters, vol. 73, No. 18, p. 2684-2686 (Nov. 2, 1998).

\* cited by examiner

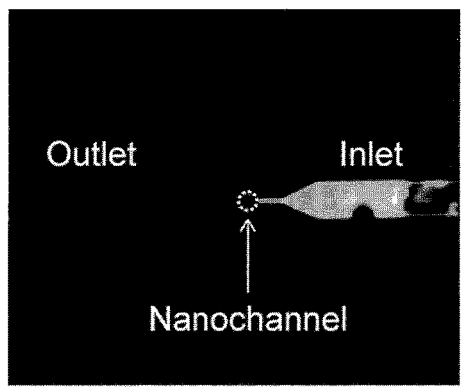
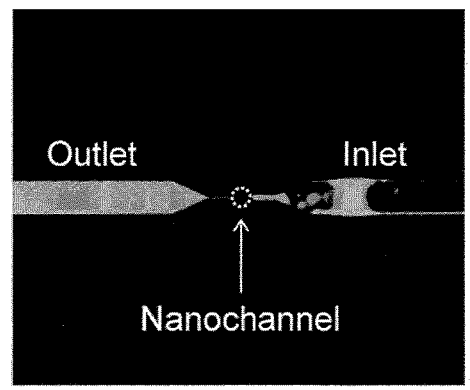
Figure 7(a)  Figure 7(b)
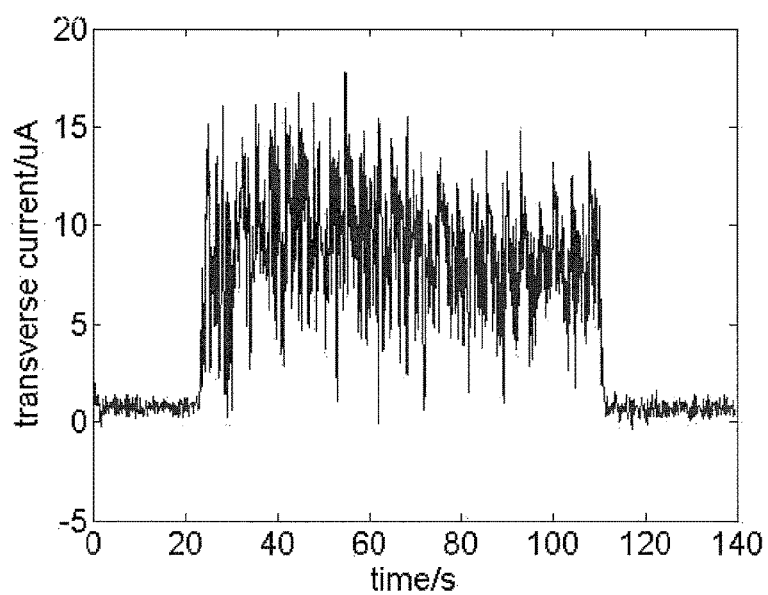
Figure 8

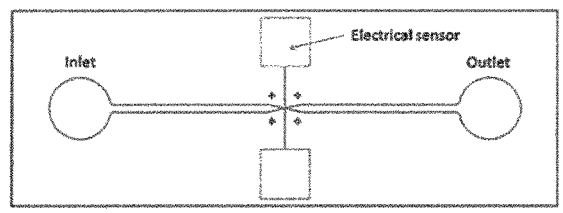
Figure 40(a)
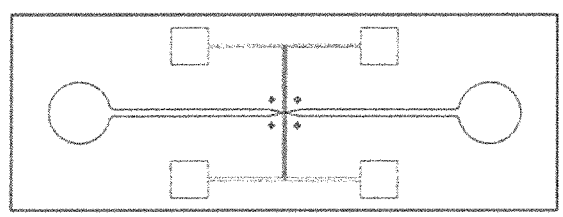
Figure 40(b)
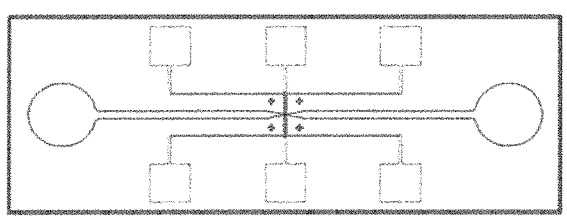
Figure 40(c)
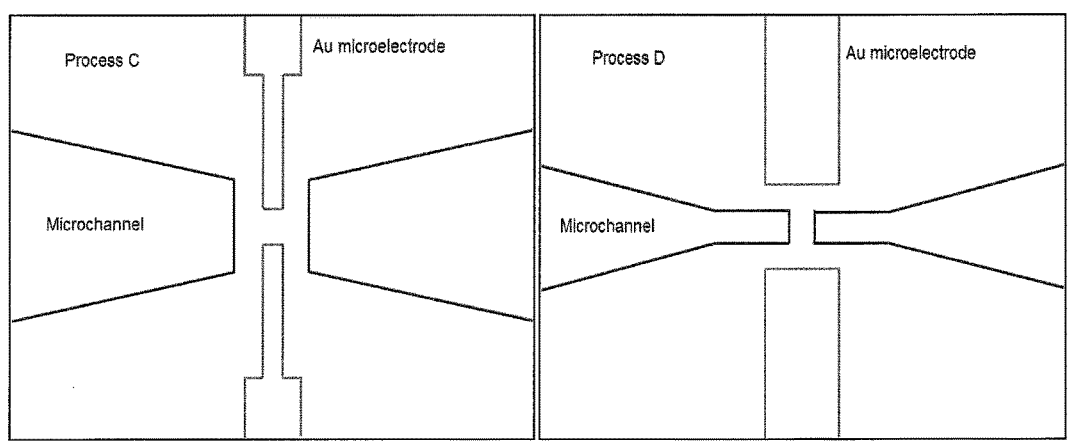
Figure 41(a)                    Figure 41(b)

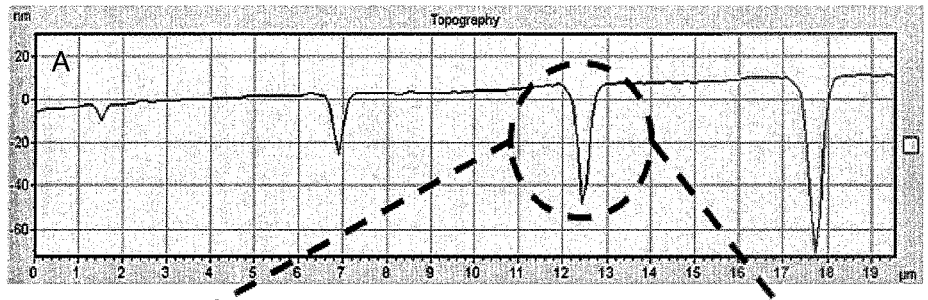
Figure 45(a)
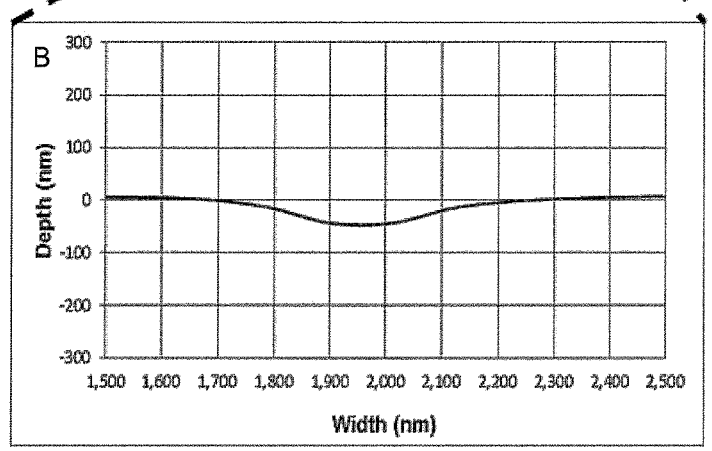
Figure 45(b)
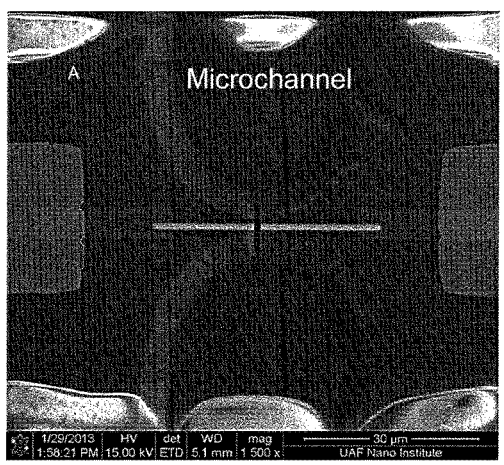
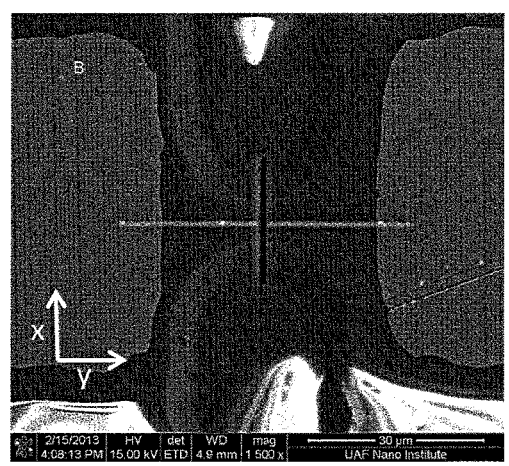
Figure 46(a)　　　　　　　　Figure 46(b)

ated the

METHOD OF FABRICATING A NANOCHANNEL SYSTEM FOR DNA SEQUENCING AND NANOPARTICLE CHARACTERIZATION

CROSS-REFERENCE TO RELATED APPLICATIONS

This application is a continuation-in-part application of, and claims the benefit of, U.S. application Ser. No. 13/768,960, entitled "Method of Fabricating a Nanochannel System for DNA Sequencing and Nanoparticle Characterization" and filed on Feb. 15, 2013. The complete disclosure of said patent application is hereby incorporated by reference. U.S. application Ser. No. 13/768,960 claims the benefit of U.S. Provisional Application No. 61/633,712, entitled "Method of Fabricating a Nanochannel System for DNA Sequencing and Nanoparticle Characterization" and filed on Feb. 16, 2012.

STATEMENT REGARDING FEDERALLY SPONSORED RESEARCH OR DEVELOPMENT

This invention was made with Government support under ECCS-1137948 awarded by the ECCS division of the National Science Foundation. The Government has certain rights in the invention.

BACKGROUND OF THE INVENTION

1. Field of the Invention

The present invention relates to a nanochannel system including a nanofluidic device for rapid DNA sequencing with single-base resolution and single nanoparticle characterization based on electron tunneling, and in particular, to a method of fabrication of such a nanochannel by means of the combination of microelectromechanical system (MEMS) microfabrication techniques, atomic force microscopy (AFM) nanolithography, and focused ion beam (FIB).

2. Description of Related Art

Microfluidic devices have become more accepted as a method for rapid biomolecule detection, analysis, and characterization. With an increasing interest in nanotechnology and its many applications, nanofluidic devices are a new area of focus for both academic research and industry. Nanofluidics is often defined as the study and application of fluid flow in and around nanoscale objects [1]. Such devices are currently being investigated in hopes of revolutionizing the conventional method to sequence the entire human genome. Deoxyribonucleic acid (DNA) contains the genetic code of all living organisms, and it is apparent that obtaining its code rapidly and inexpensively would generate a plethora of benefits to our society. Advancements in DNA sequencing methodologies could potentially revolutionize medical research and provide new avenues of exploration for genetics, bioinformatics, molecular biology, biotechnology, and other relative fields.

Ever since the Human Genome Project was launched in October of 1990, there have been drastic improvements in human genome sequencing research and development [2]. In January of 2008, the 1000 Genomes Project was launched as an international research effort to learn more about DNA sequencing and disease detection and to successfully sequence over 1000 human genomes. By October of 2012, 1,092 human genomes were sequenced around the world, including the US, China, Japan, Kenya, Finland, and Peru [3]. Although this project successfully demonstrated the capability of sequencing over 1,000 human genomes and provided researchers with disease detection information, it did not advance the DNA sequencing process any further. This project cost about $120M, meaning that each genome cost approximately $109K and took about 42 hours [4]. Meanwhile, extensive research has been conducted in order to make human genome sequencing more affordable and faster. The current push is for a rapid, label free method that can sequence the entire genome within a few hours at a cost less than $1,000 [5]. According to the National Human Genome Research Institute, the current state of the art allows the entire human genome to be sequenced for approximately $8K and takes anywhere from 10 hours to 2 days. These costs can be misleading, however. For instance, they do not take into account the equipment costs that fall between $400-500K, the facility costs, the interpretation program cost, and other additional sequencing costs [6, 7]. Tremendous progress (≈$10M to $10K per human genome) has been made in the last decade, but in order to make human genome sequencing a routine medical procedure, prices and sampling times must continue to decline to around $1,000 and less than 2 hours.

If the cost-to-sequencing continues to reduce in this manner, then human genome sequencing may become the new standard in healthcare. For instance, healthcare professionals would have access to the entire genome sequence of their patients and, for the first time, would have the possibility to provide medications based on their patients' individual genetic makeup. Individual analyses of the human genome can be used to predict future diseases and help minimize the consequences associated with them. In order for this type of industry to exist commercially, there are still some improvements that need to be made.

Nanopore Sequencing: One of the groundbreaking approaches for solid-state based rapid genome sequencing is the nanopore method. In this label-free approach, single stranded DNAs are translocated through a nanoscale opening as a result of an external electric field [8]. Individual nucleotides are sensed due to their ability to block the monitored current through the nanopore [9]. In nature, DNA is composed of four different bases: adenine (A), cytosine (C), guanine (G), and thymine (T). Theoretically, the four different bases will block a different amount of current and, therefore sequencing is possible.

The central problem with this approach is the high translocation speed of the DNAs, resulting in a difficulty to achieve single-base resolution. Typical translocation speeds have been recorded between 0.5-30 mm/s and as high as 5 cm/s, which is too quick for high-resolution signal sampling [10-13]. One possible solution to the high translocation speeds is to induce a magnetic field that opposes the electric field, resulting in a more accurate readout [14]. Other approaches have included increasing the fluid viscosity, DNA trapping, and voltage regulation [12, 15-17]. Another possible solution is to pull the DNAs through a nanochannel that is at least 3 orders of magnitude longer than a nanopore. A nanochannel is essentially an elongated nanopore, which fundamentally embodies a larger drag force that can ultimately slow down the DNA translocation. In addition, recent publications suggest that a nanochannel with embedded electrical sensors can detect single DNA bases and eventually sequence the human genome [18]. Such devices will use tunneling current as opposed to blockage current as the sensing mechanism. Nanochannels provide several benefits for biomolecule characterization, but they can be challenging to fabricate.

Nanochannel Techniques: Nanochannels are defined as fluid conduits with at least one minimum dimension from <1 nm to 1000 nm [19]. Typical nanochannels are classified as either 1D or 2D, depending on how many dimensions of the channel fall within nanoscale range. Previously, nanochannels have been fabricated through several different methods, such as bulk nanomachining, surface nanomachining, nanoimprint lithography, and direct nanolithography [9, 20, 21]. The bulk nanomachining process creates features out of the body or bulk of a wafer. Trenches are often created by selective patterning and vertical ion plasma etching. These trenches are sealed by a conformal deposited film to create subsurface or buried channels [22]. Scanning electron microscope (SEM) images of bulk machining and nanoimprinting nanochannels are shown in references 23 and 24 cited herein. [23, 24]. Surface nanomachining differs from bulk mainly due to the fact that surface machined nanochannels are created from the removal of a sacrificial layer. This method does not require the bulk wafer to be etched away. Instead, the nanochannel is located on the surface of the wafer. Nanoimprinted nanochannels are formed by a stamping procedure where a mold with nanoscale features is pressed against a wafer covered with photoresist (PR). When the mold is released from the wafer, the nanoscale pattern is left behind on the PR. The nanoscale features located on a nanoimprinting mold are patterned by direct nanolithographic techniques. Examples of direct nanolithography include electron beam direct-write and focused ion beam milling. Bulk and surface nanomachining can consistently produce 1D nanochannels, where the depth is normally the nanoscale dimension. Nanoimprint and direct nanolithography is known for being able to produce 2D nanochannels with well-defined channel walls [25]. Although these methods of nanochannel formation are viable, they require special tools and processes that are not widely available and/or they have negative drawbacks. One major drawback is the ability to align nanoscale electrodes along the nanochannel for sensing capabilities. The importance of having aligned nanoelectrodes along the nanochannel is discussed below. Previous research has demonstrated that an atomic force microscope (AFM) can be operated to successfully realize 2D nanochannels in silicon substrates [26, 27].

Atomic Force Microscopy: Atomic force microscopy (AFM) is typically used as an atomic scale surface profilometer and is a widely known machine in nanotechnology. Other tools, such as a scanning tunneling microscope (STM), scanning electron microscope (SEM) or a dektak surface profilometer are widely used for surface imaging in addition to an AFM. Unlike a SEM, where topographical images are generated by low angle surface imaging, an AFM generates topographical images based on data points obtained by physical vertical displacement of the tip and cantilever. An AFM is mainly composed of a silicon cantilever with a sharp tip fixed to the end. The tip is used to scan the topography of a surface, such as glass, ceramic, or biological samples. When the tip interacts with the surface, the cantilever deflects. This deflection is detected by a laser and photodiode configuration. The sample rests on a piezo scanner that contains a piezoelectric tube that can move the sample in the vertical direction and maintain a constant force on the sample. The data obtained by the cantilever deflection and photodiode is transferred into a high resolution image of the sample. There are several modes under which the AFM can operate. The four most common modes are contact, non-contact, dynamic mode, and force modulation mode. The most widely used mode in this research was contact mode for AFM nanolithography.

AFM Nanolithography: The manipulation of an AFM probe to scratch, indent, or remove a desired portion away from the surface of a substrate is known as AFM nanolithography. In general, AFM nanolithography can be categorized into two groups: bias-assisted AFM nanolithography and force-assisted AFM nanolithography. In the bias-assisted technique, the AFM tip is biased to create a localized electric field and acts as a nanoscale electrode for current injection or collection. Patterns can be formed as a result of electrostatic, electrochemical, field emission, and explosive gas discharge processes [28]. Force-assisted techniques were used in this research for 2D nanochannel realization. This method of AFM nanolithography has been studied and characterized by previous research under the guidance of Dr. Steve Tung [29]. This method consists of operating the tip in contact mode with an applied load on the sample surface. The tip is used to mechanically cut or scratch away the sample's surface to a desired pattern or nanochannel. The tip is pressed into the normal direction of the sample's surface area and moved in a straight line across the sample. Several parameters can be controlled during this process, including the force setpoint, tip speed, scratch direction, and number of cuts. AFM nanolithography was explored in the present research for nanochannel formation. The details of AFM nanolithography techniques used and correlation experiments completed in this work is discussed below.

Focused Ion Beam: In addition to AFM nanolithography, a focused ion beam (FIB) can also be used for nanochannel formation. An FIB is a nanotechnology tool that is normally coupled with a SEM for imaging purposes. A SEM is a microscope that uses electrons as opposed to light to produce high resolution images. Due to its multiple applications and nanoscale capabilities, the FIB is one of the most cutting edge pieces of equipment for nanotechnology research, with modern day resolution limits around 5-10 nm [30]. The major uses for the FIB are milling, deposition, implantation, and imaging. While the electron gun is used for surface imaging, the ion gun is the main source of making surface alterations since ions are much more massive than electrons. Gallium (Ga) is the most common ion used for FIB due to its high atomic weight of 69.723 g/mol and relatively small atomic radius of 1.35 Å [31]. Most ion beams use a liquid-metal ion source (LMIS) that are heated and accelerated downward to the sample under high electric field somewhere on the order of $10^8$ V/cm while being held under a constant chamber pressure around $10^{-7}$ mbar. As a result of the electric field, the ions travel through the column components and are focused through the tip of the tungsten needle, known as the Taylor cone. The ions are funneled through this approximately 2 nm wide cone and bombarded towards the surface with any energy between 1-50 keV and a current between 1 pA-10 nA. The FIB column is normal to the sample surface. For ion milling or sputtering, Ga+ ions are accelerated towards the sample surface. During the sputtering process, secondary ions (+ or −) are removed from the surface as the beam of ions is raster scanned across the surface with a 11.5 nm pitch and 1 µs dwell time. Moreover, the incident ion beam produces secondary electrons. These secondary ions and electrons are detected and their signal produces the image of the sample's surface [32]. Thus, the FIB is a reliable and valid source of nanochannel formation in addition to AFM nanolithography.

In addition to FIB milling, nanoscale metal deposition is becoming increasingly significant in the field of nanotechnology. By using the same experimental setup as demonstrated in FIG. 6, metals can be deposited on the sample surface with nanoscale accuracy via FIB chemical vapor deposition [33]. The two most common metals commercially available for FIB maskless deposition are platinum (Pt) and tungsten (W). First, the gas injector must be initiated and brought within a few hundred micrometers of the sample surface. The desired gas is injected and absorbed onto the sample surface. Then, the Ga+ ions are accelerated into the surface and break the chemical bonds on the surface of the deposited gas. Dissociated molecules from this volatile reaction are desorbed from the surface and removed by vacuum, leaving behind the desired metal on the surface. It is notable to point out that the deposited metal is not 100% pure, mainly due to the fact that some Ga+ ions are implanted into the surface [32].

Potential Applications of Integrated Nanofluidic Systems: The FIB can be extremely beneficial for nanofluidic device fabrication. For rapid biomolecule detection, such as DNA nucleotides and avian influenza viruses (AIV), there must be a sensor embedded on the device so electrical measurements can serve as the detection element [34]. Due to the nanoscale resolution and capabilities of the FIB, making metal nanosensors is a definite possibility. For instance, biomolecules can be passed through a nanochannel surrounded by nanoelectrodes that serve as the sensing mechanism for the device. By combining nanoelectrodes with a transverse nanochannel, the biomolecules can be translocated through the nanofluidic system and sensed by the electrical sensors. Since some biomolecules, such as DNA, are negatively charged in nature, they can be suspended in a conductive carrying solution and driven through a nanochannel by applying an electric field across the channel. Meanwhile, the current signal across the nanoelectrodes can be monitored in real time as denoted by the double-headed red arrow in FIG. 7. This current that is measured is denoted as the tunneling current, for this is the current that flows across the backbone of each individual biomolecule. For DNA, each nucleotide (A, T, C, and G) has a unique electronic structure, the tunneling current will be different for each base and this can serve as the sequencing mechanism of the device. Previous experiments and theoretical calculations have been conducted to demonstrate that all four nucleobases exhibit unique electrical signatures [35, 36]. Scanning tunneling microscopy (STM) was used in references 35 and 36 cited herein to demonstrate the DNA nucleobase tunneling phenomenon and was validated by mathematical calculations using Green's function.

One potential drawback of a solid state device is the adjacent spacing of the nanoelectrodes. Since the internucleotide spacing is only 0.34 nm for single stranded DNA (ssDNA), the nanoelectrodes must be fabricated on the sub-nanometer scale in order achieve single nucleotide detection [37]. However, surface chemistry techniques can be used to possibly functionalize electrodes and resolve the sub-nanometer electrode spacing problem. Today, there is a heavy international research effort to revolutionize current DNA sequencing methods by discovering a rapid, inexpensive, label-free method.

BRIEF SUMMARY OF THE INVENTION

The present invention is directed to a process for fabricating a nanochannel system. In one embodiment, the process includes (1) a micropatterning step to form at least one electrode on a substrate, (2) a micropatterning step to form a microchannel having inlet and outlet portions on the substrate, (3) an AFM nanolithography step to form a nanochannel connecting the inlet and outlet portions of the microchannel and to dissect the electrode, and (4) an anodic bonding step to bond a cover chip onto the substrate so that the nanochannel is closed.

In another embodiment, the process includes (1) micropatterning a first glass substrate to form a first microelectrode and a second microelectrode, (2) micropatterning said first glass wafer to form a first microchannel portion and a second microchannel portion, (3) depositing a nanoelectrode on said glass wafer between said first microelectrode and said second microelectrode, (4) machining a nanochannel between said first microchannel portion and said second microchannel portion, and (5) bonding a second glass wafer to said first glass wafer.

The nanochannel system is a nanotechnology based rapid DNA sequencing technique that achieves sequencing without the use of lengthy sample pre-treatment and DNA replication currently used by other DNA sequencing techniques. The result is a much faster and cost-effective chip-based sequencing method that can benefit both the biomedical and DNA research communities. The device can sequence a single stand of DNA.

The nanochannel system is embedded with sensing electrodes to detect electrical signals of DNA bases. The electrodes are positioned to produce an electron tunneling system and to guide the DNA as a single strand without folds or loops through the sequencing process. The nanochannel is fabricated by a nanomachining method that is both precise and easy to operate. The fabrication method does not require cleanroom processing and is therefore cheaper to operate than other semiconductor based techniques.

The nanochannel system, fabricated on either a glass or silicon substrate, has channel heights and widths on the order of single to tens of nanometers. The nanochannel length is in the micrometer range. The nanochannel system is equipped with embedded micro or nanoscale electrodes, positioned along the length of the channel for electron tunneling based characterization of nanoscale particles in the channel. Electron tunneling is quantum phenomenon where an electron 'tunnels' through a potential barrier that repels a classical particle with the same energy. In the nanochannel system, the embedded electrodes measure the tunneling current of the nanoparticles as they translocate through the nanochannel. The nanochannel system is particularly suited for DNA sequencing. To accomplish this, individual DNA strands are electrically pulled through the nanochannel, where the DNAs translocate at a lower speed than in a nanopore due to high viscous drag, and the bases in the DNA strand are characterized by their corresponding electron tunneling current in the transverse direction. This method of DNA characterization is expected to yield a much higher temporal and spatial resolution than the nanopore approach.

Particularly important features associated with the invention are: (1) AFM based nanolithography together with anodic bonding can be used to fabricate nanochannel systems; (2) Micro to nanoscale electrodes can be fabricated along the AFM nanochannel for electrical characterization of nanoscale particles in the channel; (3) Fabrication of the nanochannel system is relatively fast and easy by combining MEMS microfabrication with AFM nanolithography; (4) Continuous nanoscale liquid flow can be maintained in the nanochannel; (5) The nanochannel system with embedded electrodes can be used to characterize the electron tunneling current of translocating nanoparticles; (6) The nanochannel system with embedded electrodes can be used to sequence single-stranded DNA with single-base resolution.

These and other features, objects and advantages of the present invention will become better understood from a consideration of the following detailed description of the preferred embodiments and appended claim in conjunction with the drawings as described following.

BRIEF DESCRIPTION OF THE SEVERAL VIEWS OF THE DRAWINGS

FIGS. 7($a$) and 7($b$) are fluorescent images (10×) of the silicon nanochannel system before (FIG. 7($a$)) and after (FIG. 7($b$)) negatively-charged FluoSpheres® microspheres are driven through the nanochannel by a positive electric field.

FIG. 8 is a graph of the instantaneous tunneling current measurement of translocating nanoparticles.

FIG. 40($a$) is a one electrode design, FIG. 40($b$) is a two electrode design, and FIG. 40($c$) is a three electrode design.

FIG. 41($a$) and FIG. 41($b$) are schematics comparing the nanochannel system of Process C and Process D.

FIG. 45($a$) is a cross-sectional side view of FIB milled nanochannels and FIG. 45($b$) is a detailed view of a single nanochannel with 1:1 scaling.

FIG. 46($a$) and FIG. 46($b$) are SEM images of the single electrode configuration with FIB-milled nanochannels.

DETAILED DESCRIPTION OF THE INVENTION

Figure 1:
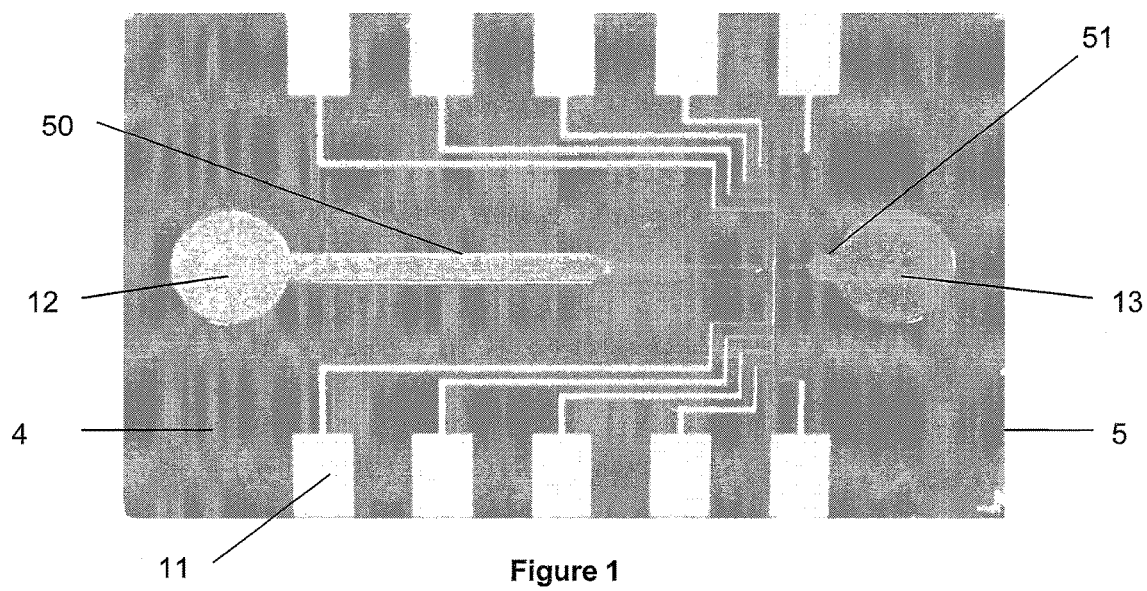
FIG. 1 is a plan view of a microfabricated silicon chip with inlet and outlet reservoirs, microchannel, and a plurality of microelectrodes.
Figure 68:
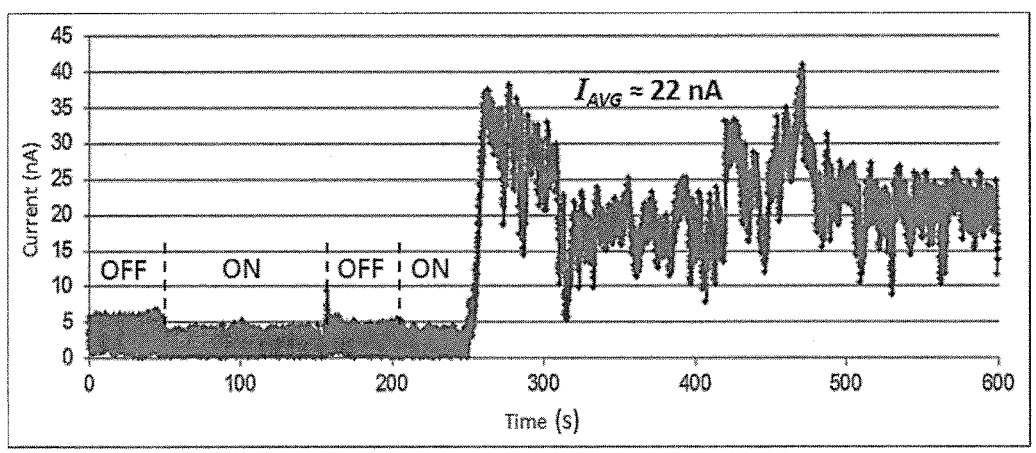
FIG. 68 illustrates a transverse current through Pt nanoelectrodes during nanobead translocation.

With reference to FIGS. 1-68, the preferred embodiments of the present invention may be described. The inventors developed a method of fabricating a nanochannel system comprising the steps of: (1) micropatterning a substrate to form electrodes; (2) micropatterning the substrate to form two microchannel portions; (3) machining a nanochannel between the two microchannel portions; and (4) bonding a cover chip to the substrate, which is described in U.S. patent application Ser. No. 13/768,960 for which priority is claimed and reproduced in paragraphs [0092]-[0104] below.

Figure 2:
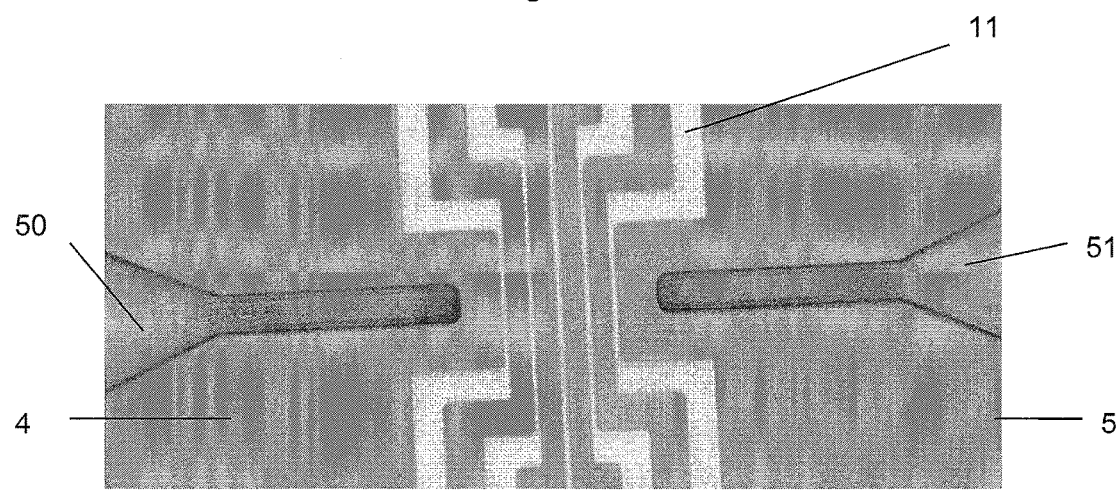
FIG. 2 is a close-up view of the section of FIG. 1 where a nanochannel is to be machined.
Figure 3:
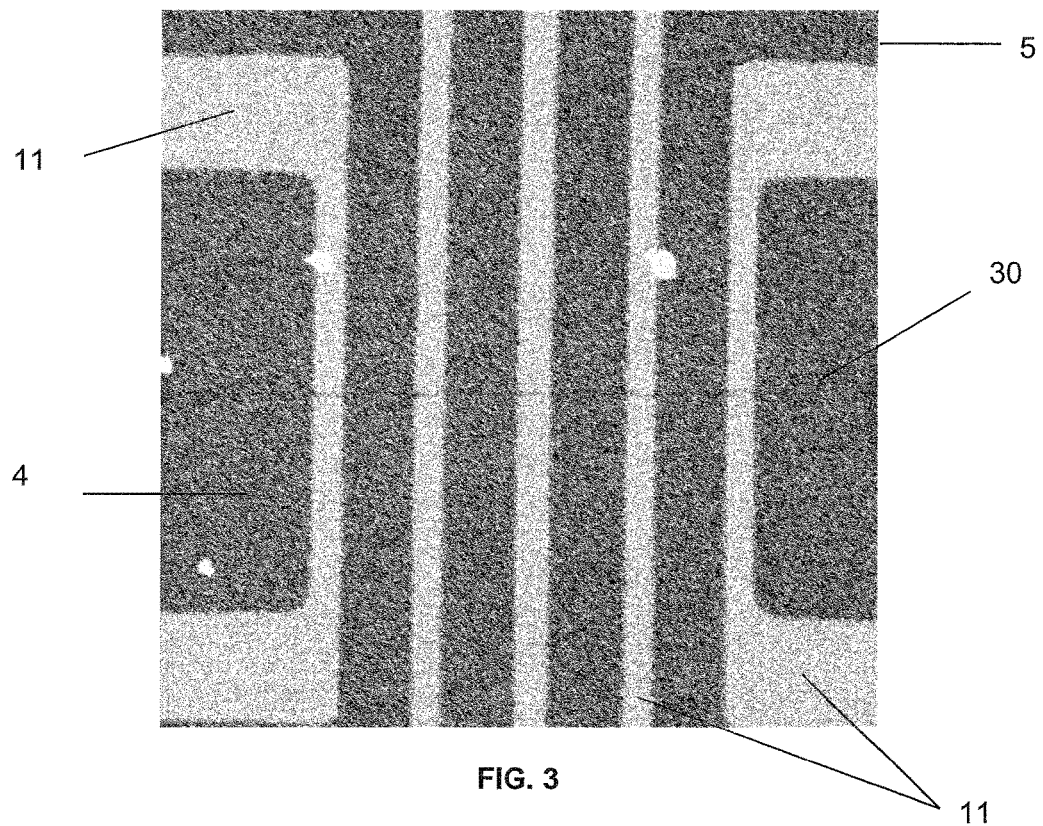
FIG. 3 is a close-up view of FIG. 2 showing a nanochannel machined by AFM nanolithography (30 μm long, 20 nm deep, and 100 nm wide).

The present invention uses AFM nanolithography in conjunction with MEMS microfabrication techniques to create a nanochannel system with integrated microelectrodes 11. The fabrication process involves two micropatterning steps (one to form at least one electrode 11 and another to form a microchannel in two portions—an inlet portion 50 and an outlet portion 51), one AFM nanolithography step, and one chip bonding step. The fabrication process for a silicon nanochannel system begins with the patterning of the microchannel inlet portion 50 and outlet portion 51 and at least one electrode on a substrate, such as a silicon chip 5, as shown in FIGS. 1 and 2. The electrodes 11 may be microelectrodes as shown in FIGS. 1-3 or nanoelectrodes. The electrodes may be formed of various materials known to those skilled in the art, including Cr/Au or Pt/Ti. A plurality of electrodes 11 are desirable.

FIG. 1 is an enlarged picture of a silicon chip 5 fabricated by a MEMS process. The microchannel inlet portion 50 may include an inlet microreservoir 12 and the microchannel 51 may include an outlet microreservoir 13. The microchannel inlet portion 50, inlet microreservoir 12, microchannel 51 and outlet microreservoir 13 are all desirably about 20-μm deep. The microchannel portions 50, 51 along with the inlet microreservoir 12 and the outlet microreservoir 13 serve as the inlet and outlet for the nanochannel 30. The electrodes 11 are desirably about 40-nm thick and reside on top of a 500-nm thick silicon oxide layer 4. High-temperature Pt as the electrode material allows thinner electrodes compatible with the high temperatures and voltage of the anodic bonding step; however, Au electrodes may also be compatible with the anodic bonding step where the electrodes are thicker in the range of about 40 nm to about 100 nm.

FIG. 2 is a close-up picture of the location on the silicon chip 5 where the nanochannel 30 is machined. In this embodiment, five 1-μm wide parallel microelectrodes 11 cross the path of the nanochannel 30. As the nanochannel 30 is machined, each microelectrode 11 is dissected into two matching microelectrodes 11 bordering the outline of the nanochannel 30. With these dissected microelectrodes 11, it becomes possible to measure the transverse electrical impedance of the nanochannel 30 at five distinct locations in the longitudinal direction. When needed, external bridge-type circuits (not shown) can be added to the system to monitor the instantaneous conductivity of the nanochannel 30 as a way to track the movement of a nanoscale object inside the nanochannel 30.

Figure 4:
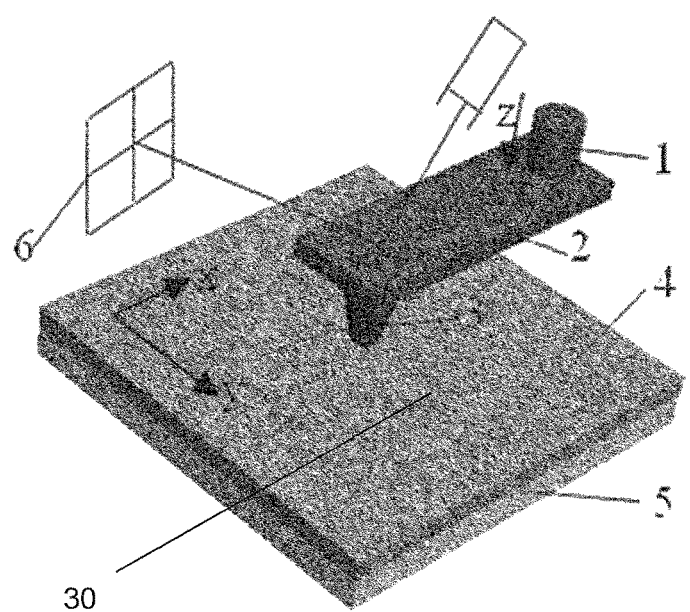
FIG. 4 is a schematic illustration of a setup for AFM machining of a nanochannel.

The nanochannel 30 is machined mechanically between the inlet 50 and outlet portions 51 of the microchannel using AFM nanolithography by means of a setup such as that shown in FIG. 4. A diamond probe tip 3 with a large spring constant and a nanoscale tip radius serves as the cutting tool. A calibration process is carried out in advance to establish the relationship between the tip control parameters such as force and speed, and the resultant dimensions of the nanochannel 30. As the nanochannel 30 is machined, each of the parallel microelectrodes 11 between the microchannels 10 is dissected into two matching tunneling microelectrodes 11 separated by the width of the nanochannel 30 as shown in FIG. 3.

In the nanochannel system shown in FIG. 3, the nanochannel 30 on the silicon chip 5 was mechanically machined in a Dimension 3100 AFM (Veeco Inc., CA) controlled by a Nanoscope IIIa controller. The AFM probe used was an all-diamond nanoindenting tip 3 (PDNISP from Veeco) with a calibrated spring constant of 215 N/m and a nominal tip radius of 40 nm. The tip 3 is mounted on a cantilever 2 which is actuated by piezoelectric tubes (PZT) 1. FIG. 4 demonstrates the basic layout of the AFM machining method. In this method, the AFM tip 3 is pressed against the silicon oxide surface layer 4 of the silicon chip 5 with a constant force (by automatically adjusting the PZT 1 to keep the vertical deflection as sensed by the position sensing device (PSD) 6 constant and then translated along a preplanned path on the surface. Prior research to determine the relationship between the AFM control parameters and the resultant nanochannel dimensions is described in Z. Q. Wang, S. Tung, N. D. Jiao, et al., "Nanochannels on silicon oxide surface fabricated by atomic force microscopy," Proceedings of the 2010 5th IEEE international conference on Nano/Micro Engineered and Molecular Systems, Jan. 20-23, 2010, Xiamen, China, pp. 630-633, 2010. A vertical deflection signal of 4.0V and a translation speed of 1 μm/s have been found to be acceptable in the practice of the present invention.

Figure 5:
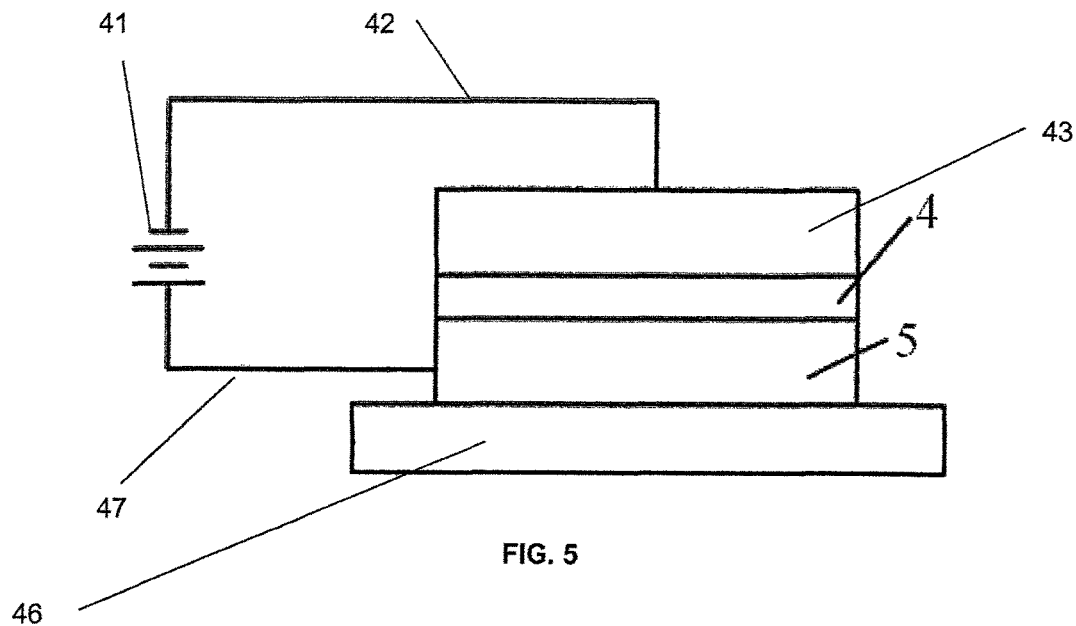
FIG. 5 is a schematic illustration of a setup for anodic bonding of a cover chip to a silicon substrate.

Once the nanochannel 30 is formed, the substrate chip 5 is capped off by a matching Pyrex® glass cover chip to form a closed nanochannel 30 through anodic bonding. While Pyrex® glass is the preferred material for use in the anodic bonding step, other anodic bonding materials and techniques as known to those skilled in the art may be used on the practice of the present invention. Anodic bonding is a technique to hermetically seal a substrate by bonding a cover chip to the substrate using a combination of heat and a strong electrostatic field. FIG. 5 is a schematic illustration of a setup for anodic bonding of the cover chip 43 to the silicon substrate 5.

The MEMS silicon substrate 5 with the AFM-machined nanochannel 30 was sealed off by a matching Pyrex® glass cover chip 43 through anodic bonding. The 500-μm thick silicon substrate 5 was placed on a hot plate 6 and linked to the anode 47 of a voltage-adjustable direct current supply 41. The Pyrex® glass cover chip 43 (0.5 mm thick) with pre-drilled through holes over the inlet 12 and outlet microreservoirs 13 was placed on top of the silicon substrate 5 and linked to the cathode 42 of the current supply 41. The hot plate 46 was maintained at a temperature to 550° C. At this plate temperature, the surface temperature of the silicon substrate 5 was measured as 420° C. by an infrared radiation thermometer. The anodic bonding process was performed at a voltage of 600V. The current supply showed the current to be between 0.2 and 0.4 mA at the beginning of the process. After about 20 minutes, the current dropped to about 0.01 mA at which point the bonding process was terminated.

A custom-built anodic bonding platform for performing the anodic bonding step included a 0.3-mm thick graphite disk (not shown) between the hotplate 6 and the silicon chip 5 to provide a uniform temperature distribution in the silicon chip. A 1 mm thick aluminum pressing block (not shown) on top of the Pyrex® glass cover chip 43 ensured a good physical contact between the Pyrex® glass cover chip 43 and the silicon substrate 5. The bonded chip was provided with a microfluidic connector (not shown) to the inlet reservoir 12 through the pre-drilled hole in the cover chip 43. Another pre-drilled hole over the outlet reservoir 13 provided an outlet to the nanochannel 30.

Figure 6:
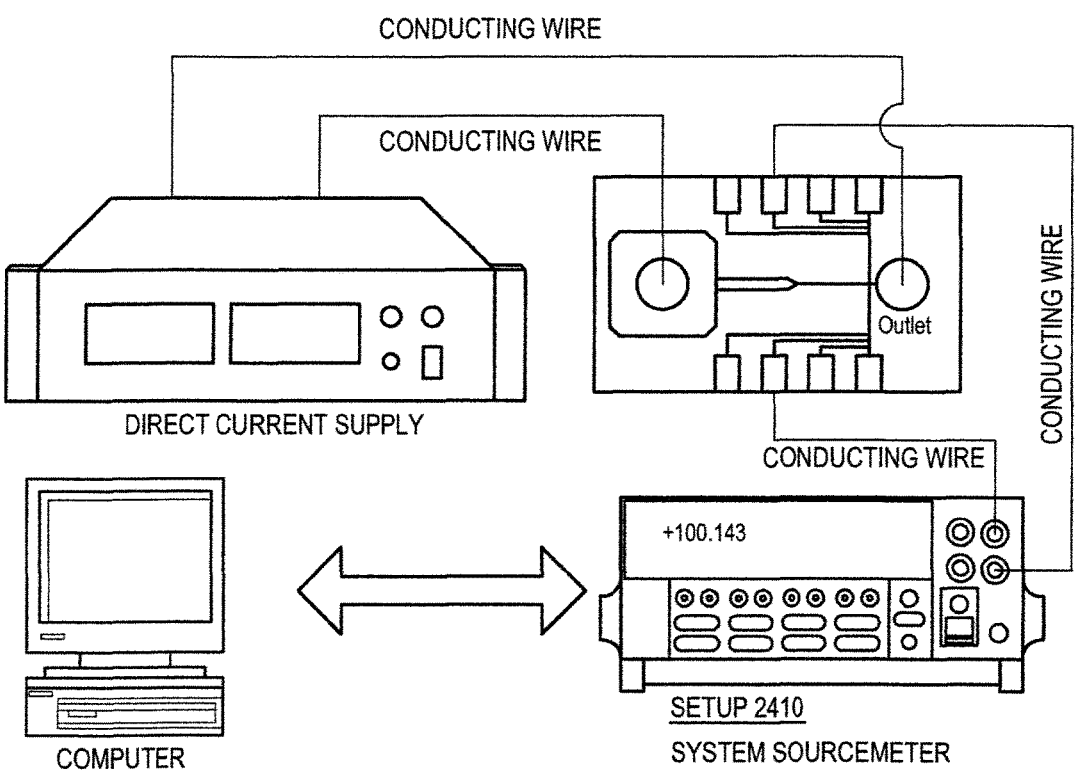
FIG. 6 illustrates an experimental setup for driving negatively-charged FluoSpheres® microspheres through a nanochannel system by positive electric field while measuring the electrical current of the transverse electrodes.

FIG. 6 shows an experimental setup for driving negatively-charged FluoSpheres® microspheres through the nanochannel 30 by a positive electric field while measuring the electrical current of the transverse electrodes 11. 20-nm carboxyl-modified FluoSpheres® microspheres (F-8787 from Invitrogen) were translocated through the nanochannel system through the use of an externally applied electric field. Since the FluoSpheres® microspheres are negatively charged, a positive voltage at the outlet reservoir 13, if high enough, tends to pull the nanobeads from the negatively-biased inlet reservoir 12 to the outlet reservoir 13 through the nanochannel 30. Once initiated, the nanobead flow is monitored by the transverse electrical current across the pairs of electrodes 11 positioned along the nanochannel 30.

FIGS. 7(a) and 7(b) show fluorescent images (10×) of the silicon nanochannel system before (FIG. 7(a)) and after (FIG. 7(b)) negatively-charged FluoSpheres® microspheres are driven through the nanochannel 30 by a positive electric field. FIG. 7(a) demonstrates the filling of the inlet portion 50 of the microchannel by the FluoSpheres® microspheres suspension. Following this step, the outlet reservoir 13 is filled with 0.01M phosphate-buffered saline (PBS) and a 10VDC bias is applied between the inlet and outlet reservoirs 12, 13. FIG. 7(b) demonstrates the result after a 3 min delay. The fluorescent pictures indicate that the upstream FluoSpheres® microspheres have been successfully translocated through the nanochannel 30 to the outlet reservoir 13 by the voltage bias.

FIG. 8 is a graph showing the instantaneous tunneling current measurement of translocating nanoparticles. FIG. 8 demonstrates the transverse electrical current measured by one pair of electrodes 11 in the nanochannel 30. When a voltage of 5 VDC is applied, a large transverse current is obtained, indicating the flow of the conductive nanobeads significantly enhances the electrical conductivity of the nanochannel 30. Preliminary calculations based on quantum theories indicate the level of the current measured is consistent with the expected tunneling current of the nanobeads.

The nanochannel system fabricated by the method of the present invention has applications in DNA sequencing, protein analysis, virus detection, nanofluidic accelerometers, nanofluidic gyroscopes, nanoscale heat and mass transfer studies, and nano-filtration.

The AFM method for nanochannel formation does not require the expensive and time-consuming cleanroom techniques used by other nanochannel fabrication methods. In addition, the process is repeatable due to the precision control mechanism already in place in the AFM. Finally, the AFM method is scalable; multiple nanochannels can be machined simultaneously through the use of a multiple AFM tip setup currently being developed by AFM manufacturers. The AFM method is more cost-effective that other nanolithographic methods such as e-beam and focused ion beam techniques, which can only machine one channel at a time.

Examples of further fabrication methods and testing of the fabricated nanochannel systems and devices are provided below:

Fabrication Materials and Methods: The nanofluidic device began with the selection of a substrate material. Corning Pyrex® glass 7740 was the chosen material due to its transparency, rigidity, biocompatibility, and low coefficient of thermal expansion. The Pyrex® glass wafers were 100 mm in diameter and 500 µm thick. The works described in this research consisted of four major MEMS processes. The first process to be explained is referred to as Process A [38]. The goal of this process was to fabricate a Pyrex® glass device with smooth, well-defined microchannel walls. Process A was aimed to duplicate and verify the results from previous research [38]. Process B helped establish the importance of using chrome (Cr) and gold (Au) as masking layers for wet etching features in the Pyrex® glass wafer. Process C was the first time that electrodes were introduced in the chip design. The Cr/Au was initially used as a masking layer for wet etching and then used again to generate patterned microelectrodes. Finally, Process D was implemented to improve upon the microelectrode design from Process C by decreasing preparation and testing times and helped make the nanofluidic device more efficient.

Figure 9:
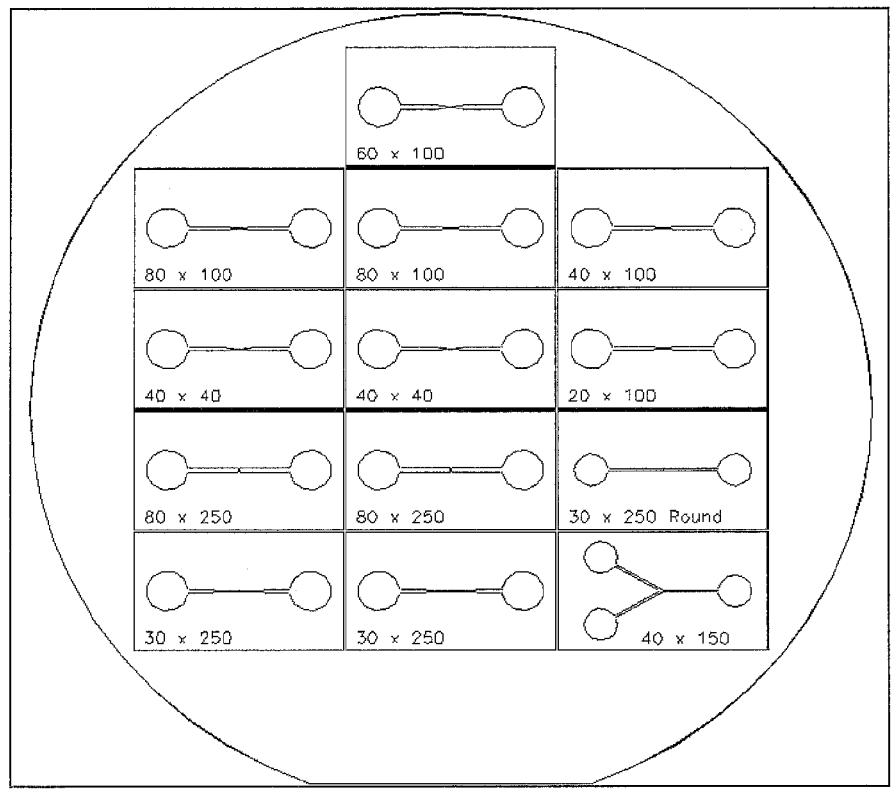
FIG. 9 is a design of photolithography mask for microchannels fabricated in Process A.
Figure 10:
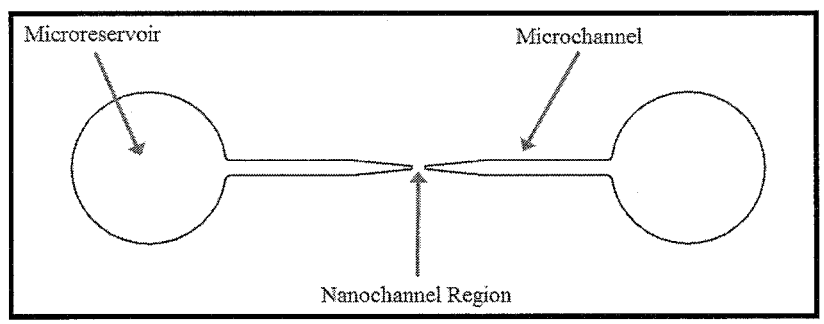
FIG. 10 is a schematic of a single microchannel pattern.

Process A: This process was the first attempt at microfabrication. The processing steps were not well defined and tested, leaving a lot of room for error and speculation. The entire process will be explained in chronological order of the fabrication steps. First, the layout of the transparency mask is displayed in FIG. 9 below. In order to pattern microchannels onto the Pyrex® glass wafer during photolithography, a mask must be used. The masks used in this research were all transparency masks due to their low price and availability. This particular mask was designed by a previous student and has been used previously [38]. It was originally designed in AutoCAD and included 13 different chips with 9 different microchannel geometries. The simplest geometry is shown in FIG. 10. This design consisted of two microreservoirs. These are known as the inlet (left) and the outlet (right). The reservoirs connect to microscale channels, known as microchannels. The nanochannel region will be referred to many times, and it is defined as the area between the two microchannels. The method to fabricate such microchannels in Pyrex® glass could not be easily replicated and, therefore, needed to be revisited.

Figure 11:
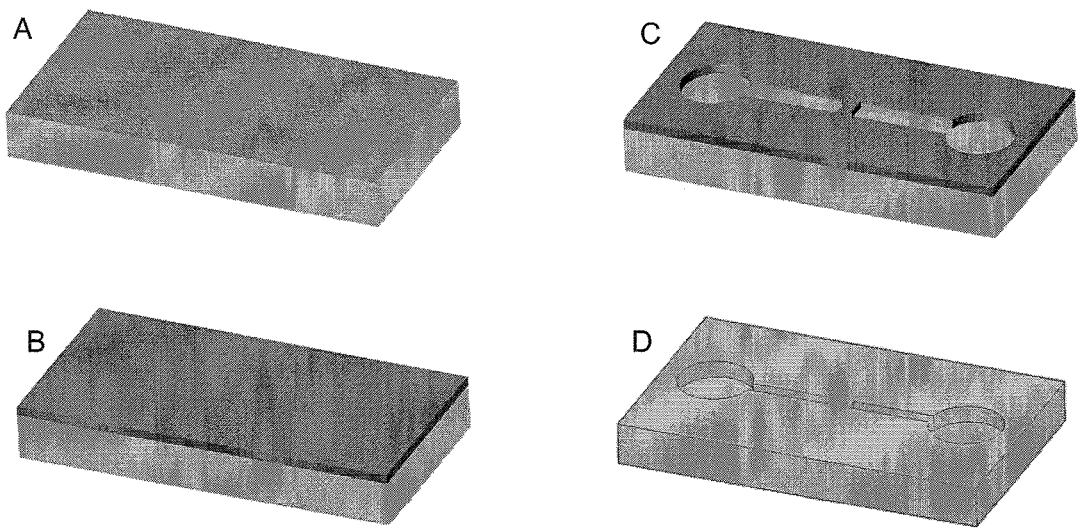
FIG. 11 is a microfabrication process flow of Process A
Figures 12A, 12B:
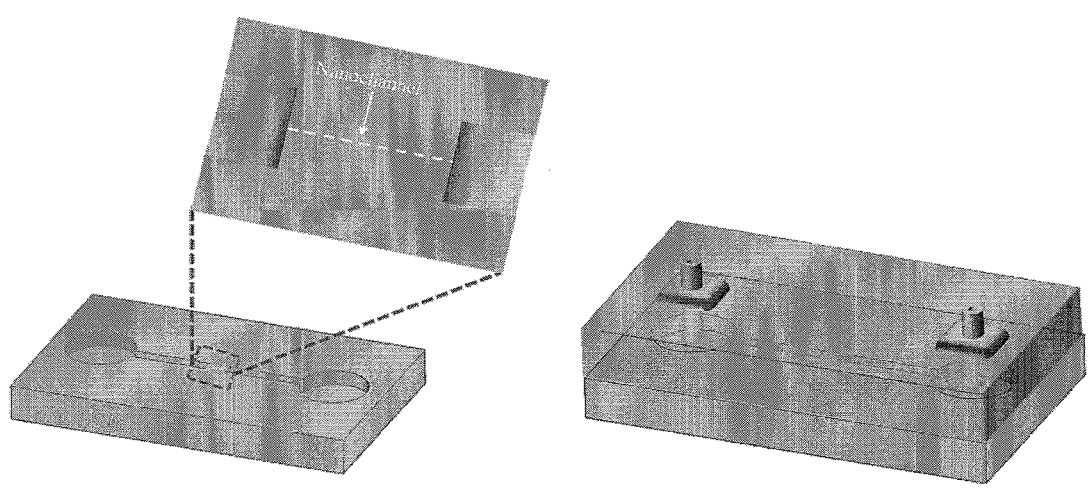
FIG. 12($a$) and FIG. 12($b$) illustrate a nanochannel formation (FIG. 12($a$)) and packaging (FIG. 12($b$)).

Cleanroom Fabrication: The attempt to fabricate devices for testing is described in this section. All cleanroom fabrication was performed at the High Density Electronics Center (HiDEC) at the University of Arkansas Engineering Research Center (ENRC). FIG. 11 shows the microfabrication process flow of Process A. The process began with the 500 µm thick bare Pyrex® glass 7740 substrate (A). Then, photoresist (PR) was spin coated on the wafer at a 4 µm thickness (B). The wafer was patterned with the microchannel design (C). The microchannels were etched into the bulk of the substrate and the PR was stripped away (D). The remaining fabrication is displayed by FIG. 12. The nanochannel was realized by AFM nanolithography (left) and the chip was packaged through anodic bonding (right).

The steps of FIG. 11 will be explained in order to understand the details of the cleanroom fabrication process. First, AZ4330 PR was applied to the wafer by an Eaton spin coater to a controlled thickness of 4 μm. The PR thickness was controlled by monitoring the spin coater's RPM during the ramp up, dwell, and ramp down cycles. The wafer was then soft baked on a hot plate at 110° C. for 2 minutes to improve the PR-wafer adhesion. Next, the mask pattern from FIG. 9 was transferred to the wafer by standard UV photolithography on the Karl Suss aligner. The exposure time was determined by the following equation, $$t = \frac{E}{I} \qquad \text{Equation 1}$$

where t is the exposure time (s), E is the energy needed to expose the PR (mJ/cm$^2$), and I is the intensity of the UV lamp in the Karl Suss aligner (mW/cm$^2$). The intensity was obtained from the aligner, but the energy needed to be calculated separately, as it depended on the type and thickness of PR. The equation for energy follows, $$E = kT \qquad \text{Equation 2}$$

where E is the energy, k is the PR constant, and T is the PR thickness (μm). For AZ4330 PR, the PR constant, k, was 45. Therefore, the energy for this process was 180 mJ/cm$^2$ and the intensity was 10 mW/cm$^2$, resulting in an 18 s exposure time. Immediately after the wafer was exposed, it was developed in a solution of 3:1 DI water:AZ400K developer for 90 s. This step removed all PR that was previously exposed by UV light (microchannels). The microchannel patterns were then inspected under a microscope to verify that the patterns were fully developed and well defined. After inspection, the wafer was taken to the acid wet bench for microchannel etching.

The central wet etchant used for the Pyrex® glass etch was 10:1 Buffered Oxide Etch (BOE). BOE is composed of aqueous ammonium fluoride (NH$_4$), hydrogen fluoride (HF), and water, and etches Pyrex® glass at ≈0.1 μm/min. Ammonium fluoride and water were added to the HF to help slow down the etch rate. If the Pyrex® glass wafer was etched in HF alone, the quality of the etch would have been poor due to the high etch rate of Pyrex® glass in HF (14.3 μm/min) [39]. The 10:1 BOE (10 parts NH$_4$ to 1 part HF) was further diluted with Hydrochloric acid and more DI water. The final etching solution was 1:1.2:1.7 BOE:HCl:H$_2$O. Hydrochloric acid was added to improve the quality of the etch [40]. Table 1 contains the chemical composition of Pyrex® glass 7740 [41]. The HF etches the SiO$_2$, but the other three oxides give insoluble products in HF solution. The addition of HCl transforms the insoluble products to soluble products, thus improving the etch quality [42].

TABLE 1

| Pyrex 7740 chemical composition | |
|---|---|
| Compound | % approximation |
| SiO$_2$ | 80.6 |
| B$_2$O$_3$ | 13.0 |
| Na$_2$O | 4.0 |
| Al$_2$O$_3$ | 2.3 |
| Na$_2$O | 0.1 |

Wet isotropic etchants, such as BOE, etch in both the vertical and lateral direction. With the addition of HCl, the new solution had an etch rate of 0.15 μm/min, suggesting that HCl increased the etch rate of glass in BOE. The minimum etch depth of the microchannels was 4 μm due to the diameter of the microreservoirs. If the channels were not etched at least 4 μm deep, then they could collapse during the anodic bonding step due to a low aspect ratio (ratio of channel depth to channel width) [43]. Therefore, with an etch rate of 0.15 μm/min, the wafer had to be in the etchant for at least 27 minutes to achieve a 4 μm deep etch.

Figure 13:
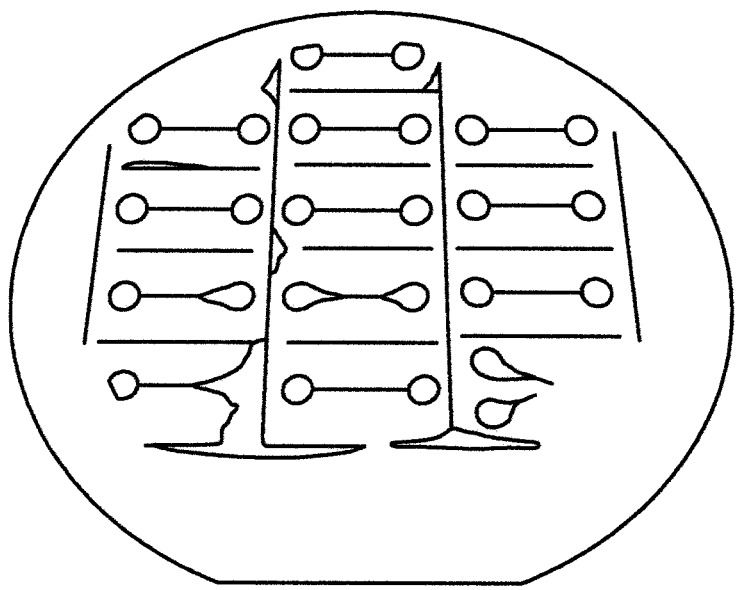
FIG. 13 illustrates a Pyrex® glass wafer with failed PR.

Failure of Photoresist: Hydrogen Fluoride is known to attack PR and could strip away the patterned PR on the Pyrex® glass wafer. There are two types of PR failure due to HF attacks: notching defects and lift-off. Lift-off occurs when the HF in the BOE attacks the PR in the lateral direction and wedges itself between the glass surface and the PR causing the PR to be removed. Notching defects occur when the HF attacks the PR in the normal direction, causing small through holes in the PR surface. FIG. 13 displays a Pyrex® glass wafer with PR failure due to HF attacks. The major defect in this scenario was lift-off. This wafer was etched for only 7 minutes. If the wafer was not removed from the etchant, then the microchannel patterns would no longer be defined and the wafer would be worthless. Since the wafer was removed after just 7 minutes (instead of the required 27 minutes), the microchannels were only about 1 μm deep, which was too shallow for anodic bonding. The failure of PR was a major problem, and needed to be resolved before proper microchannels could be fabricated by Process A.

Photoresist Adhesion Experiments: In order to produce deep, clean microchannels, multiple experiments were performed dealing with the fabrication process. Overall, the fabrication variables that were tested include Hexamethyldisilazane (HMDS), thicker PR, hard bake temperature/time, BOE concentration, and finally a Cr/Au masking layer.

HMDS is a standard process in photolithography to increase adhesion between PR and silicon dioxide[44]. This 30 minute HMDS step was added to the beginning of the fabrication process. The HMDS oven would first heat up and dehydrate the wafer and then apply a thin adhesion-promoting layer of HMDS. After proceeding through the other fabrication steps, the resist failed after approximately 9 min 30 sec in the BOE. This meant that the HMDS step did help PR adhesion, but not to the extent where the wafer could be etched for 27 minutes.

Next, the PR was changed from AZ4330 to AZ4620. This new PR had a higher viscosity, and had the potential of being thick enough to at least fight off the notching attack of the BOE solution. The PR was spun onto the Pyrex® glass wafer at 6 μm thick after applying the HMDS step. From this point, all of the other steps were followed accordingly. Although the thicker PR did reduce the notching defects, the lateral attack was the same and the PR failed after just 9 minutes.

Next, a hard bake step was incorporated to the fabrication process. There was already had a soft bake step of 110° C. for 2 minutes after spin coating PR onto the wafer. The hard bake step was added after the inspection of fully developed microchannel patterns in the PR. Hard baking PR on glass can further enhance the PR-glass adhesion. In previous PR on glass adhesion experiments, several notable hard bake temperatures found from literature were 120, 130, 145, and 160° C. [40, 45-47]. Most articles suggested that 120° C. is the most proven hard bake temperature for PR-glass adhesion. Therefore, three different hard bake times of 10, 20, and 30 minutes each at 120° C. were tested first. The PR failed in the etchant each time around 11 minutes. Due to limited time and resources, the next hard bake experiments were performed at 130, 145, and 160° C. for 30 minutes each. From the 120° C. hard bake experiments, it was apparent that hard bake time did not seriously affect overall adhesion. The 130° C. hard bake allowed the PR to adhere for about 12 minutes, 145° C. for about 7 minutes, and 160° C. for about 5 minutes in the BOE solution. This meant that the ideal hard bake temperature for the wafers was 130° C. for 30 minutes. However, this result was still inadequate for the overall process goal. The maximum etch depth achieved was 1.6 μm, which was less than half of the desired depth of 4 μm.

Although the hard bake step did help extend the total etch time from 9 to 12 minutes, more improvement was still necessary. The next variable under experimentation was the BOE:HCl:H$_2$O concentration. The different concentrations tested included 1:2:2, 1:1.8:1.8, 1:1.6:1.6, 1:1.4:1.4, 1:1.4:1, and 1:1.2:1.7. Chips processed and hard baked at 130° C. for 30 minutes were diced and etched individually in the concentrated solution. The PR only held for about 5 minutes for most concentrations and the etch rate was about 0.15 μm/min for all concentrations. For the 1:1.2:1.7 concentration, however, the PR held for 6 min 30 sec. The conclusion from all of these PR-glass adhesion experiments was that there had to be a major change in the fabrication process for successful microchannels to be produced. Previous research has shown that other masking layers can be used for glass etching in addition to photoresist. One such masking material is the combination of Chrome and Gold through thermal evaporation [46].

Figure 14:
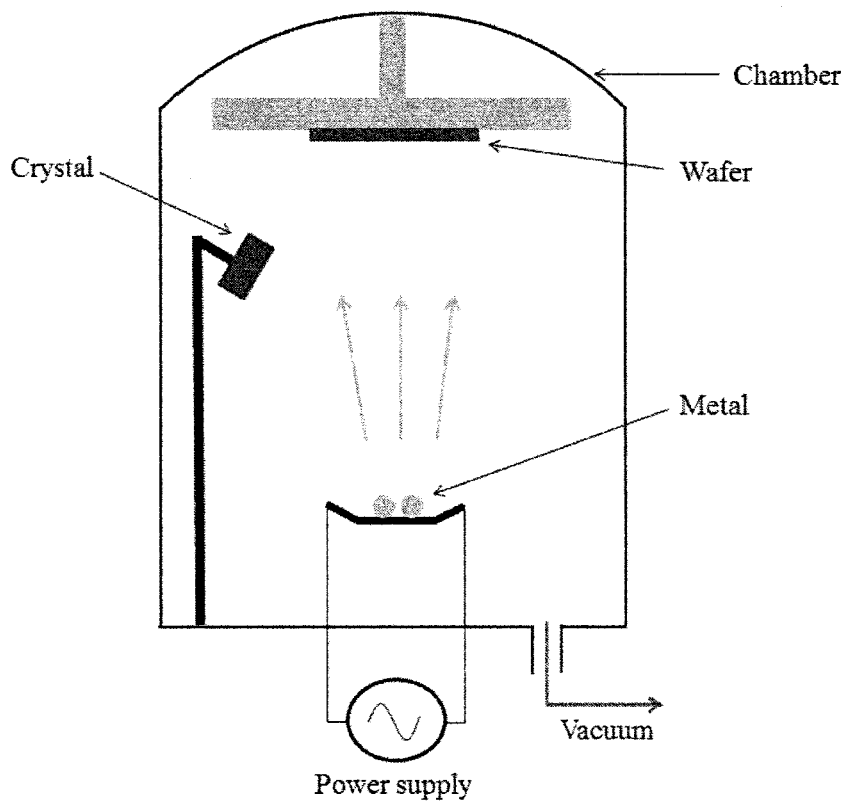
FIG. 14 is a schematic of the thermal evaporation process.

Process B: Process B incorporated the addition of a thermal evaporation step. Thermal evaporation is a standard procedure in MEMS processing where metals are evaporated onto a desired surface at thin, controlled thicknesses. The three types of evaporation include filament, E-beam, and flash evaporation. The cleanroom at HiDEC features a filament thermal evaporator. This process mainly consists of the gradual heating of a filament of the metal to be evaporated. The power source applies AC current to the metal source, causing it to heat up and melt. The chamber is under high vacuum, and evaporated particles from the metal travel directly onto the wafer. A crystal monitors the evaporation rate and the evaporated amount. The wafer must be high above (1-2 ft) the metal source to ensure that solid particles do not reach the wafer, and they are simply taped to a wafer platform located at the top of the chamber. FIG. 14 demonstrates the thermal evaporation process with gold as the metal source. This is a precise process, as the metal layer thickness can be controlled at the single nanometer scale.

Figure 15:
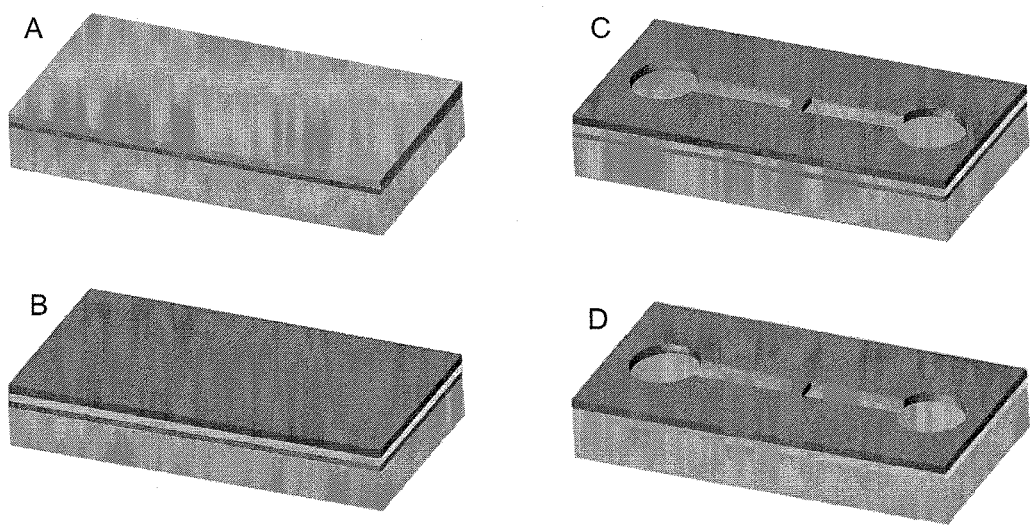
FIG. 15 is a microfabrication process flow for Process B.

Cr/Au Masking Layer: For proper microchannel etching in glass, chrome (Cr) and gold (Au) were applied to the wafer as a masking layer. The Cr was added first to act as the adhesion layer between the Pyrex® glass and Au. Next, a layer of gold was evaporated onto the chrome layer. This top layer of gold served as the masking layer because it gold is inert to HF. The Cr/Au layers were then patterned for microchannel etching. This process is referred to as Process B and the microfabrication process is displayed in FIG. 15. In short, Cr/Au was evaporated on the wafer (A) and PR was spun onto the wafer (B). The PR was patterned with the same mask from Process A (C) and the microchannels were etched in the bulk of the substrate (D). The remaining process is not displayed, as it was similar to that of Process A.

In more detail, Process B began with the thermal evaporation of Cr/Au onto the Pyrex® glass wafer at the HiDEC cleanroom facility. First, the metals were loaded into the evaporation chamber. The Cr was coated over a tungsten rod and was inserted into the chamber first. Next, 6 Au nuggets were placed inside three alumina coated foil dimple boats (2 nuggets per boat). A single boat with 2 Au nuggets has the capability of evaporating at least 100 nm of thickness on the wafer. After the Cr/Au metals were loaded, the evaporation chamber was pumped down to 5×10$^{-6}$ mbar. Just 15 nm of Cr was evaporated on the Pyrex® glass wafer, followed by the evaporation of approximately 420 nm of Au (140 nm per boat). The evaporation rate of the metals was determined by the amount of current being passed through the filament. The current started at 0 and was increased by 0.25 A every 5 seconds for both the Cr and Au evaporation. The maximum current for Cr and Au was 2.2 A and 4.0 A respectively. When maximum current was reached, the average evaporation rate was ≈0.4 nm/s. The chamber was then vented and the wafers were removed with a total metal evaporation thickness of approximately 435 nm (15 nm Cr, 420 nm Au).

Figure 16:
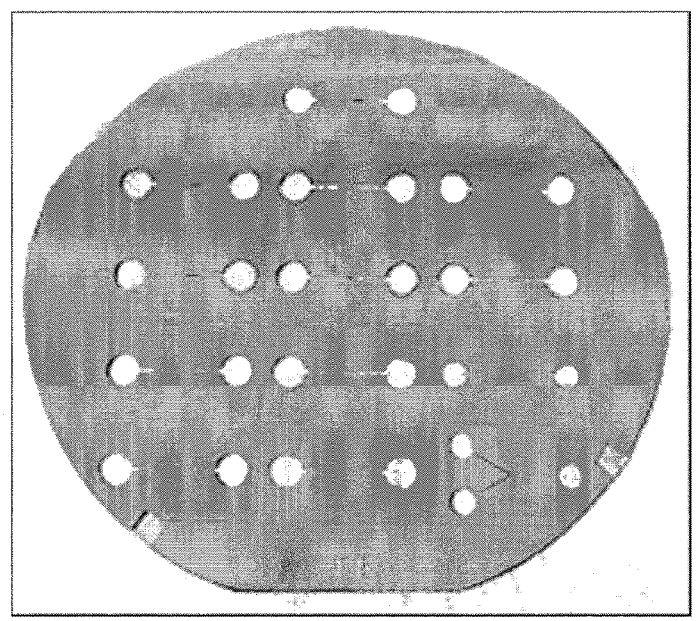
FIG. 16 illustrates a Cr/Au wafer after a 50 minute etch.

The next step in Process B was to apply PR (4 μm thick) and pattern the microchannels onto the Cr/Au surface. A soft bake of 100° C. for 2 min was executed, and the exposure time on the Karl Suss aligner was 18 s. The exposed wafer was developed for 90 sec in the same developing solution from Process A. After inspection, the PR was hard baked on the Cr/Au for 30 min at 120° C. Although the Au was serving as the primary masking layer for the Pyrex® glass etch, the PR was still hard baked so it would serve as an additional masking layer. During the hard bake step, three etchants were prepared at the acid wet bench: Au etch (GE-8148—10% Iodine, 20% Potassium Iodide, 10% Ammonium Phosphate Dibasic, and 60% H$_2$O), Cr etch (CEP-200—6% Perchloric acid, 9% Cerric Ammonium Nitrate, and other non-hazardous raw materials), and BOE. After the hard bake step, the wafer was submerged into the Au etch first for 2 min. After rinsing the wafer off with DI water, it was placed in the Cr etch for 30 s. Once both the Au and Cr layers were stripped, the entire wafer was immersed in the BOE. The goal was to etch channels at least 4 μm deep. With an etch rate of 0.15 μm/minute, the PR had to last at least 27 minutes. During Process A, the PR always failed during the BOE step somewhere between 5 and 12 minutes. This time, however, with the Au masking layer, the PR did not fail after 30 minutes of etching in BOE. It was apparent that the PR had a much higher level of adhesion to the Au layer than the Pyrex® glass wafer. After 20 more minutes of etching, the PR continued to stick to the gold. This wafer is displayed in FIG. 16. The light red swirls represent the PR that still remained on the wafer after etching. Even though the PR remained on the wafer, Au was the primary masking material for microchannel etching.

Figure 17:
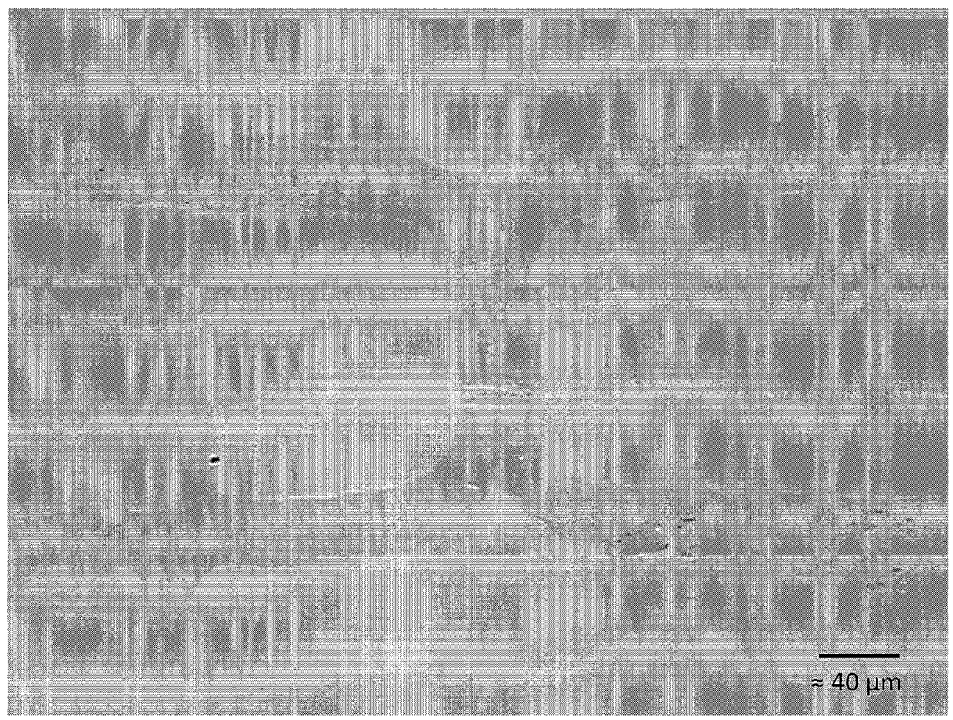
FIG. 17 is a top view microscope snapshot of 7.3 μm deep microchannels.

Finally, the wafer was removed from the BOE solution after 50 minutes, and the PR, Au, and Cr were stripped from the wafer with their respective etchants. The wafer was taken to the dektak profilometer to verify the microchannel depth. A dektak profilometer is a surface profilometer that consists of a stylus that is dragged across the sample surface at a low force. Dektak profilometers typically have a vertical resolution between 5-10 Å and a lateral resolution around 10-15 μm [48, 49]. The profile data was transferred to a PC and printed out for analysis. The first wafer from Process B had a microchannel depth of 7.3 μm. This channel depth indicated that the BOE solution etched the Pyrex® glass at 0.146 μm/min, and the microchannel's aspect ratio was suitable for anodic bonding. FIG. 17 is an optical microscope snapshot of the top view of 7.3 μm deep microchannels etched in BOE for 50 minutes with a 420 nm thick Cr/Au masking layer. There were several characteristics of this image that are noteworthy. First, the channel walls appeared to be wide and rough. Next, there were multiple random defects along the microchannel walls. This was most likely due to small notching defects in the masking layers. Finally, the two microchannels essentially collided with each other. This was a direct result of the isotropic nature of BOE.

Figure 18:
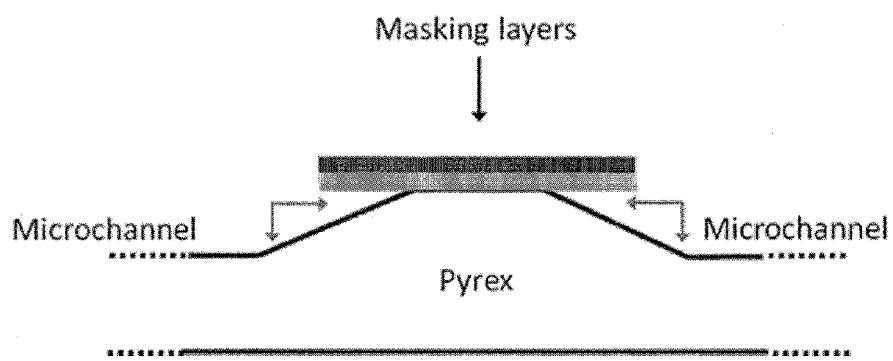
FIG. 18 is a schematic demonstrating how BOE solution undercuts PR during wet etching of Pyrex® glass.

There are two different types of wet etchants: isotropic and anisotropic. BOE etches $SiO_2$ isotropically in nature. Isotropic etchants etch away the desired material in all directions at equal rates. Anisotropic etchants, such as Potassium Hydroxide (KOH) with silicon, etch primarily in one direction. When BOE was used to etch Pyrex® glass with a PR masking layer, the PR was undercut by the BOE. The etch direction is represented by the blue arrows in FIG. 18. The BOE ate through the PR and the Cr/Au layers and etched away small defects from the Pyrex® glass wafer during the 50 min etch. The microchannels on the chip from FIG. 17 were designed to be 40 μm apart. The etch depth of this chip was 7.3 μm. In order for the two microchannels to collide with each other, they traveled 20 μm towards each other, yielding a lateral etch rate of 0.4 μm/min (2.67 times greater than the vertical etch rate). Typically, BOE etches Pyrex® glass with a 1:1 isotropy [46], but this experiment yielded a 2.67:1 isotropy. This large isotropy of Pyrex® glass in BOE with a Cr/Au mask is a common issue. Isotropies as large as 4.6:1 have been reported previously due to the quality of the Cr deposition [50]. When Cr is exposed to air, a thin layer of oxide grows on its surface. This allows the BOE to attack the chromium oxide layer underneath the Au and PR layers, resulting in undercutting and isotropy higher than 1:1 [51]. Therefore, this entire wafer was useless, for there was not any space between the microchannels to scratch a nanochannel.

Figure 19:
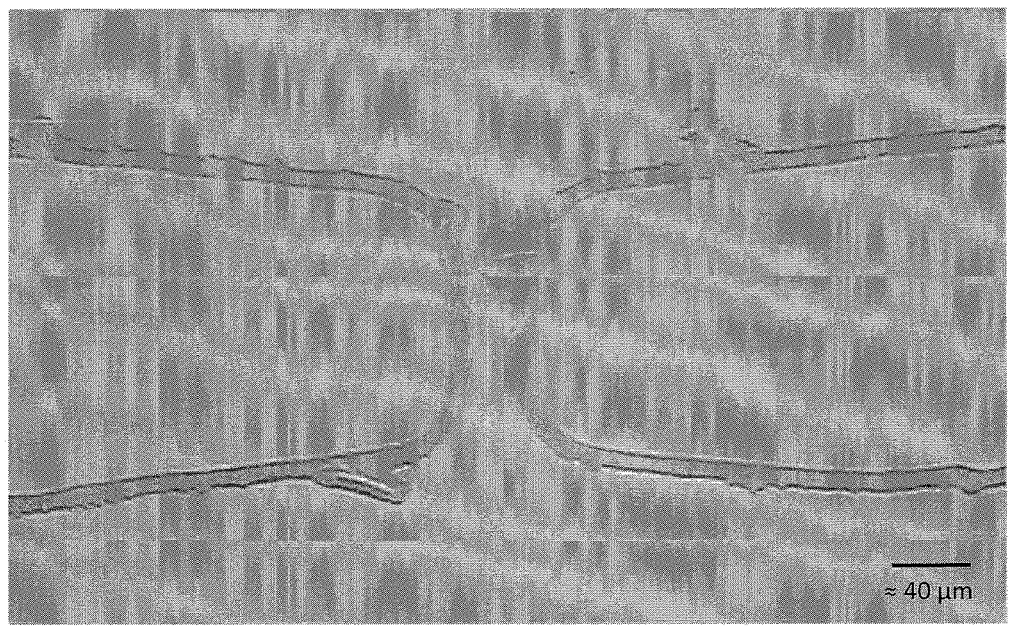
FIG. 19 is a top view microscope snapshot of 2.6 μm deep microchannels.

Process B—Trial 2: Another wafer was processed following the same procedure detailed in Section 2.2.2 for Process B, but the etching time was changed from 50 minutes to 20 minutes. The shorter etch time decreased both the vertical and lateral etched distance of the microchannels. Another objective was to see if the shorter etch time would decrease the channel wall roughness and the notching defects. After the fabrication steps and etching, the dektak profilometer verified the microchannel depth to be 2.6 μm, yielding a vertical etch rate of 0.13 μm/min. A top view of a chip from this process is displayed in FIG. 19. This chip had the same design geometry as FIG. 17, but the microchannel walls did not collide this time. AFM measurements verified that each microchannel wall moved 7.5 μm in the lateral direction, yielding a lateral etch rate of 0.375 μm/min (2.88 times greater than the vertical etch rate). The image in FIG. 19 verified that the microchannel walls were much smoother than shown in FIG. 17. There were still significant notching defects in the 20 min etched chip, but the overall etch quality of this chip was superior when compared to the 50 min etched chip. The next step in the overall nanofluidic system fabrication was AFM scratching. This step was skipped since the microchannels were only etched 2.6 μm deep. Preliminary anodic bonding experiments needed to be carried out to ensure that the shallow microchannels would not collapse.

Figure 20:
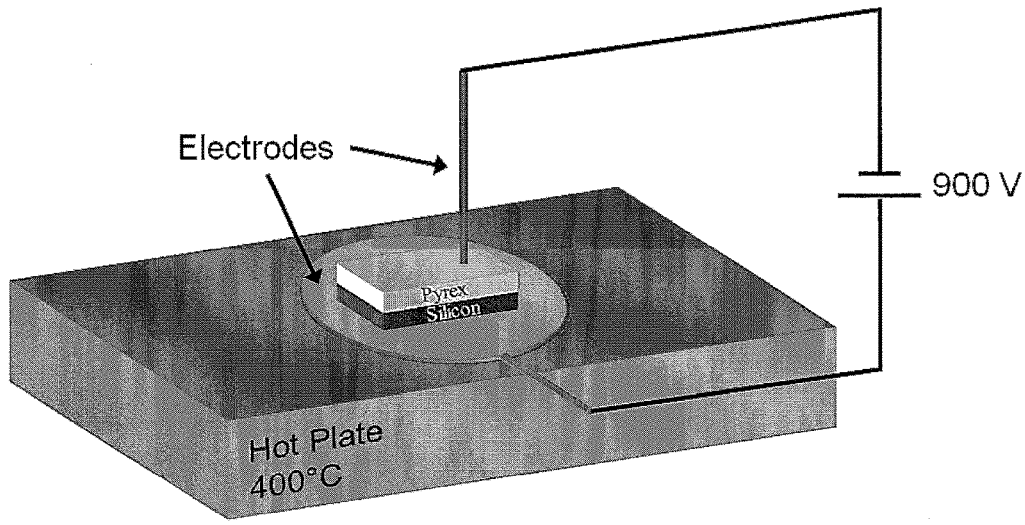
FIG. 20 illustrates the anodic bonding process between Pyrex® glass and silicon.

Anodic Bonding: Anodic bonding is a permanent bonding process between silicon and borosilicate glass. This technique uses high DC voltage and high temperature to create an irreversible $SiO_2$ seal between the two substrates. The experimental setup is displayed in FIG. 20 below. Anodic bonding is a process that combines electrostatic and electrochemical principles, where temperatures and voltages typically range from 300-450° C. and 500-1000 V. A brass electrode was placed directly on the hot plate and the bare silicon chip was placed directly on the chuck. The Pyrex® glass chip was placed directly on the silicon chip (features faced down) and the top electrode was lowered into contact with the Pyrex® glass. A negative bias was applied to the Pyrex® glass, allowing $Na^+$ ions in the Pyrex to diffuse out of the bonding interface to up to the cathode. The diffusion of $Na^+$ ions creates a depletion region at the bonding interface between the Pyrex® glass and Si. At the bonding interface, the Pyrex® glass was negatively charged compared to the Si due to its remaining oxygen ions. These oxygen ions are attracted to silicon under the high electric field, and they migrate across the depletion region into the silicon to create a permanent $SiO_2$ bond.

To ensure proper bonding, the Pyrex® glass and silicon substrates must be cleaned thoroughly. Piranha solution, a 3:1 mixture of sulfuric acid ($H_2SO_4$) and 30% hydrogen peroxide and ($H_2O_2$), served as the cleaning agent. It was heated to 235° C. until it began to boil (10-15 minutes). Then, the chips were submerged into the Piranha for 10 minutes. One advantage of Piranha cleaning is the removal of organic residues. Moreover, since this solution is a strong oxidizing agent, OH groups will be added to the surface of the chips, making them more hydrophilic. Hydrophilicity is a crucial characteristic for future flow tests that will be performed within the nanochannel system. The Pyrex® glass and Si chips experience a consistent, irreversible anodic bond when they are cleaned with Piranha.

The Pyrex® glass chips fabricated during process B contained microchannels that were only 2.6 μm deep. This shallow channel depth was chosen in order to improve the overall etch quality and to ensure that the microchannels do not collide with each other. The problem with this shallow microchannel depth arises during the anodic bonding procedure. Previous research has proven that microreservoirs 5 mm in diameter and 4 μm deep will not collapse during anodic bonding [38]. In theory, the microchannel aspect ratio (depth/width) should not be smaller than 0.001 for successful anodic bonding [43]. Since the chips fabricated in process B were only etched at 2.6 μm in depth, they only had an aspect ratio of 0.00052 at the microreservoirs. Therefore, during anodic bonding, one microreservoir collapsed and the theory was confirmed. Multiple trials yielded similar results to validate the microreservoir collapsing behavior. Moreover, the applied DC voltage was reduced in order to hinder the electrostatic attraction between the two substrates, but this parameter did not affect the collapsing behavior of the microchannels. Although process B did yield microchannels with acceptable channel walls, the etch depth was too shallow for bonding. Therefore, the process required enhancement before AFM nanolithography could be performed. Even though process B did not yield useful chips, it did reveal possibilities for future designs and techniques.

The Process B work is summarized by the following:
- Cr/Au masking layers were evaporated on Pyrex® glass 7740 with single nanometer control
- Photoresist remained attached to Au under BOE for at least 50 minutes with a 30 minute hard bake at 120° C.
- BOE etched Pyrex® glass 7740 with a Cr/Au masking layer faster in the lateral direction (approximately 2.7 times faster than the vertical direction)
- Microreservoirs etched 2.6 μm deep collapsed during anodic bonding Process C: The goal for process C was to utilize the collected knowledge from previous processes to design and fabricate a chip that incorporated electrical sensing capabilities. This process primarily integrated the same fabrication techniques described in Process B. The two main differences were a new design of microchannels/microreservoirs and the addition of microelectrodes. The microchannels/microreservoirs were re-designed in order to accommodate the shallow etch depth during anodic bonding and to increase the number of chips per wafer. The microelectrodes were fabricated on the chip for future biomolecule detection. The plan was to connect the microelectrodes with FIB-assisted Platinum (Pt) nanoelectrodes. In this work, nanoelectrodes were defined as Pt electrodes deposited by the FIB ranging from 25 nm-1000 nm. Re-designing the microchannel design in AutoCAD was not going to impose any major issues, but the micro/nano tandem pair of electrodes needed to be tested first by demonstrating a proof-of-concept experiment with already existing photolithography masks.

FIB Electrode Investigation: The proof-of-concept (POC) experiment was carried out to determine if 15 μm Au electrodes could be fabricated on a glass wafer and to determine if the FIB would indeed deposit a nanoelectrode directly on a glass chip. Previous research had demonstrated that FIB-assisted Pt nanoelectrodes could be applied on a Si wafer to connect microelectrodes [52]. Before the wafer was completely re-designed, it was pertinent to verify that the FIB would work properly on a glass substrate.

The mask used for this POC experiment was from a previous student and was designed to pattern a silicon wafer with Au microelectrodes for carbon nanotube alignment. It featured 12 different microelectrode geometries. The smallest microelectrodes were 15 μm with a 15 μm gap, creating a perfect proof-of-concept experiment for this work. When using a transparency mask, 15 μm was the smallest consistent feature size that was feasible at HiDEC. The Au electrodes were fabricated under the same processes as explained in process B. During this experiment, microchannels were not of any interest, so there was not a BOE step. The Cr/Au evaporation thicknesses needed to be precisely controlled this time. Step heights greater than 50 nm have been proven to yield unbonded areas during anodic bonding [41]. Therefore, the Cr and Au layers were controlled to 15 nm and 30 nm respectively. The Cr/Au wafer underwent the same photolithography steps explained in process B. This time, however, the Cr/Au was not acting as a masking layer. After photolithography, the unwanted Cr/Au and PR were etched away, leaving only the 45 nm thick microelectrodes.

The wafer was diced and cleaned with acetone, IPA, methanol, and DI water and taken to the FIB for FIB-assisted Pt deposition. The FIB used in this project was the FEI Nova Nanolab 200 at the NANO building under the guidance of Dr. Mourad Benamara. The possible accelerating voltage of electrons ranged from 200 V-30 kV. The voltage for ions ranged from 5-30 kV. The SEM resolution was 1.1 nm and the ion resolution was 15 nm [2]. The gas injection for the FIB metal deposition was trimethyl methylcyclopentadienyl-platinum ((CH3)3(CH3C5H4)Pt). The FIB software allowed the user to input the desired length, width, and thickness of the Pt nanowire. Next, the substrates for the POC experiment are investigated under the SEM for FIB Pt electrode deposition.

There are several problems that can happen when using a SEM or FIB on an insulating substrate such as Pyrex® glass. First, the image may appear clouded and hard to resolve due to the accumulation of electrons on the surface. Also, insulating substrates have the tendency to "drift" on the nanoscale while in the SEM. This drift can cause problems with controlling the FIB milling and deposition input parameters. Typically, the output parameters (the actual dimensions of the fabricated metal or channel) are different from the input parameters. The results would be more reliable on a silicon substrate.

Figure 21:
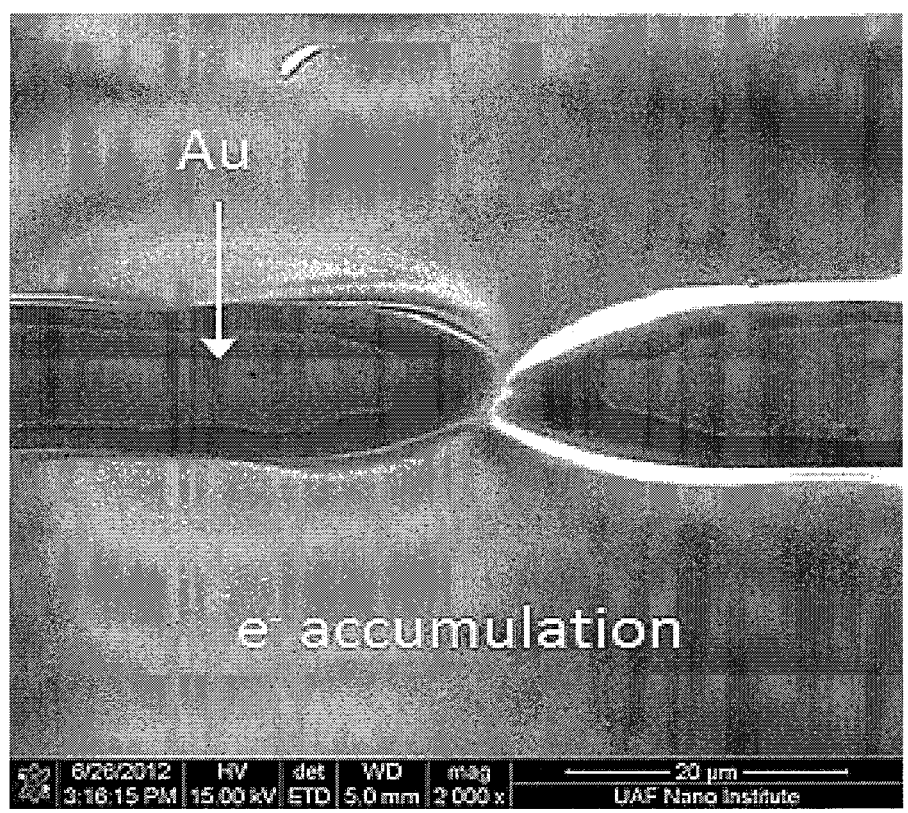
FIG. 21 is a SEM image of the proof-of-concept microelectrodes on glass.

Two Au microelectrodes, entering from the left and right, are displayed in the SEM image in FIG. 21. Charges had accumulated on the glass surface surrounding the Au microelectrodes and caused imaging problems. This was a common problem when viewing glass in a SEM due to its insulating nature. Although charge accumulation was inevitable for glass samples, it was reduced by grounding the sample with conductive tape. The Au microelectrodes from FIG. 21 were grounded to the metal sample plate, allowing electrons to flow freely. This explains why the image was clear only around the electrodes.

Figure 22:
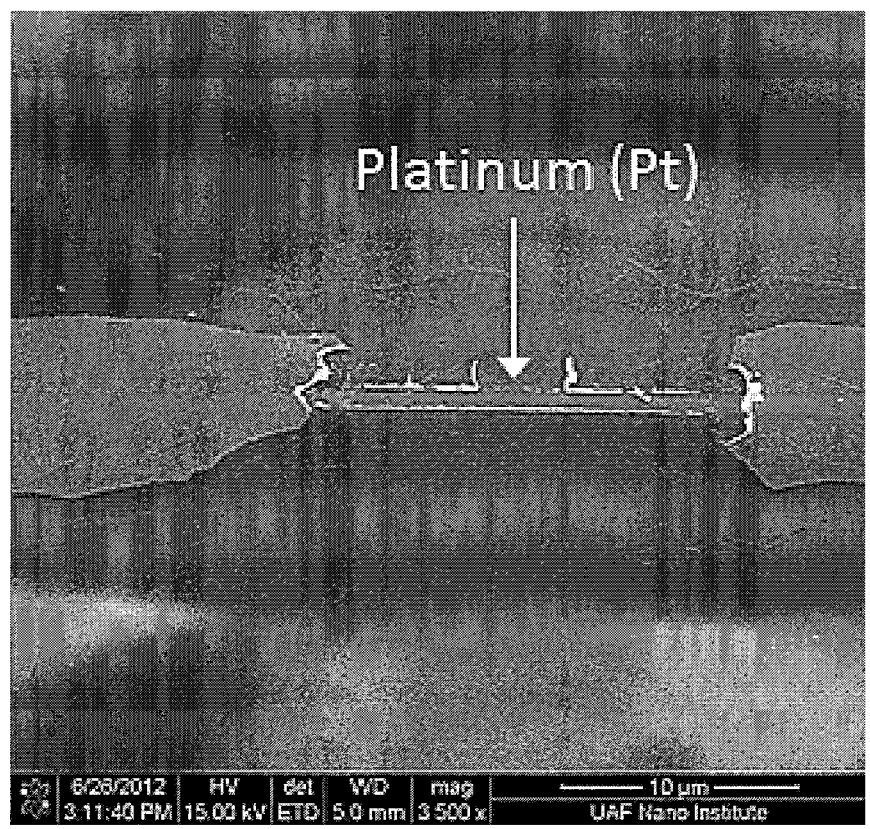
FIG. 22 is a SEM image showing the first FIB Pt deposition.
Figure 23:
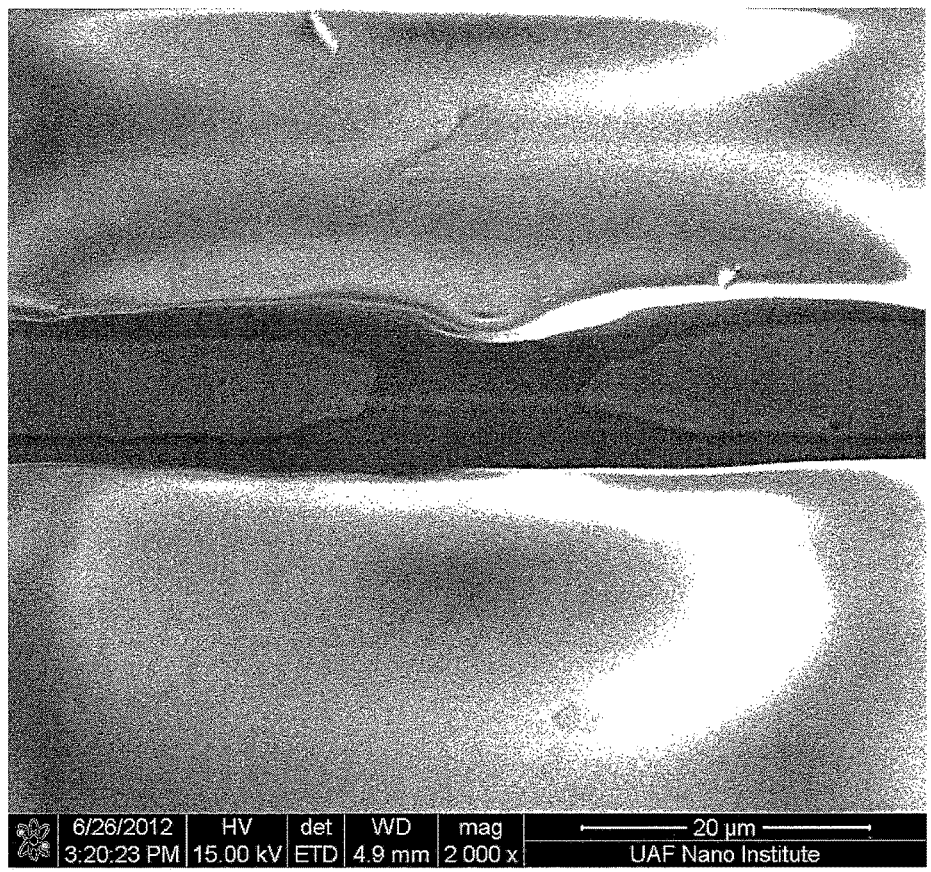
FIG. 23 is a SEM image showing the second FIB Pt deposition.

After the sample was loaded into the SEM and an initial image was taken, the FIB was used to deposit a Pt electrode between the microelectrodes. Since this was a proof-of-concept experiment, the first trial was to deposit a 1 μm wide electrode just to determine if this FIB would work on glass. The result is shown in FIG. 22. Although it was clear that the Pt electrode did indeed connect the two Au microelectrodes, the deposition was rough and the Pt appeared to be flaking or lifting off the surface of the glass. There also seemed to be drift effects, as the Pt electrode appeared to be wider than the input width of 1 μm. In order to improve the deposition quality, the input current was reduced from 50 pA to 30 pA. The voltage during deposition was 30 kV. Moreover, since the 1 μm wide electrode was deposited successfully, the second trial attempted to deposit an 800 nm Pt electrode. The idea was to start large (around 1 μm) and gradually decrease the Pt electrode width until it no longer showed successful contacts. The second attempt at FIB deposition is displayed in FIG. 23, and showed a much smoother deposition. The deposition was applied at 30 kV and 30 pA. The chip was removed from the SEM and checked for continuity with a multimeter. Although the deposition of the second Pt electrode still indicated that there was drift (the measured width of the Pt was about 2 μm), the contact was continuous. More detailed results of the FIB nanoelectrodes will be explained in the results and discussion section. This indicated that process C could be implemented and that the microchannels and microelectrodes could be re-designed and established on each device.

Figure 24:
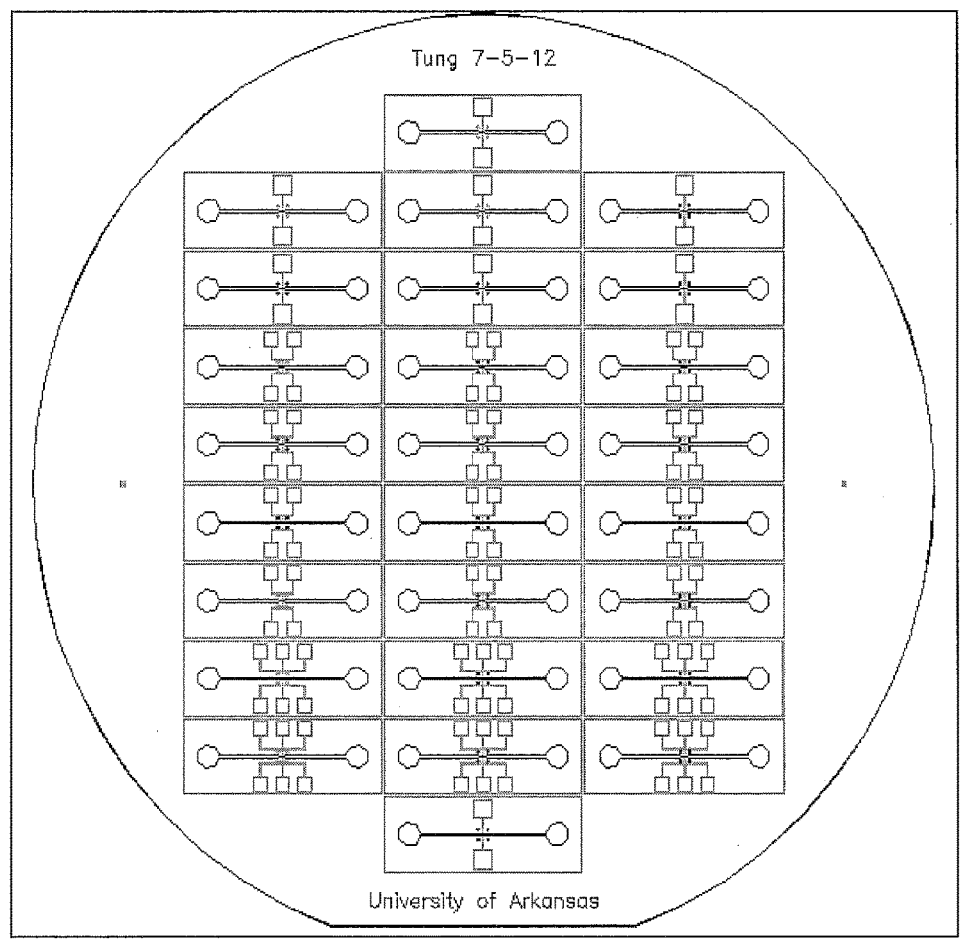
FIG. 24 is an electrode mask incorporating electrodes.

New Mask Design: After the proof-of-concept experiments proved that FIB-assisted Pt nanoelectrodes could be deposited on glass, the microchannel designs from process A and B had to be re-designed in AutoCAD. The design goals for this mask were to decrease the microreservoir diameter and to incorporate microelectrodes aligning the nanochannel region. FIG. 24 shows the outline of the new mask (electrode mask).

Figure 25:
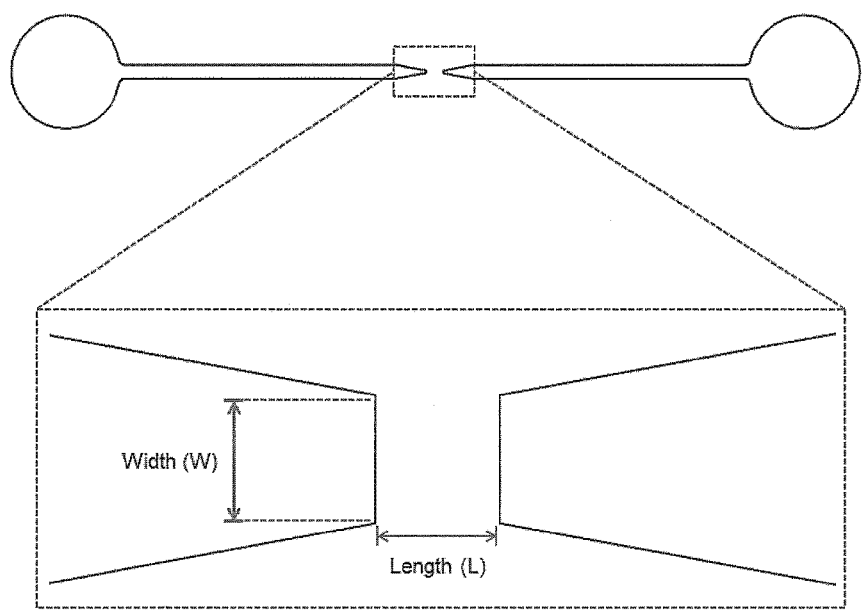
FIG. 25 is a schematic showing the labeling criteria of the nanochannel region.

This process called for two different photolithography steps. FIG. 24 shows the two masks aligned directly on top of each other. The patterns in black represent the microchannels, and the gold patterns represent the chip outline and the microelectrodes. The electrode mask exhibited several new features to be used for experimentation. First, this mask featured 26 chips, which was a 100% increase from the original design. Also, the microreservoirs were only 2.5 mm in diameter, which was a 50% decrease from the original design. This allowed the etch time to be cut in half and the overall microchannel etch quality to improve. Next, 15 μm wide microelectrodes aligned to the nanochannel region were added to the electrode mask at varying gap distances of 10, 15, and 20 μm. The nanochannel region dimensions varied from as small as 40×40 μm (W×L) up to 100×100 μm (W×L). The first number represents the width of the end of the microchannel, and the second number represents the distance from the end of one microchannel to the end of the other microchannel as shown in FIG. 25 below. Although some chips were designed to have 1 or 3 microelectrodes, the majority of them were designed with 2 microelectrodes. The chips with two microelectrodes were still capable of producing high fabrication yields and would allow for more accurate biomolecule detection. All adjacent microelectrodes were separated by 15 μm for higher fabrication yields. The final enhancement of the electrode mask was the smaller chip size. By decreasing the chip area from 375 mm² to 176 mm², the electrode mask was able to include twice as many more chips than the old mask. With the design of the new mask complete, the next step was fabrication.

Figure 26:
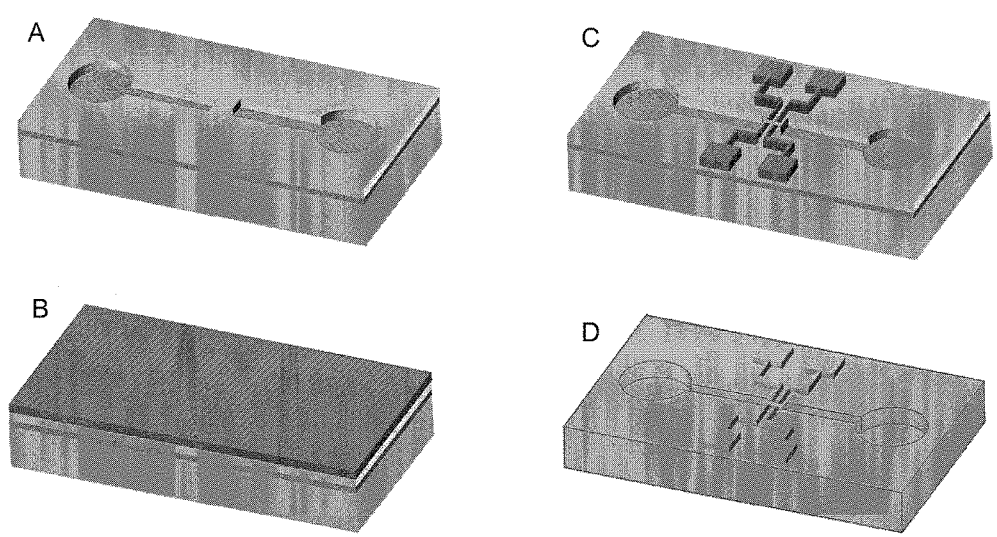
FIG. 26 is a microfabrication process flow for Process C.
Figures 27A, 27B:
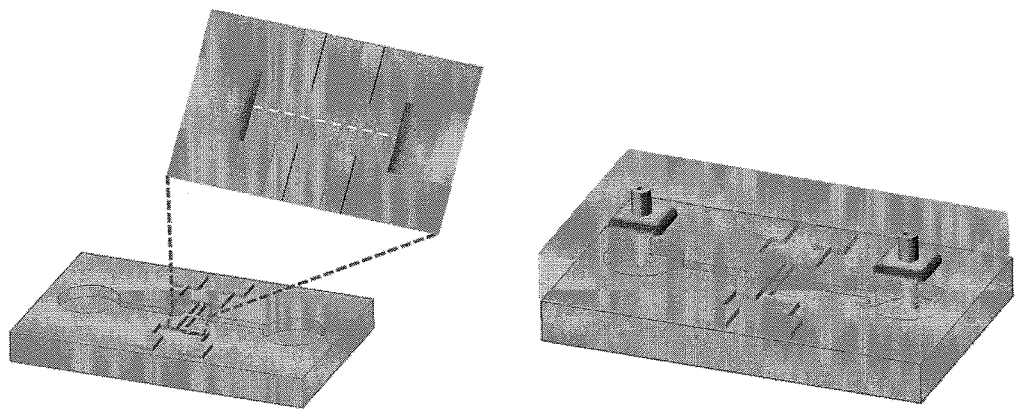
FIG. 27($a$) and FIG. 27($b$) illustrate a nanochannel formation (FIG. 27($a$)) and Pyrex® glass-Pyrex® glass packaging (FIG. 27($b$)).

Fabrication of Electrode Mask: The fabrication process for the new electrode mask (process C) remained close to that of process B. For instance, a Cr/Au masking layer was still needed as a mask for microchannel etching. The new use for the Cr/Au, however, was the in the addition of microelectrodes. The same Cr/Au metal layer used for the mask was also used for the microelectrodes. The microfabrication process flow for process C is shown in FIG. 26 below. The process was an extension from FIG. 15 (15 nm Cr and 25 nm Au). The microchannels were etched into the bulk of the substrate (A). Next, a second layer of PR was spread over the wafer (B). The electrode mask was used to pattern the wafer (C). All of the exposed PR and underlying Cr/Au was etched from the wafer (D). The next steps of the fabrication are displayed in FIG. 27. The microelectrodes were connected with Pt nanoelectrodes by FIB metal deposition and the nanochannel was realized in the perpendicular direction (left). Finally, the chip was packaged through anodic bonding (right). The investigation and evaluation of the FIB Pt nanoelectrodes and a new method for anodic bonding are discussed in Sections 2.3.4 and 2.3.6.

Figure 28:
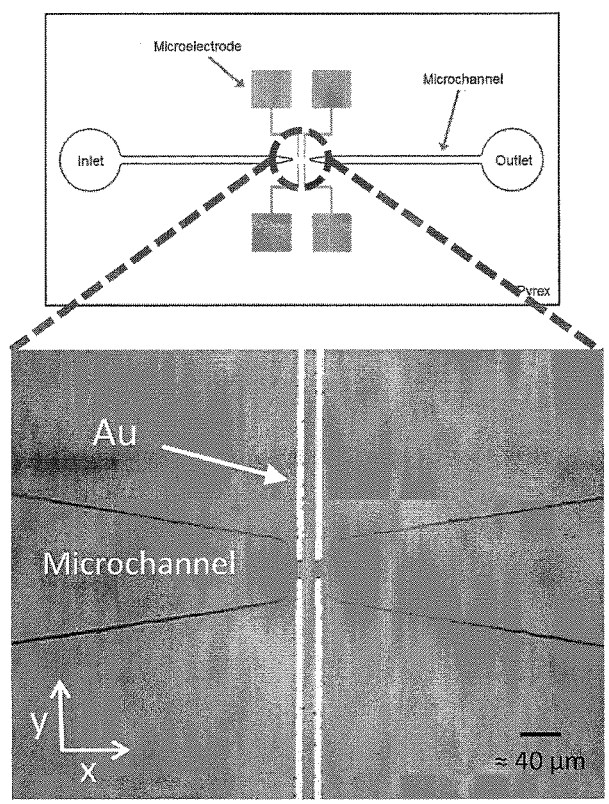
FIG. 28 is a top view of the nanochannel device.

FIB Pt Electrode Fabrication: After removing the undesired Cr/Au from the surface of the microchip, the top view of the device resembled FIG. 28 (the x-axis runs parallel to the channel and the y-axis runs parallel to the electrodes). From FIG. 28, it was clear that the microelectrodes and microchannels were discontinuous. Also, the microchannels' etch quality had improved drastically when compared to the first attempt explained in Process A. Before the nanochannel was realized, the microelectrodes were connected by FIB Pt deposition of the nanoelectrodes.

Figures 29A, 29B:
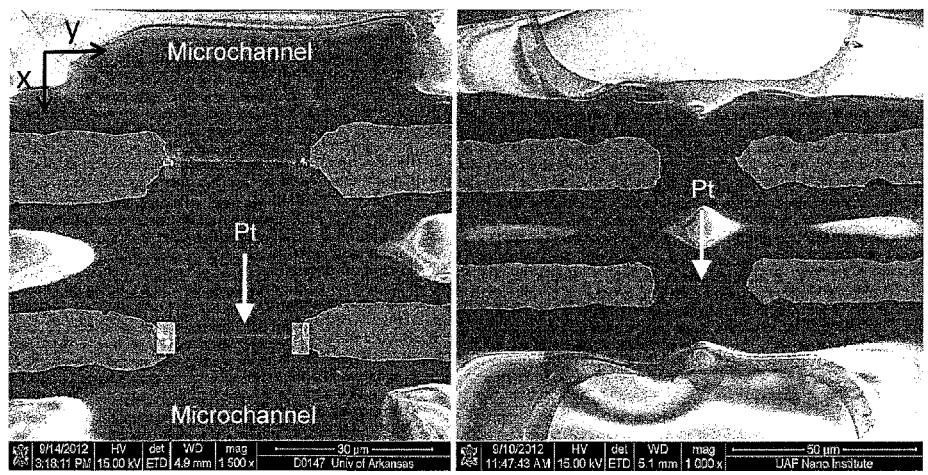
FIGS. 29($a$) and 29($b$) are SEM images of larger Pt nanoelectrodes with contact pads (FIG. 29($a$)) and small Pt nanoelectrodes without contact pads (FIG. 29($b$)).

The Au microelectrode gaps were filled with Pt through FIB deposition, with two examples displayed in FIG. 29. On the left, the input dimensions of the Pt nanoelectrodes were 700 nm×50 nm (width×thickness). On the right, the input dimensions were only 250 nm×50 nm. Moreover, it was noticeable that there were small Pt rectangular pads on the Pt—Au interfaces for the chip on the left. The thickness of the Cr/Au electrodes were ≈40 nm and the Pt electrodes were only ≈15 nm. Therefore, the Pt was deposited over a step height of ≈25 nm. The Pt pads were used in order to minimize edge defects or voids between the Au/Pt interfaces. As the nanoelectrode width decreased from hundreds of nanometers wide to just tens of nanometers wide, the resistance of the entire junction (including both Au microelectrodes and the Pt nanoelectrode) increased from the kΩ range to the MΩ range.

Figure 30:
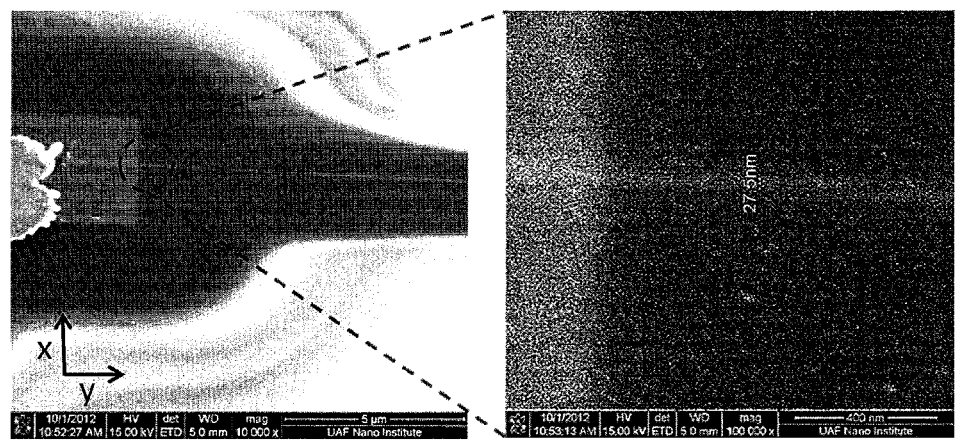
FIG. 30 is a SEM image of a small Pt nanoelectrode.

The output width (the width measured after deposition) of the Pt nanoelectrode was always greater than the input width. Likewise, the thickness of the nanoelectrode was always smaller than the input. This was likely a combined result of the FIB gun instability and the drift associated with the nonconductive substrate. Nevertheless, the smallest FIB Pt nanoelectrode that was fabricated is presented in FIG. 30. The input was 1 nm×25 nm and the output was around 25-30 nm wide and about 1 nm thick. This was essentially the smallest electrode that can be deposited on glass by using the FIB gun. Future improvements could possibly be made by applying more conductive tape to the sample to improve the grounding of the substrate, but it is doubtful that the width of the Pt nanoelectrode will reach single digit nm resolution using the FIB, especially since the ion resolution of the Nova is only 15 nm. After several chips were fabricated and had successful Pt nanoelectrode contacts, they were cleaned gently with acetone, IPA, methanol, and DI water. Once the dust particles and debris from deposition were removed, the chip was dried with $N_2$ and taken to the AFM for nanochannel scratching.

Figure 31:
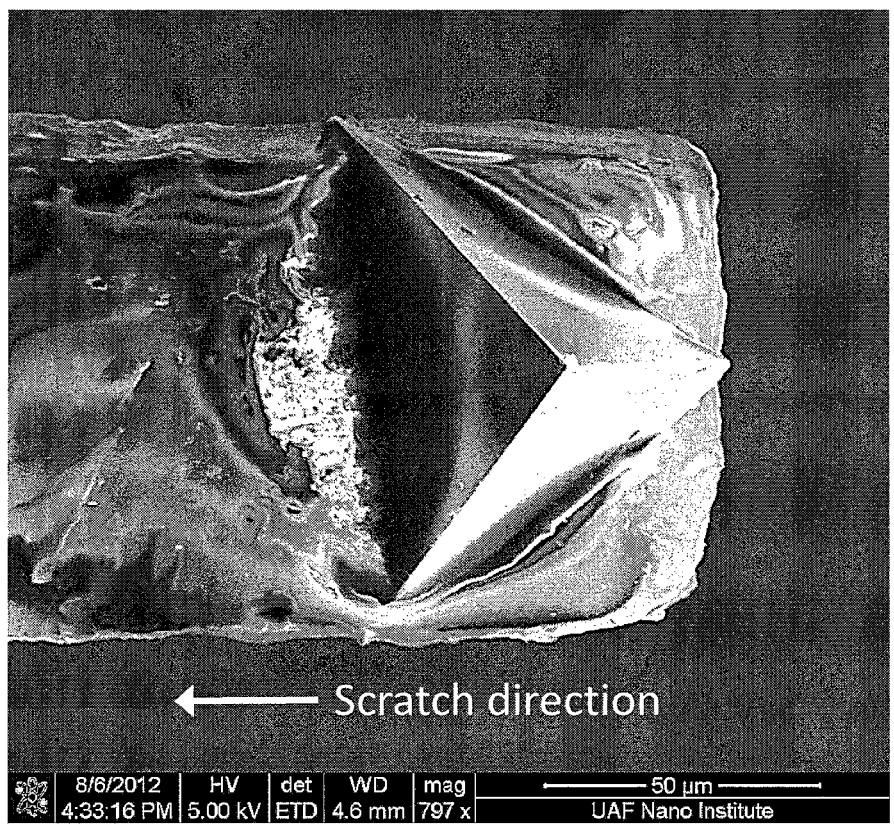
FIG. 31 is a SEM image of the Bruker DNISP all diamond AFM tip.

Bruker DNISP AFM Probe: As described in the introduction, AFM nanolithography is a new area of study in nanotechnology. Once the microelectrodes were connected using the Pt nanoelectrode(s), the chips were transferred to the AFM. The AFM for this research was the Agilent 5500 Atomic Force Microscope (0.1 nm vertical resolution) provided by Dr. Uche Wejinya. The cutting tool for this process was a Bruker DNISP AFM probe. The most noteworthy attribute about this type of probe was its all diamond tip which was mounted on a stainless steel cantilever as shown in FIG. 31.

This AFM probe had a spring constant of 222 N/m, deflection sensitivity of 212 nm/V, resonance frequency of 67 kHz, tip width and height of 100 μm×50 μm respectively, and a tip radius of 40 nm. The probe's input parameters were correlated to scratch dimensions before it was used on actual chips because it was brand new. The Agilent software allowed the user to input the scratch length, the number of scratches, the force setpoint, and the tip speed. For the correlation of the new tip, a constant setpoint voltage of 7 V was used. The setpoint range is typically between 0-10 V. The setpoint voltage can be related to the force exerted by the AFM tip normal to the sampling surface by the following equation, $$F = kDS \qquad \text{Equation 3}$$

where F is the force (N), k is the spring constant (N/m), D is the deflection sensitivity (m/V), and S is the setpoint voltage (V). Therefore, a setpoint voltage of 7 V resulted in a force of approximately 330 μN.

For the correlation of the new tip, the depth and width of the nanochannels were measured and compared to the number of cut cycles that were executed. The nanochannel profiles in FIG. 32 were generated by the Agilent software PicoView 1.12. The AFM probe scratched over the surface 1, 2, 3, and 4 times and the resulting nanochannels are shown respectively in FIG. 32A. In FIG. 32B, the cross-sectional geometry of a nanochannel is represented on a 1:1 scale, showing a more accurate representation of the nanochannel width than in FIG. 32A.

Figure 32A:
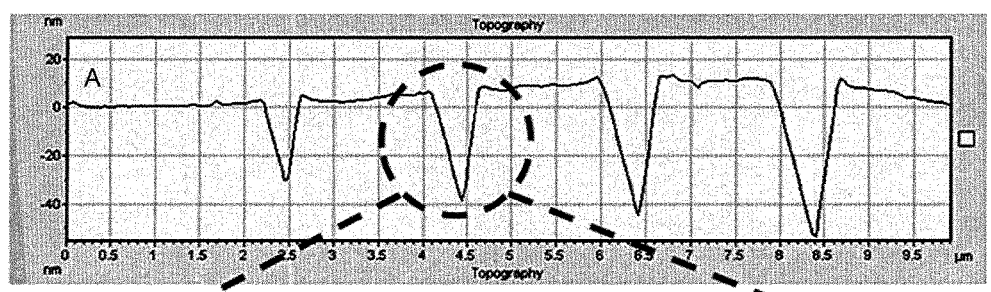
FIG. 32($a$) is a cross-sectional side view of AFM probe correlations and FIG. 32($b$) is a detailed view of a single nanochannel with 1:1 scaling.
Figure 32B:
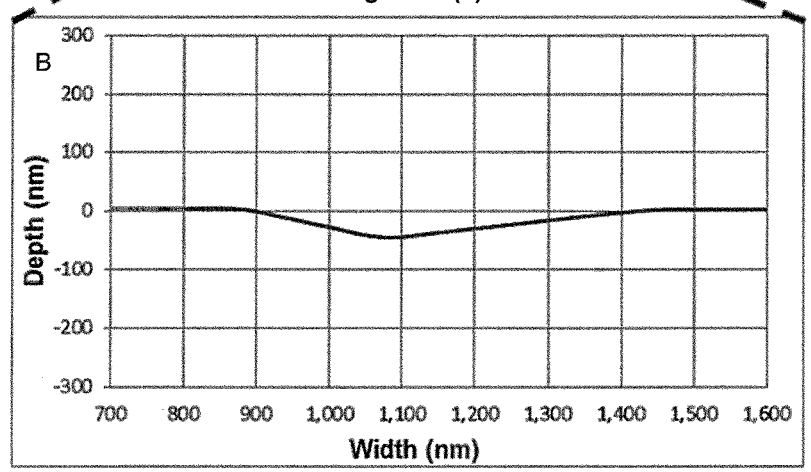
Figure 33A:
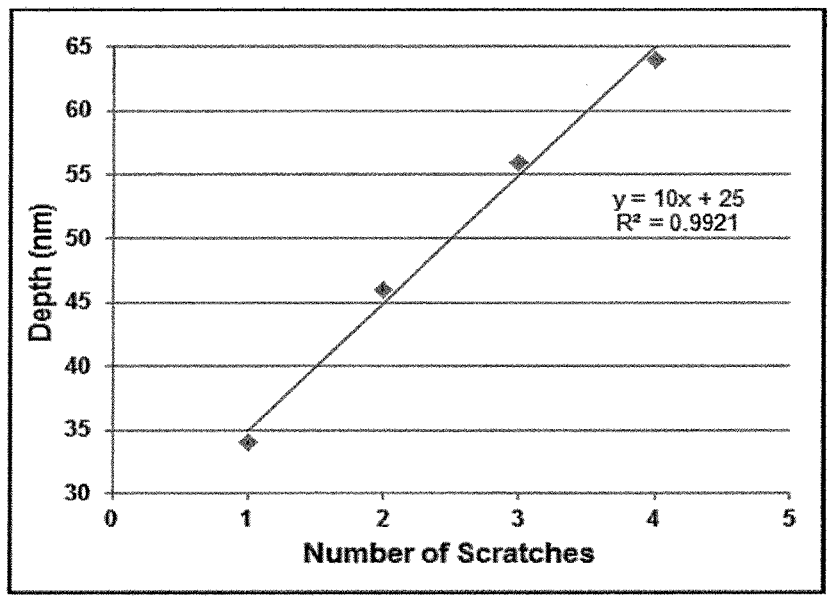
FIG. 33($a$) and FIG. 33($b$) are AFM correlations for depth (FIG. 33($a$)) and width (FIG. 33($b$)) of the nanochannel vs. the number of scratches.
Figure 33B:
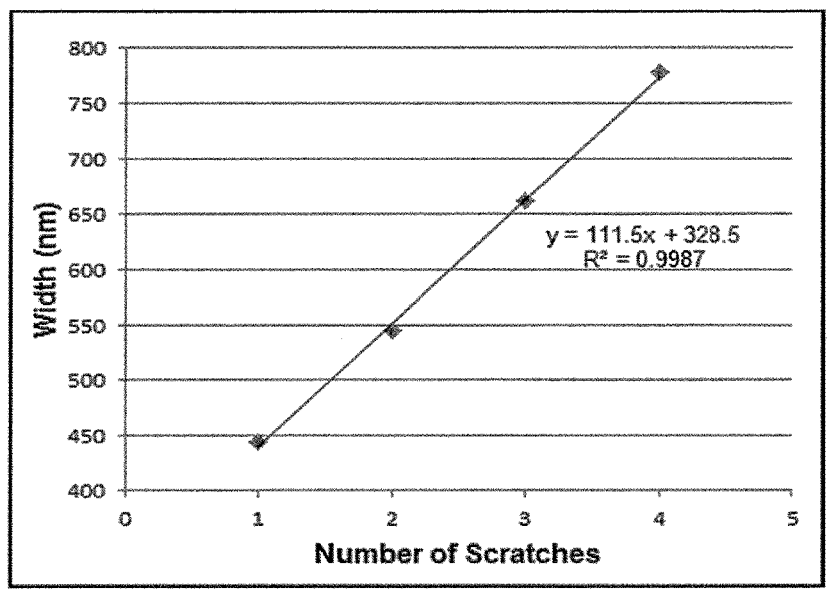

The AFM nanolithography correlations from the data gathered in FIG. 32A is represented in FIG. 33. Each data point represents a single sample. The linear relationship of both of these correlations (width and depth) was in agreement with previous research on AFM nanolithography [38]. The tip was strong enough to cut a 35 nm deep by 450 nm wide nanochannel with just one scratch. The aspect ratio (12:1 width: depth) of this nanochannel is about 6 times larger than the microscale aspect ratio of the DNISP tip (2:1). This difference was possibly due to the roundness of the tip at the nanoscale.

Figure 34:
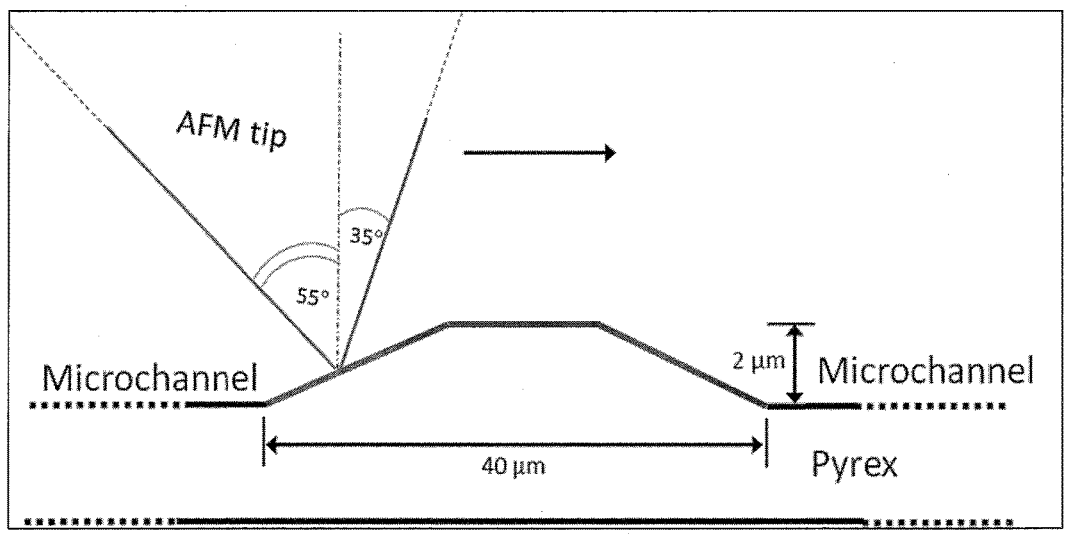
FIG. 34 is a schematic of the cross-sectional side view of the nanochannel region during AFM scratching.
Figure 35:
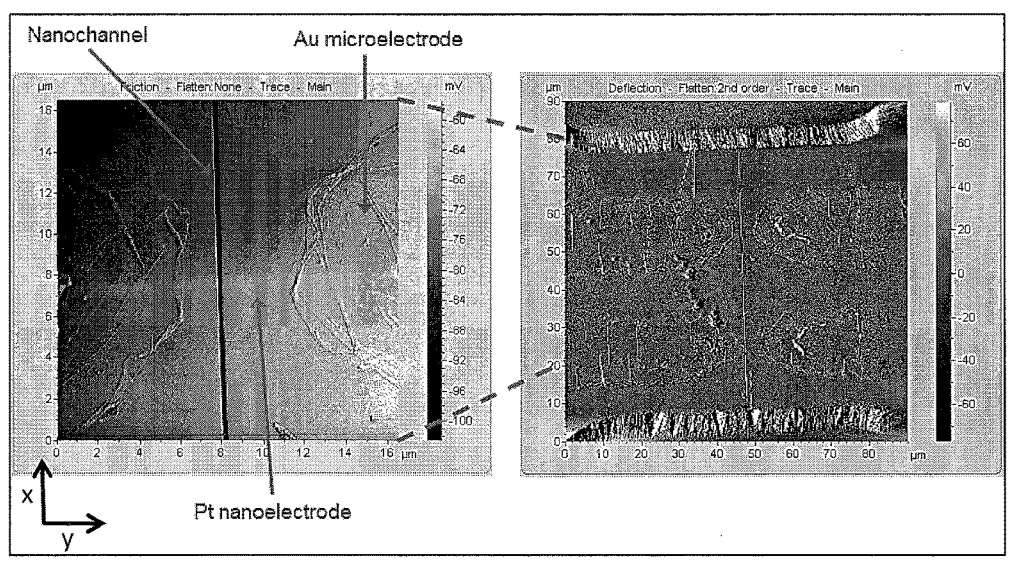
FIG. 35 is an AFM scan of the nanochannel region after AFM nanolithography.

Because the DNISP probe is robust, it can be used to cut on complicated surface topographies, such as the sloped edge displayed in FIG. 34. This sloped edge represents the nanochannel area during scratching. Due to the isotropic nature of the BOE, the AFM probe was forced to climb up a sloped channel wall first, continue scratching on a flat surface, and then finish by traveling down the other sloped channel wall. The first actual scratch with the DNISP probe is shown in FIG. 35. On the right, the scan area represents the entire nanochannel region with the microchannels located at the top and bottom. There are two Au microelectrodes entering both from the left and right of the scan. The scan area on the left of FIG. 35 represents a detailed scan of the Au microelectrodes, Pt nanoelectrode, and the vertical nanochannel. The DNISP successfully cut through the Pt nanoelectrodes and scratched a nanochannel simultaneously with just one scratch. After successful nanochannel formation, the chip was ready to be capped through anodic bonding.

Figure 36:
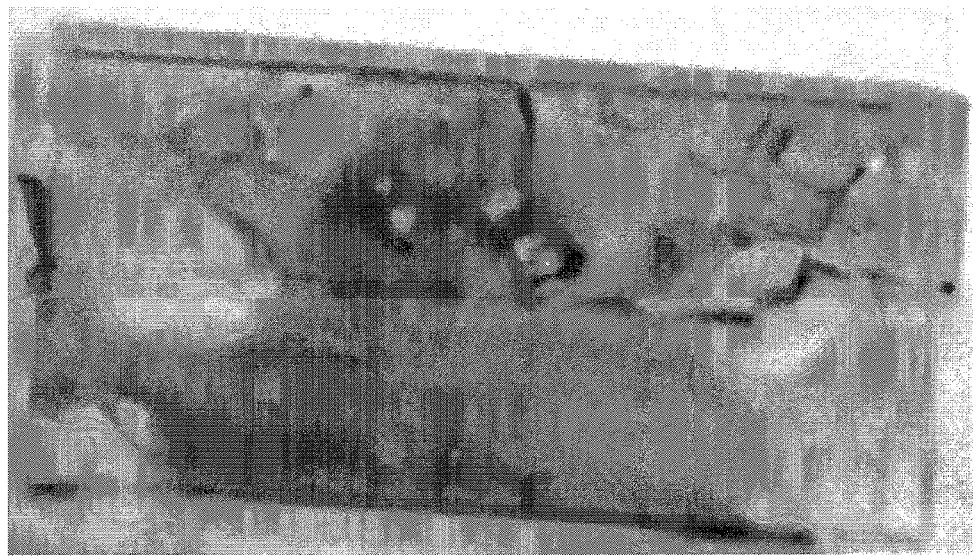
FIG. 36 is an image of a failed Pyrex® glass-soda lime glass bond.
Figure 37:
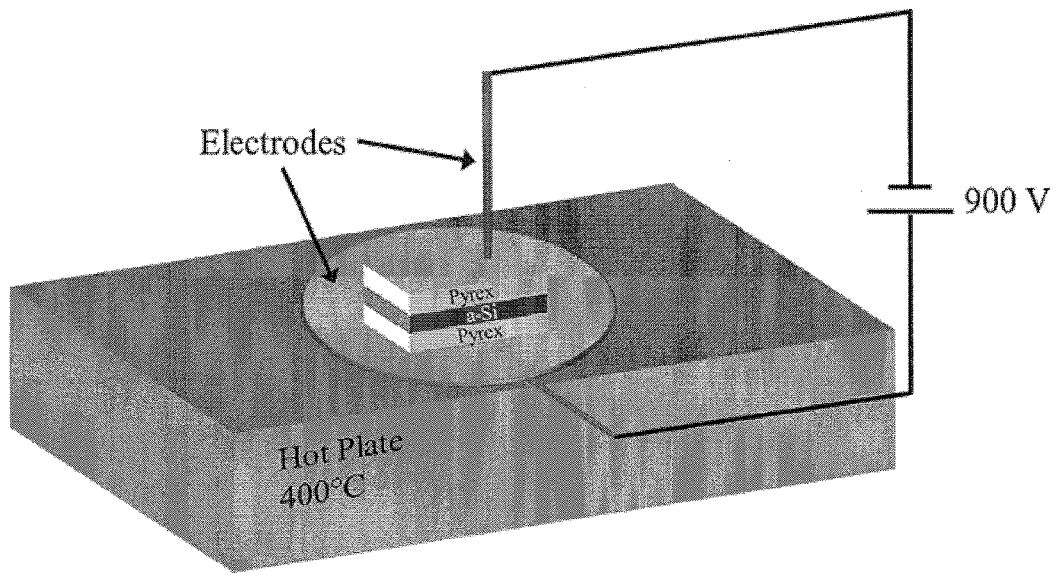
FIG. 37 is a schematic illustrating Pyrex® glass-Pyrex® glass anodic bonding.
Figures 38, 39:
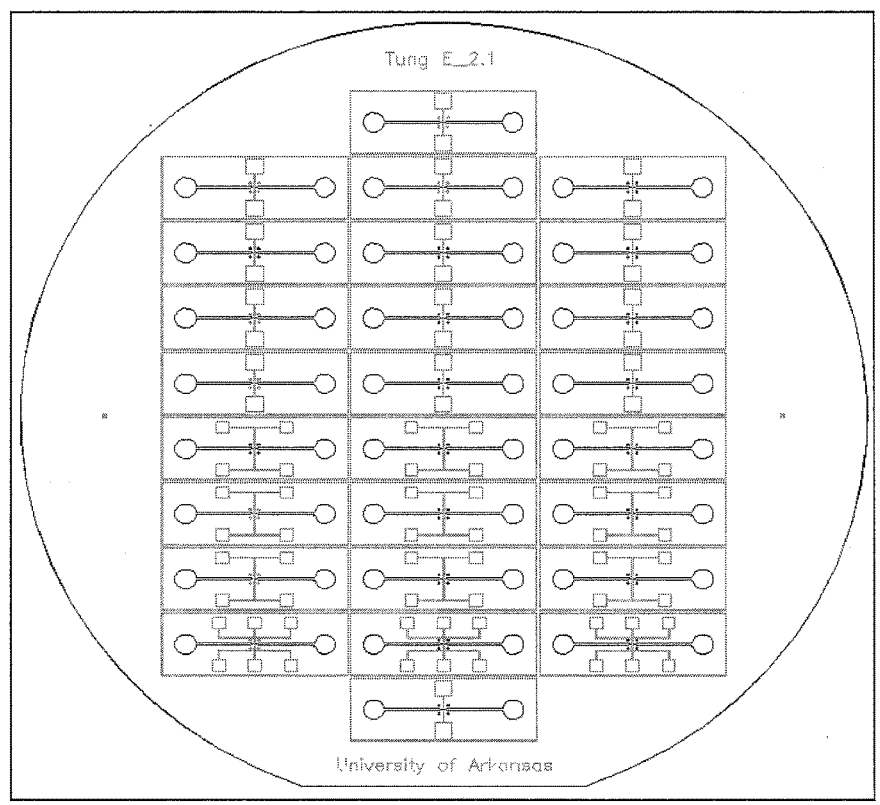
FIG. 38 is an image of transparent nanofluidic device
FIG. 39 is an AutoCAD mask design for Process D.

Amorphous Silicon Capping Piece: In addition to Process C incorporating Pt nanoelectrodes and the new DNISP AFM probe, there was also an enhancement to the anodic bonding process. For more efficient optical microscopy, a transparent device is ideal. Therefore, the silicon capping chip was replaced with a glass chip that had a thin layer of amorphous silicon (a-Si) deposited on top. Since a-Si is transparent, it can be deposited on top of a glass chip by plasma enhanced chemical vapor deposition (PECVD), be bonded to Pyrex® glass via anodic bonding, and create a transparent device. As displayed in FIG. 36, a 100 nm thick layer of a-Si was first deposited on soda lime glass and then bonded at 450° C. and 1000 V DC. The device was properly bonded after only 20 minutes, but it shattered when it was removed from the hot plate to cool down. This proved that soda lime could not be used as the capping piece due to its high coefficient of thermal expansion of 9 μm/m-K compared with that of a-Si and Pyrex® glass, which is only about 4.0 μm/m-K [53-55]. Therefore, the new bonding procedure, as displayed in FIG. 37, was between two Pyrex® glass chips with a thin a-Si intermediate layer. This new process resulted in a transparent device, which enhanced optical microscopy. One of the bonded devices is shown in FIG. 38, and the words on the paper underneath the device are clearly visible. For the first time, the nanofluidic device could be visualized underneath an optical microscope in any orientation. This became handy when viewing the microchannels under the microscope when fluidic connectors had been attached to the inlet and outlet of the device.

Fluorescent Dye Preparation: Once the devices fabricated by Process C were capped through anodic bonding, they underwent DI water flow tests and fluorescein isothiocyanate (FITC) flow tests. FITC is a powdery, non-toxic hydroxyxanthene dye that generates a vibrant green fluorescence in slightly acidic to alkaline solutions (PH>5) [56]. FITC flow tests were performed in order to analyze the patency of the nanochannels and, more importantly, the quality of the anodic bond. Prior to the flow tests, the FITC solution was prepared in the following procedure:

1. Place 1 mg of Fluorescein in a centrifuge tube
2. Add 1 ml of 100% ethanol to the centrifuge tube
3. Use the Vortex Touch Mixer model 232 to mix the solution
4. Centrifuge for 1 minute using the Sorvall Biofuge Primo centrifuge at 13,000 RPM
5. Remove the supernatant from the centrifuge tube
6. Dilute the solution with DI water to 25×

The detailed results of the DI water and FITC flow tests are defined in the results and discussions section.

Failures of Process C: There were a few problems that were solved during Process C (the addition of microelectrodes and Pt nanoelectrodes), but some new problems also became apparent. First, the Pt nanoelectrodes started failing during various cleaning steps between the FIB deposition and anodic bonding. The chips were typically cleaned in a piranha solution (3:1 $H_2SO_4$:30% $H_2O_2$) at 100° C. prior to bonding. This step caused the Pt nanoelectrode to become discontinuous. After looking into the instability of the Pt nanoelectrodes in more detail, simply cleaning the chips with solvents and drying with $N_2$ would sometimes break the Pt nanoelectrodes as well. Even placing them on the hot plate around 400° C. for 15 minutes would cause the Pt to fail. In general, Pt nanoelectrode chips with FIB inputs less than 250 nm wide×50 nm thick were too fragile to process. Therefore, the remainder of this research contains chips with Pt nanoelectrodes between 500-1000 nm in width.

The second problem was that the lengths of the nanochannels were too long for rapid flow testing. Process C generated chips with nanochannels that ranged from 30-85 μm in length. Some of the shorter nanochannel devices did show successful flow patency of the nanochannel (these chips are discussed below), but the longer nanochannel devices were incapable of fluid flow. Based on the following standard pipe flow equation, $$\Delta P = \frac{8\mu L Q}{\pi d^4} \qquad \text{Equation 4}$$

where P is the pressure, μ is the dynamic viscosity, L is the length, Q is the volumetric flow rate, and d is the diameter of the pipe, it is true that P∝L. Therefore, by creating a new chip design with lengths less than 30 μm or more would allow for more efficient flow testing in the future.

Process D: New AutoCAD Design: The main goal of process D was to redesign the mask in order to allow for shorter nanochannels. The push was for the nanochannels to reach approximately 5 μm in length. The use of transparency masks coupled with the capabilities of the Karl Suss aligner at HiDEC meant that the minimum feature size of the mask could only be 15 μm. This minimum feature size was an approximation based off of previous fabrication at HiDEC with transparency masks. The new mask design is displayed in FIG. 39 (the 3D microfabrication process flow of Process D is not displayed because it was similar to Process C). From this view, the only noticeable difference between this design and the one for Process C is the placement of the bonding pads for the two and three microelectrode configurations. By spacing out the bonding pads on these chips, the packaging of the device was much more efficient. FIG. 40 shows the comparison between the single (top), two (middle), and three (bottom) electrode design. The major difference between these two designs resided in the nanochannel region. For the single electrode configuration, FIG. 41 shows the difference between Process C and Process D. Before, the microelectrodes were designed to come close together and penetrate the area in between the microchannel walls. This allowed the FIB to make relatively short (approximately 15 μm) Pt nanoelectrodes and would give the user more control over the dimensions. However, this design inadvertently increased the distance between the microchannels to at least 45 μm (the minimum width of the microelectrode plus 15 μm on each side for spacing).

Figures 42A, 42B:
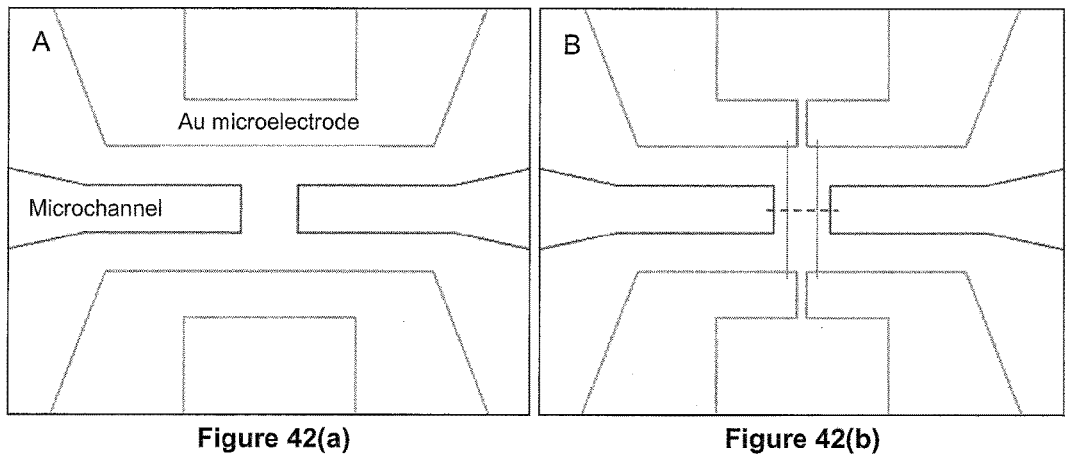
FIG. 42($a$) illustrates continuous Au microelectrodes before FIB milling and FIG. 42($b$) shows the Au microelectrodes connected to Pt nanoelectrodes.

The two electrode configuration is shown in FIG. 42. For Process C, they were designed to come close together and penetrate the nanochannel area. It was apparent that the microchannel gap was dependent on the number of electrodes incorporated on the chip. The most beneficial feature of the new Process D design was that the microchannel gap did not depend on the number of electrodes present due to the help of FIB milling. For the two electrode configuration, the Au microelectrodes on each side of the microchannel were continuous, which was different from the old design. FIG. 42A shows the continuous Au microelectrodes before FIB milling. The FIB was used as a sputtering tool in order to cut a trench (500 nm wide×100 nm deep) through the Au microelectrodes to make them discontinuous, as demonstrated in FIG. 42B. This left the Au dissected by the ion beam and each bonding pad was electrically isolated. The next step was to connect the Au microelectrodes with Pt nanoelectrodes. This step is also demonstrated by FIG. 42B as small vertical lines. Finally, the nanochannel was realized and connected the microchannels, as indicated by the red dashed line.

Fabrication Process: The microfabrication of chips for this process was similar to that of Process C. The major difference was that a new PR was used for Process D. For the first time, AZ4110 PR was spun on the Au at 1.25 μm thick (as opposed to AZ4330 PR spun around 4 μm thick for Process C). This thinner PR was used in order to increase the yield of the wafer. Since this new design really pushed the limitations of the Karl Suss aligner (minimum feature size of ≈15 μm), a thinner PR would improve the quality of patterning the wafer. Just as this new design was nearing its end of fabrication at HiDEC, the AFM large scanner was broken, and therefore, nanolithography was no longer usable for nanochannel formation. The quickest recovery plan was to use the FIB milling feature to realize nanochannels in the future. Before this process could be used on actual devices, the FIB gun had to be correlated on a Pyrex® glass substrate.

FIB Milling Correlations: Just as the new DNISP AFM probe was correlated for Process C, the FIB milling process had to be correlated. The correlation was performed by etching four nanochannels in a Pyrex® glass substrate. Each nanochannel had its own unique input dimensions. The output dimensions were compared to the input for each nanochannel. The nanochannel input parameters, in nanometers (width×depth), were 100×40, 200×80, 300×120, and 400×160. The chip was taken to the AFM after FIB milling for characterization. Although the large scanner (90×90 μm scanning area) of the AFM was broken, the small scanner (10×10 μm scanning area) was still in good use.

Figure 43:
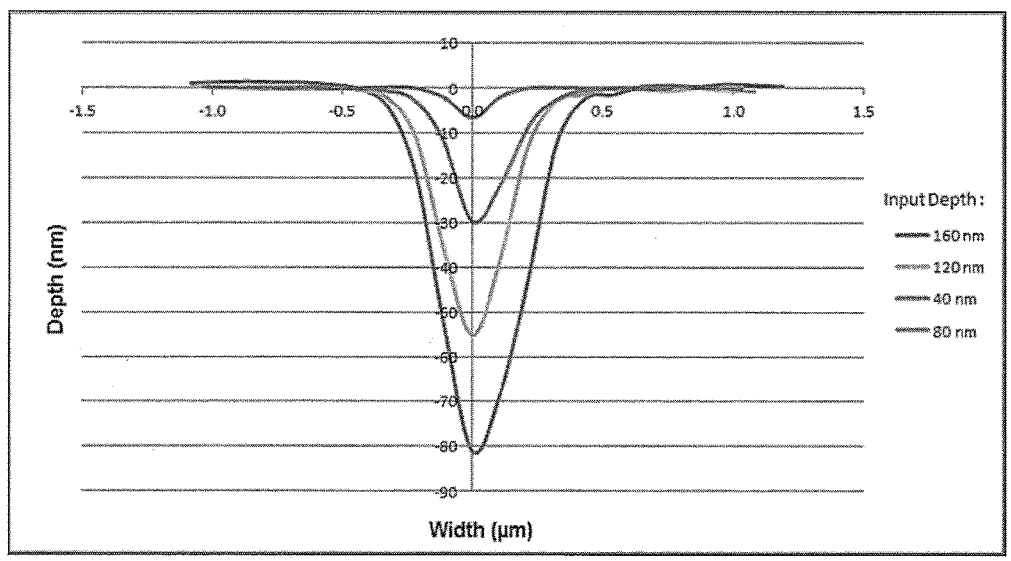
FIG. 43 is a cross-sectional side view of the four nanochannels etched by the FIB in the correlation experiment.
Figure 44A:
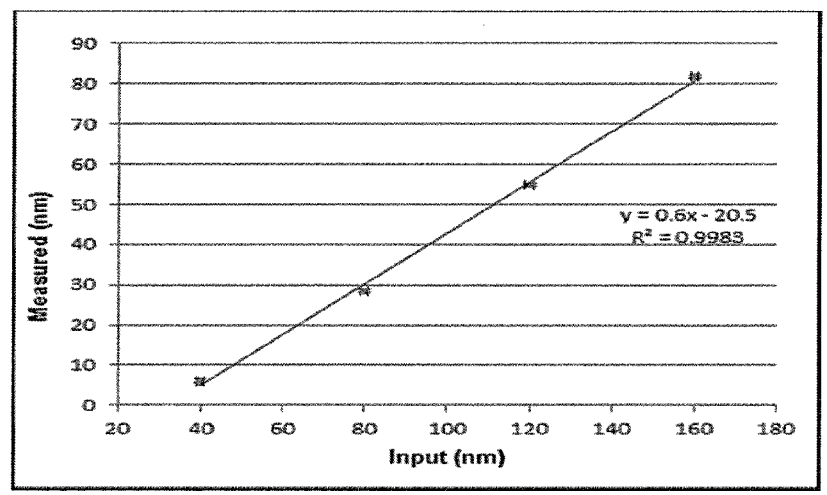
FIG. 44($a$) and FIG. 44($b$) illustrate the FIB milling correlation of the depth (FIG. 44($a$)) and the width (FIG. 44($b$)) of nanochannels.
Figure 44B:
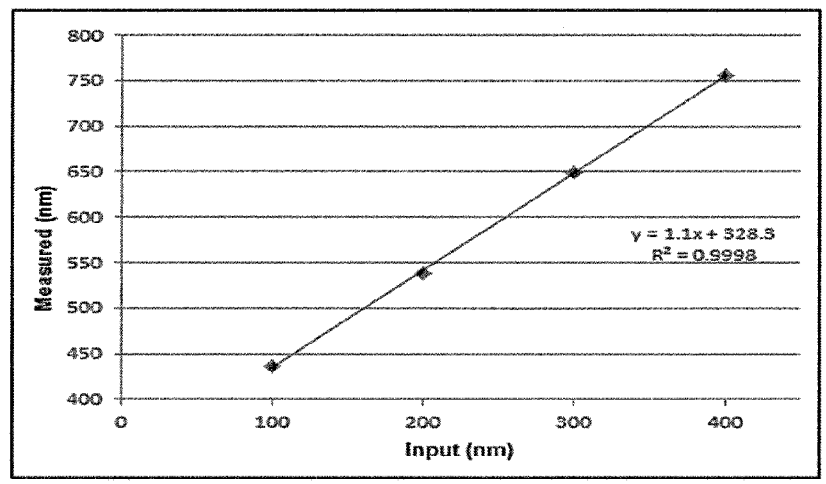

The FIB-milled nanochannels were scanned under the AFM and their cross-sectional side view profiles were overlapped and represented in FIG. 43. After analysis, it was discovered that the output depth was smaller than the input and that the output width was larger than the input for all four nanochannels. In addition, the output dimensions—both the depth and width—of FIB-milled nanochannels increased linearly with the input dimensions as displayed in FIG. 44. The linear relationship was helpful when making estimates or projections about the nanochannel dimensions. Each data point represents a single sample. The slope of the depth correlation indicates that the nanochannel gets 0.6 nm deeper for every 1 nm that is commanded by the input. The slope of the width correlation indicates that the etched nanochannel grew 1.1 nm wider for every 1 nm commanded by the input.

In similarity to the AFM nanolithography profile, the FIB milled nanochannels were much wider than deep, as displayed in FIG. 45. As shown in FIG. 45B, the FIB milled nanochannel edges were curved as opposed to squared. This is most likely due to re-deposition of the etched substrate.

The Fabrication Materials and Methods section focused on the continuous improvement of the design and fabrication of the nanofluidic device. There was an improvement in the design between the original mask and the mask from Process C. Moreover, there were additional improvements in the design between Process C and Process D. The actual devices and their quantitative results will be presented and discussed below.

Results and Discussions: This section contains SEM images of some of the fabricated devices and all of the experimental results obtained by testing the performance of the nanofluidic system. In addition, this Section discusses flow tests that were performed to chips fabricated from both Process C and Process D. Electrical measurements made to verify the behavior of Pt nanoelectrodes and nanobeads translocated through the nanochannel are also discussed.

Figure 47:
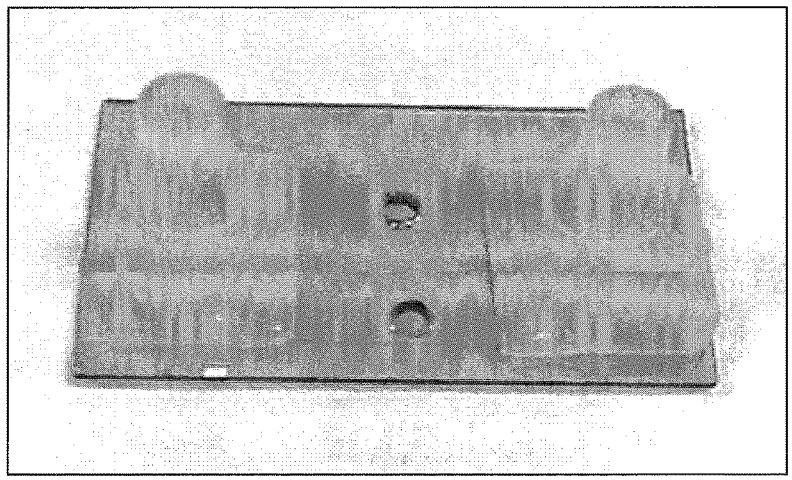
FIG. 47 is an image of a packaged single-electrode nanofluidic device.

FIB-milled Nanofluidic Device: Since the FIB was previously characterized and proven to etch nanochannels in a controllable fashion, it was used to create the nanochannels. Devices were fabricated in order to prove that the new design explained in Process D was successful (Pt nanoelectrodes could detect fluid and fluid could be pumped/translocated through the nanochannel). Therefore, larger nanochannels and nanoelectrodes dimensions were used (hundreds of nanometers up to 1 μm). FIG. 46 contains SEM images of the new design after fabrication. The microchannels are extremely close together in these pictures, resulting in a short nanochannel. In FIG. 46A, the nanochannel length was only ≈3 μm, while it was ≈6 μm in 46B. The lateral etch rate experienced by these chips was 0.4 μm/min. The chips were designed to be etched for 15 minutes. After etching was complete, each microchannel wall had been etched approximately 6 μm in the horizontal direction. This was what caused the microchannel gap to be reduced from 15 μm to just 3 μm. The microchannel gap for the chip in FIG. 46B was designed to be 18 μm instead of 15 μm, which explains why its nanochannel length was 6 μm. The nanochannel in FIG. 46A was supposed to be 550 nm wide×200 nm deep±1 nm. Based on the correlation results, the nanochannel was assumed to be 910 nm wide×107 nm deep±1 nm. The actual depth was never measured with the AFM. The chip was taken directly from the FIB to be packaged and tested. FIG. 47 is a picture of a packaged single electrode device.

Figures 48A, 48B:
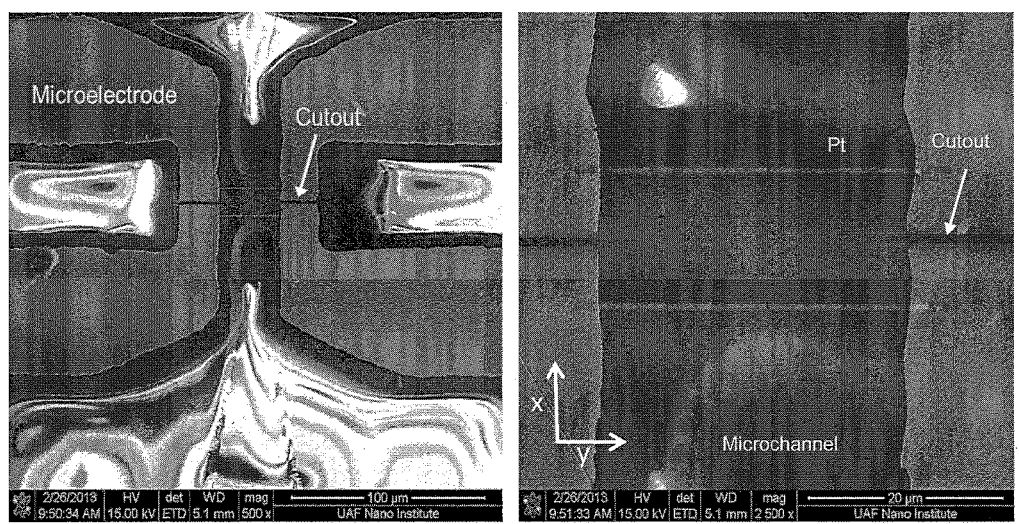
FIG. 48($a$) and FIG. 48($b$) are SEM images of a two electrode configuration chip.

In addition to the single electrode chips, double electrode chips were fabricated as a demonstrational proof-of-concept. FIG. 48 shows SEM images of a fabricated two electrode chip. The "cutout" represents where the FIB etched the Au to create independent microelectrodes. The picture on the right shows the horizontal Pt nanoelectrodes after being cut by the vertical nanochannel. The Pt nanoelectrodes were approximately 500 nm wide and 50 nm thick. Another device similar to this one was fabricated without a nanochannel. Resistance measurements were probed across both pairs of bonding pads to verify that the "cutout" successfully separated the Au microelectrodes. In this study, the two continuous Pt/Au electrodes had resistance values of 11.7 kΩ and 12.3 kΩ, respectively. This proved that the design described in Process D was valid, and that multiple electrode configurations can be demonstrated while keeping the nanochannel length in the single digit micrometer range.

Figure 49A:
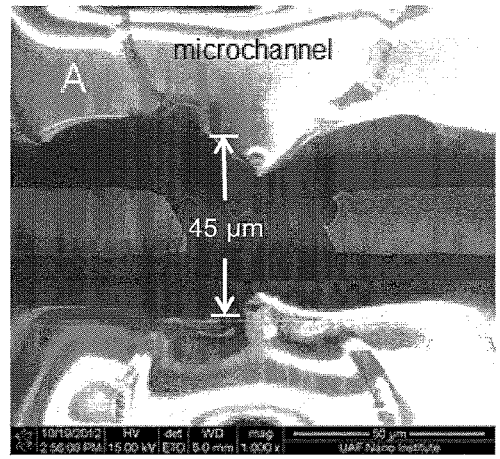
FIG. 49($a$) and FIG. 49($b$) are SEM images comparing the Process C design (FIG. 49($a$)) and the Process D design (FIG. 49($b$)) with a single electrode configuration.
Figure 49B:
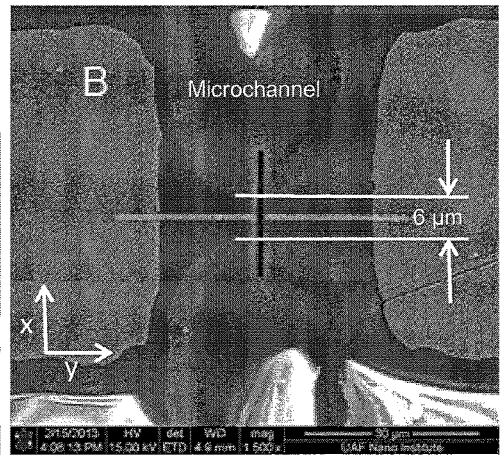
Figure 50A:
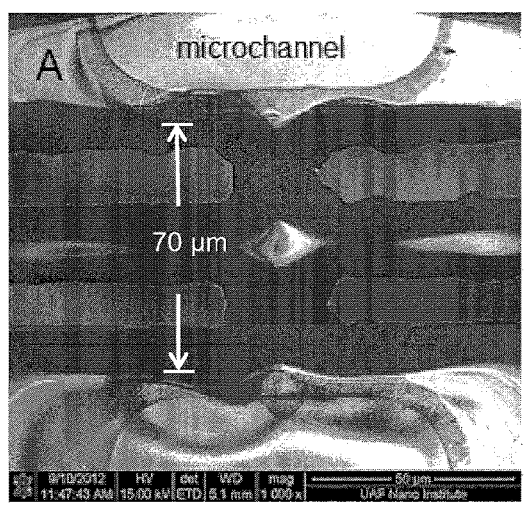
FIG. 50($a$) and FIG. 50($b$) are SEM images comparing the Process C design (FIG. 50($a$)) and the Process D design (FIG. 50($b$)) with a single electrode configuration.
Figure 50B:
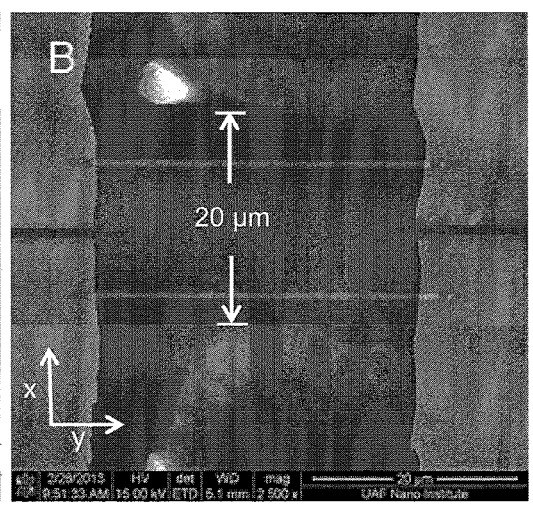

A comparison of Process C and Process D is displayed in FIG. 49 for the single electrode configuration. In FIG. 49A, the Pt nanoelectrode was too small to be seen and there was no nanochannel, but the focal point was the distance between the microchannels. By direct comparison, the microchannel gap was decreased from around 45 μm to about 6 μm, an 86% decrease. The benefits of having a shorter microchannel gap will be discussed in more detail below. In addition, the two electrode configuration is compared in FIG. 50. For this scenario, the microchannel gap was decreased from around 70 μm to about 20 μm, a 71% decrease.

Figure 51:
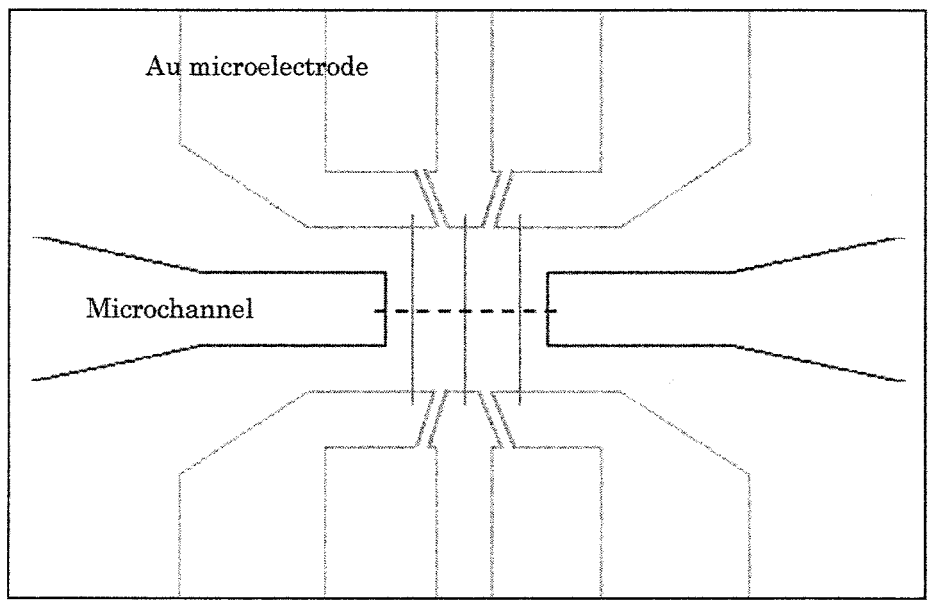
FIG. 51 is a schematic of a three electrode chip with Process D fabrication.

Although it was not demonstrated, this same strategy can be used for a chip with three electrodes, as shown in FIG. 51. For this process, the FIB gun would make two cuts on each side of the microelectrodes, eventually creating six independent microelectrodes. Then, Pt deposition and nanochannel formation will follow as usual. Each wafer for Process D included three chips like this.

Figure 52:
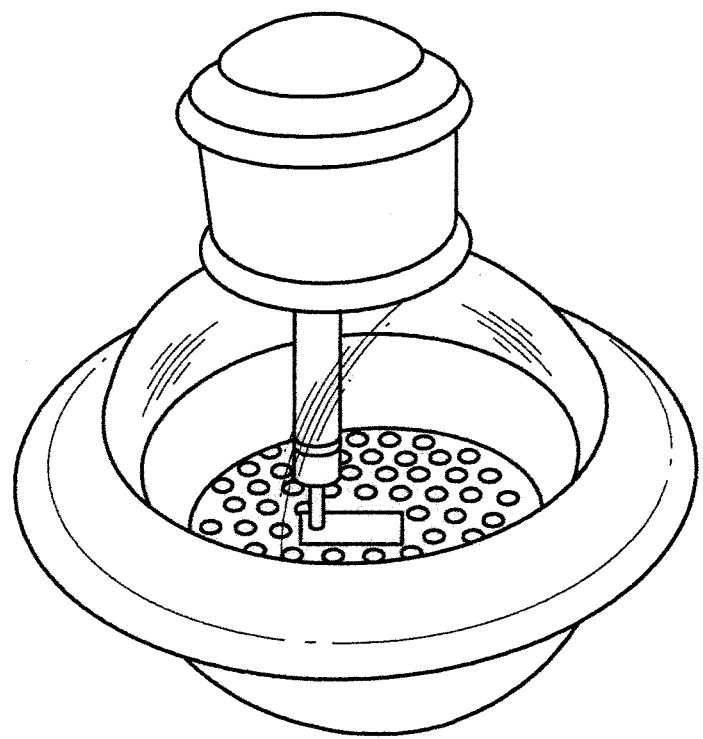
FIG. 52 is an image of flow testing with a syringe in the vacuum desiccator.
Figures 53A, 53B:
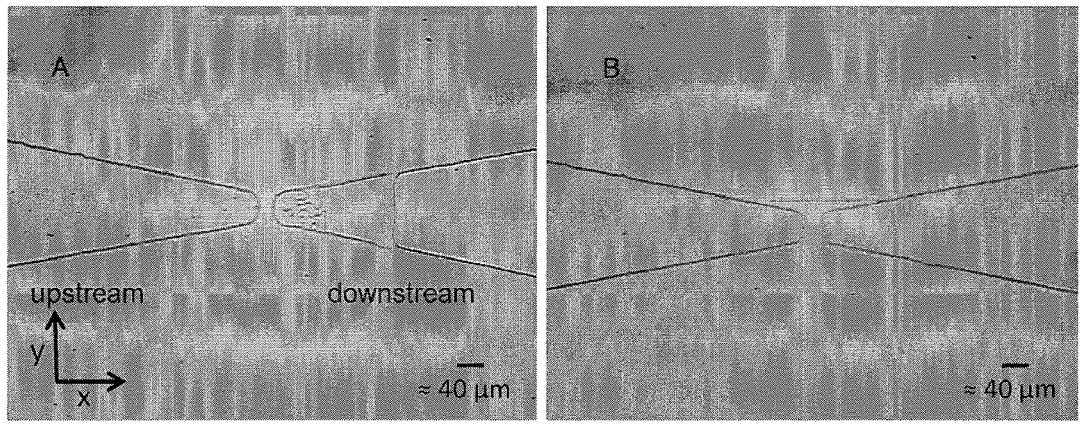
FIG. 53($a$) and FIG. 53($b$) are optical images of the DI water flow test after 4 hours (FIG. 53($a$)) and 8 hours (FIG. 53($b$)).

Flow Characteristics: Inside a Vacuum Desiccator: The best way to perform flow tests during this project was by using the vacuum desiccator, displayed in FIG. 52. The nanofluidic chip was connected to a syringe filled with DI water or some other solution. The top of the syringe was pressed against the lid of the desiccator, which created a constant pushing force on the solution. The outlet was left open to the vacuum, creating a pressure gradient throughout the channels resulting in fluid flow. The first device that was tested in the desiccator was from Process C. This chip had a nanochannel of 90 nm deep×900 nm wide×35 μm long±1 nm, and it was fabricated using a DNISP AFM probe. The Cr/Au microelectrodes were stripped off of the chip to ensure proper bonding. The focus of this flow test was only to see if fluid could be pumped through the nanochannel. The syringe was filled with 0.5 mL of water and the pump was turned on. After two hours, the entire upstream microchannel was filled with water. After two additional hours, water had been successfully pumped through the nanochannel and was starting to fill up the downstream microchannel, as shown in FIG. 53. The dark pink color represents a wetted channel, and the light pink color represents a dry channel. In FIG. 53A, some air pockets started to form in the downstream microchannel. After 8 hours, however, they were filled with water and the downstream microchannel continued to fill. This flow test proved that the nanochannel allowed water to be pumped through it. It was observed that it took around 4 hours for this to happen even though the nanochannel was relatively large, and this device did not have Cr/Au microelectrodes on it, so it did not serve as a viable device for DNA analysis. This method also did not prove if the anodic bonding was sufficient with electrodes in place. The next experiment needed to prove that the device did not leak in the nanochannel region during pumping. The easiest way to perform this task was by pumping a fluorescent fluid through the device while monitoring the flow with a fluorescent microscope.

Figure 54:
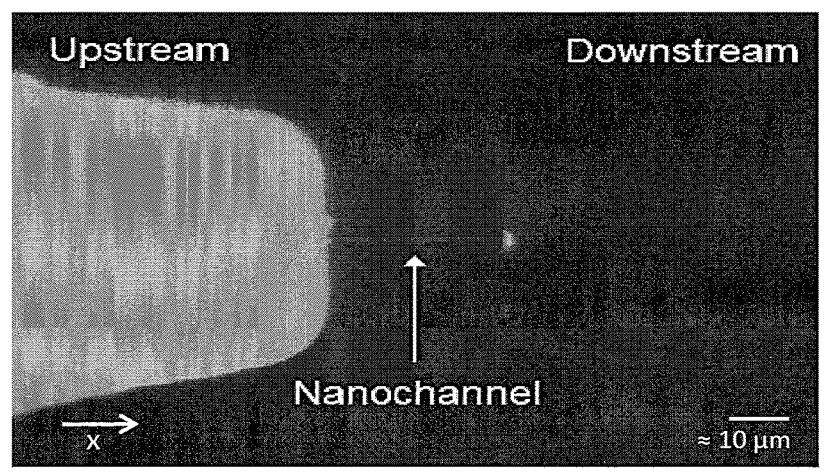
FIG. 54 illustrates the FITC flow test after 3 hours.
Figure 55:
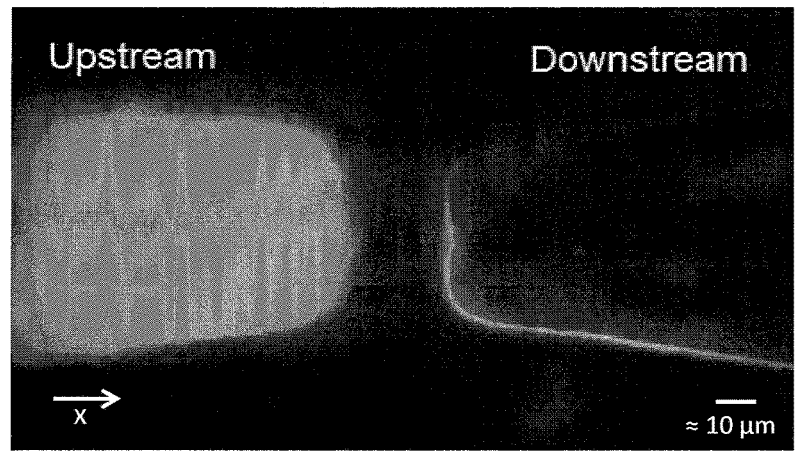
FIG. 55 illustrates the FITC flow test after 6 hours.

FITC Flow Tests: FITC flow tests were performed in order to analyze the patency of the nanochannels and, more importantly, the quality of the anodic bond. The nanochannel was fabricated by FIB milling and was 963 nm wide×105 nm deep±1 nm. Once the FITC was prepared, it was pumped through the nanofluidic device. After just three hours, as displayed in FIG. 54, the FITC solution had completely filled the upstream microchannel and the nanochannel. The downstream was starting to fill as well. FIG. 54 proved that the anodic bonding was successful because the nanochannel was well defined. This chip was fabricated by the design in Process C and had a Pt nanoelectrode that was approximately 750 nm wide×15 nm thick. Therefore, neither the Cr/Au microelectrodes (≈40 nm thick) nor the Pt nanoelectrode affected the anodic bond. After continuing to pump for an additional three hours, the downstream began to fill along the microchannel walls. The image in FIG. 55 showed that the FITC traveled along the sides of the microchannel walls first because they were more hydrophilic. FIG. 55 further demonstrated that there were no leaks in the device and that the anodic bonding was successful. Therefore, no further pumping was performed on this device. The patency of the nanochannel and proper anodic bonding were successfully demonstrated by these flow tests.

Figure 56:
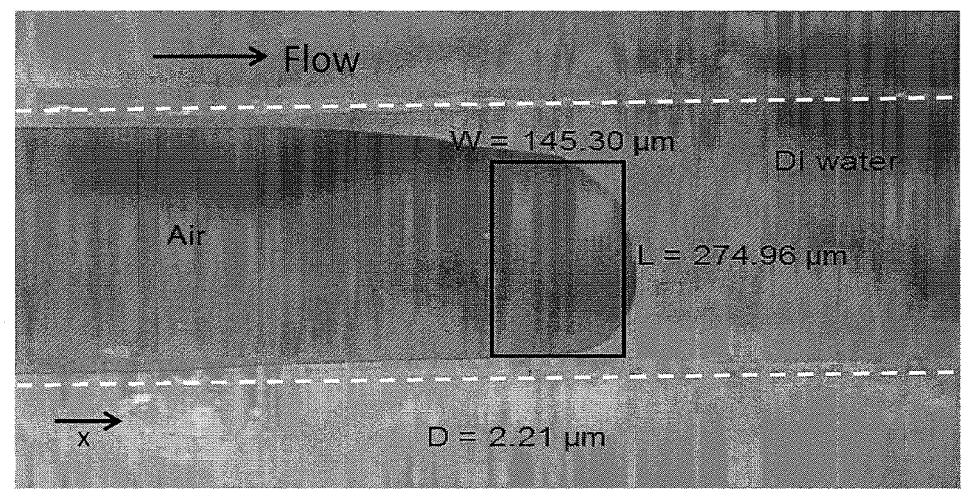
FIG. 56 illustrates downstream microchannel during flow test at time t=0.

Estimation of Nanochannel Flow Rate: A second method of pumping fluid through the nanochannel was demonstrated by connecting a syringe pump to the inlet and a vacuum pump to the outlet. The pressure gradient along the channel would force the fluid through the device. This method served to be a powerful, but damaging to the devices. DI water was pumped through the nanofluidic system and monitored in real time by using a microscope camera, and the displacement of the liquid/air interface in the downstream microchannel was used to approximate the nanochannel fluid velocity. The downstream microchannel at time t=0 is represented in FIG. 56. The black box defined the sample volume to be monitored. The flow direction was from the left to the right. However, the downstream microchannel was filled from right to left. This was because the water traveled from left to right along the edges of the microchannels. Once the water reached the end of the channel, it started to backfill in the opposite direction.

Figure 57:
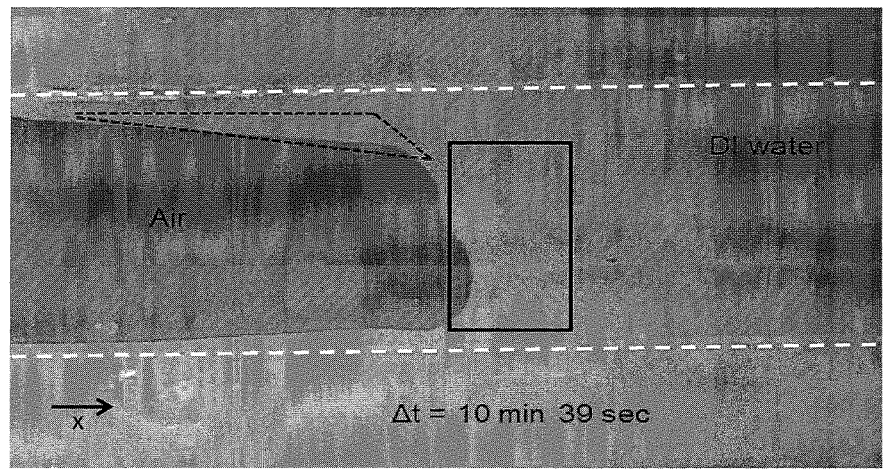
FIG. 57 illustrates downstream microchannel at the end of the flow test.

It was clear that at time t=0 the sample volume was partially filled with DI water. This experiment only served as a rough approximation of the nanochannel flow rate. The depth of the microchannels was about 2.21 μm, yielding a sample volume of ≈88,293.20 μm$^3$. The length and width of the sample area were determined by a MicroMeasure. The depth was measured by a dektak surface profilometer. After 10 minutes and 39 seconds, the flow was terminated because the sample area was filled with DI water. It was clear from FIG. 57 that the some of the sample area was still composed of air. The flow was still assumed to fill the entire sample area due to the increase in fluid in the area located by the dashed triangle. Since the fluid volume increased in this region and in the region just to the left of the sample area, the entire sample was assumed to be full at this point. Therefore, the volumetric flow rate was ≈138 μm$^3$/s. For this chip, the output nanochannel dimensions were 910 nm wide×107 nm deep×3 μm long±1 nm. Since FIG. 45 indicated that the nanochannels walls are sloped, a triangular cross-sectional area was used for the velocity estimation. As a result, the velocity of the fluid through the nanochannel was about 2,830 μm/s, or 2.83 mm/s. Other articles have claimed to have nanochannel fluid or particle velocity in the realm of 5 mm/s [57, 58]. For this nanofluidic device, at a velocity of 2.83 mm/s, the DI water was being pushed through the nanochannel in only 2.1 ms. Since the entire human genome is ≈2 m long, at this same velocity, the time to sequence would only be about 12 minutes [57]. Future investigations should be carried out in order to understand the nanochannel geometry and fluid velocity.

Electrical Measurements: For all subsequent experiments, the nanochannels were filled by submerging the entire chip in the desired fluid and placing it in the desiccator. The vacuum pump would displace any air in the device with the surrounding fluid. This method of wetting the device was much faster than the standard pumping methods described previously. Moreover, all of the remaining devices tested were fabricated by Process D because of the advantages of the shorter nanochannel. The nanochannels in these chips were fabricated by FIB milling and were ≈78% shorter in length on average than chips from Process C. As a result, the time to wet the device was decreased by 67%. Electrical measurements were performed to verify the behavior of the Pt nanoelectrodes.

Current-Voltage (I-V) Measurements: Fluids with significantly different electrical conductivities were pumped into the nanochannel. All fluid bulk conductivities were experimentally gathered by a VWR digital conductivity meter (±0.4% accuracy). Table 2 displays the bulk conductivities of the fluids used for I-V measurements.

TABLE 2

Bulk conductivities

| Fluid/Solution | Bulk σ (µS/cm) |
| --- | --- |
| Methanol | 0.1 |
| 20x MES | 71 |
| 20x PBS | 13.5k |
| 5x PBS | 49k |

Figure 58:
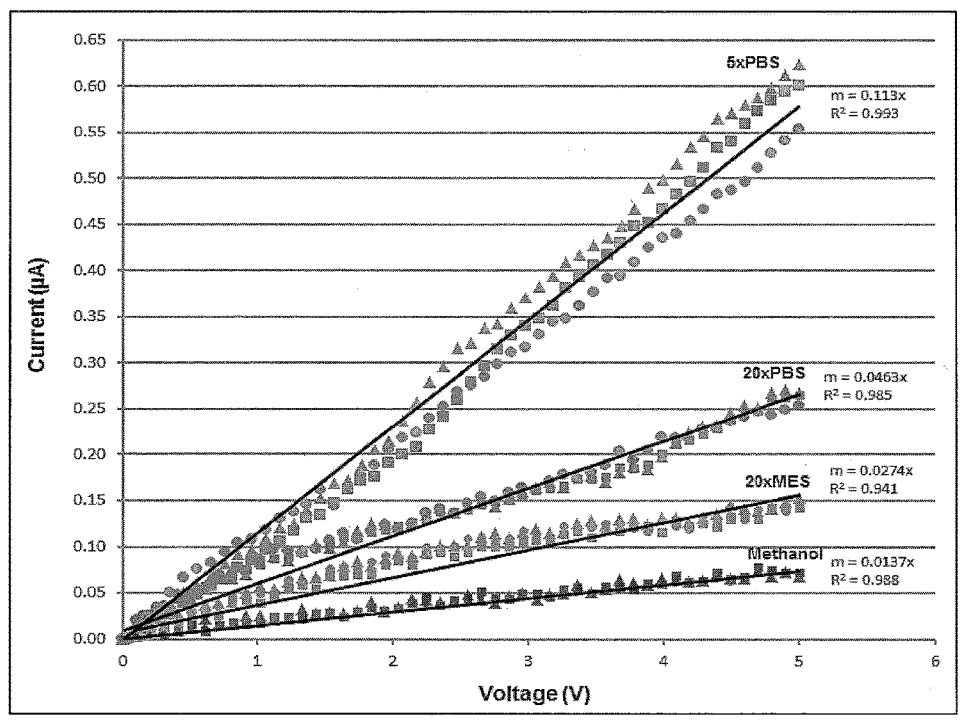
FIG. 58 illustrates I-V curves of various fluids in the nanochannel.
Figure 59:
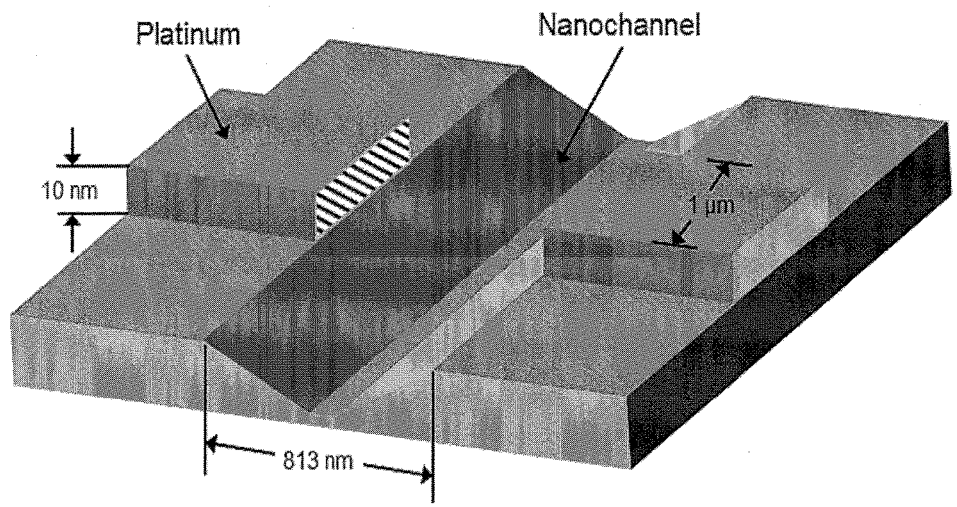
FIG. 59 is a schematic of the nanochannel and nanoelectrodes.
Figure 60:
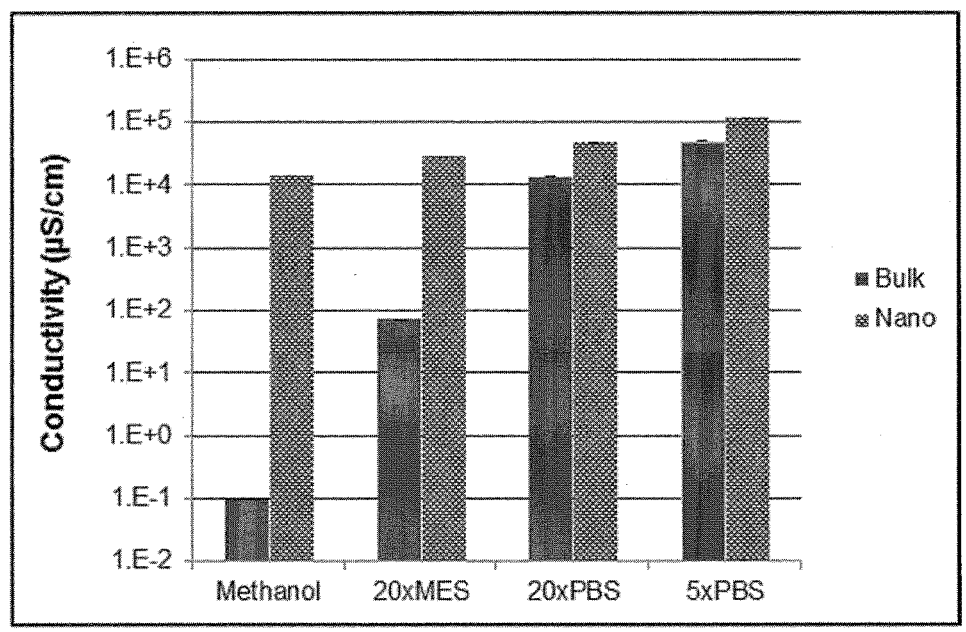
FIG. 60 is a graph comparing bulk versus nanoscale fluid conductivity.

The I-V measurements were used to determine if the nanoelectrodes behaved as an ohmic contact, a semiconducting material, or some other behavior. The I-V curves of four different fluids are displayed in FIG. 58. The fluids that were tested were methanol and DI water dilutions of 0.05 M morpholinoethanesulfonic acid (MES—$C_6H_{13}NO_4S$) and phosphate buffered saline (PBS—80 mM $Na_2HPO_4$, 1.5M NaCl, 20 mM $KH_2PO_4$, 30 mM KCl). For instance, a 5× dilution refers to 4 parts DI water and 1 part buffer. The voltage was applied by a Keithley 2401 Source Meter (1 µV-20 V and 10 pA-1 A precision, 0.012% accuracy, and 6 ½ digit resolution). The I-V plots were generated by sweeping a voltage from 0-5 V and recording 50 data points with LabTracer 2.9 software. The chip tested in FIG. 58 was 813 nm wide×42 nm deep±1 nm. The I-V relationship was primarily linear, meaning that the Pt nanoelectrode served as an ohmic contact. The I-V relationship was not perfectly linear in any trial because fluids typically do not act as solid state resistors. Also, the slopes increased with increasing bulk conductivity of the tested fluid. This verified that the I. nanoelectrodes could electrically identify various fluids based on their electrical properties. However, the conductivity of the fluids inside the nanochannel was larger than the bulk value. The bulk conductivity was gathered from the conductivity meter, and the fluid conductivity in the nanochannel was determined by the following, $$\sigma = \frac{Gl}{A} \quad \text{Equation 5}$$

where σ is the fluid conductivity, G is the conductance (slope of the I-V curve and inverse of the resistance), l is the distance between the Pt nanoelectrodes, and A is the cross-sectional area of the fluid between the Pt nanoelectrodes. The conductance was gathered from the measured resistance, the distance between the nanoelectrodes was ≈8.13× $10^{-5}$ cm, and the cross-sectional area was ≈1×$10^{-10}$ cm² as denoted by the black diagonal lines in FIG. 59 (thickness and width of Pt nanoelectrode was ≈10 nm×1000 nm respectively). The input thickness of the Pt nanoelectrode was 50 nm and the width was 700 nm. From previous results, it was determined this type of FIB deposition would yield output dimensions around 10-15 nm thick and 900-1000 nm wide. The slopes of the I-V curves from FIG. 58 were used in addition to Equation 5 to determine the nanoscale conductivities. Then, the bulk (measured) conductivity was compared to the nanoscale (measured and calculated) conductivity. FIG. 60 shows a bar graph displaying the difference between the bulk and nanoscale fluid conductivities of methanol, 20×MES, 20×PBS, and 5×PBS. The blue bars represent the bulk conductivity, and the upper red bars represent the nanoscale conductivity.

The more insulating fluids experienced a much larger difference between the nanoscale and bulk electrical conductivities. Methanol, the least conductive sample, experienced a 5 order of magnitude (OM) increase in conductivity from bulk to nanoscale. The most conductive sample, 5×PBS, only experienced a 0.5 OM increase in conductivity. Previous journal articles have indicated that the electrical conductivity of nanofluids can behave differently from that of the bulk value or calculated value [59, 60]. It was suspected that this occurrence was a result of tunneling effects due to the nanoscale environment or a result of current spreading through the Pt electrodes within the nanochannel. The main goal of this experiment was to determine if the nanoelectrodes could electrically isolate fluids with extremely different electrical conductivities. Even though the conductivity was found to be different at the nanoscale when compared to bulk, the device successfully differentiated each individual fluid. The next step was to translocate negatively charged nanobeads through the nanochannel and monitor the transverse current signal in real time.

Figure 61A:
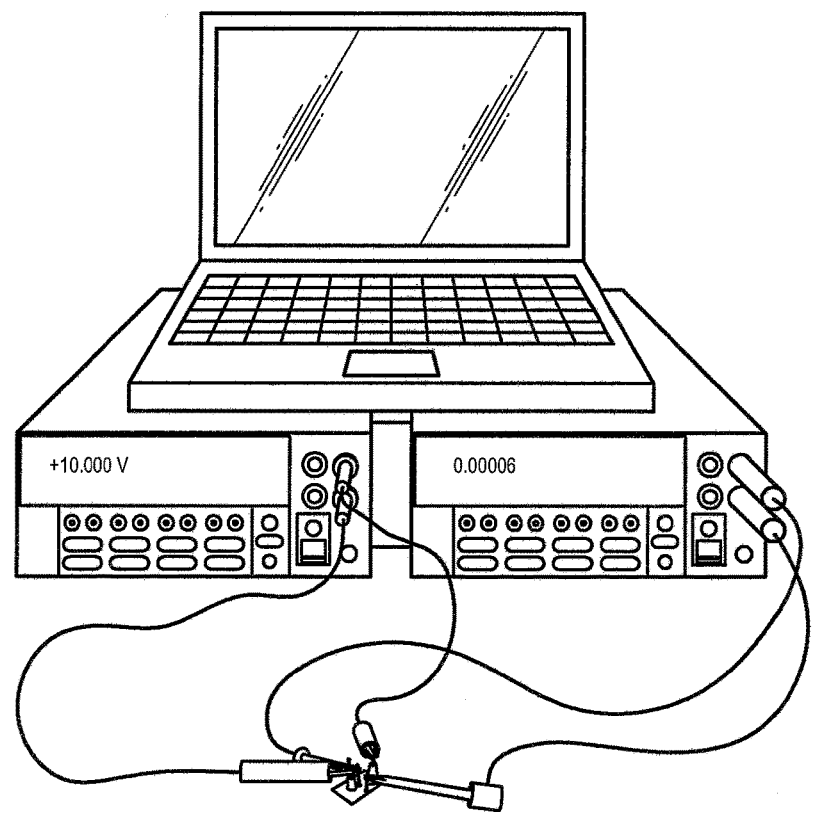
FIG. 61($a$) and FIG. 61($b$) illustrate an experimental set-up for nanobead translocation.
Figure 61B:
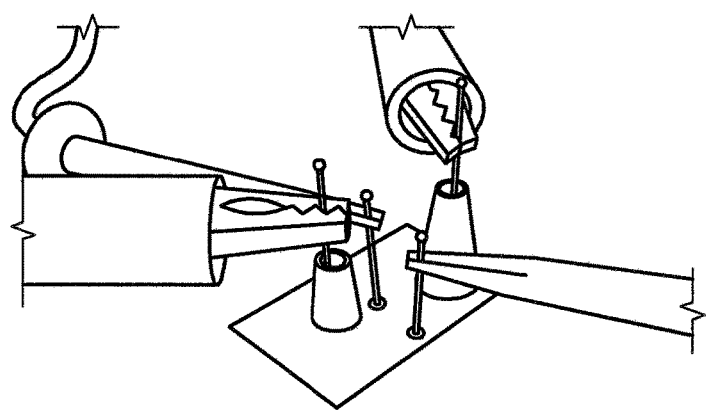
Figure 62:
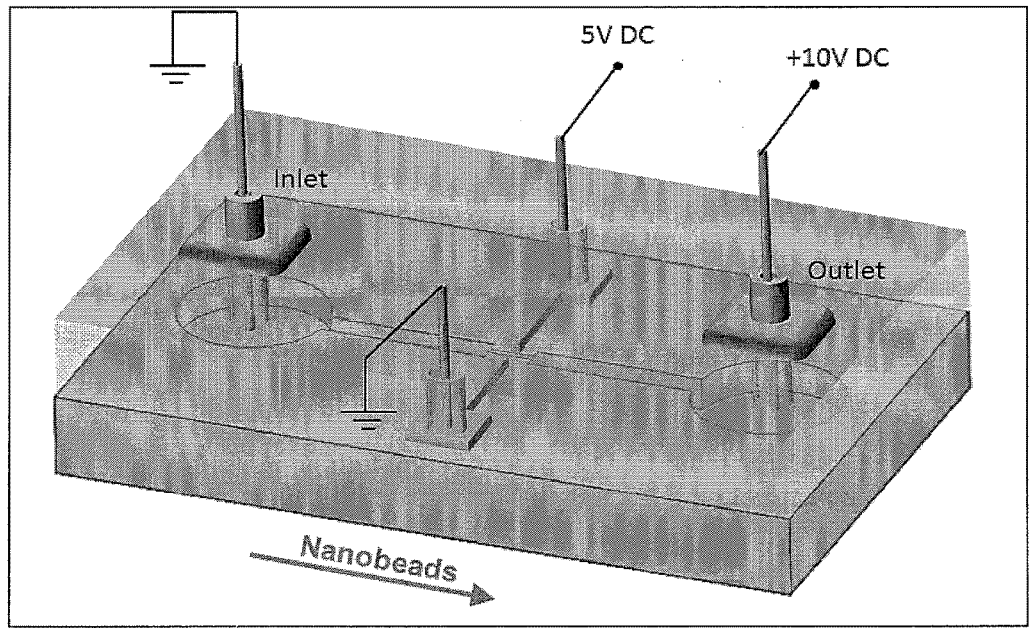
FIG. 62 is a schematic of an experimental set-up for nanobead translocation.

Nanobead Translocation: The final experiment was to translocate 20 nm diameter, negatively charged nanobeads (FluoSpheres® microspheres) through the nanochannel. FIG. 61 displays the experimental setup of this procedure. The current across the nanoelectrodes was recorded to determine if the nanobeads altered the signal in any way. The circuit connected to the nanofluidic device is displayed in FIG. 62. First, about 30 µL of nanobead solution was added to the inlet and pumped to fill the upstream microchannel. This was done by placing the chip in the vacuum desiccator and sealing the inlet once the nanobeads were introduced. It normally took between 3-6 hours for the nanobeads to reach the tip of the upstream microchannel. Then, while the inlet was still sealed, the chip was submerged in either DI water or 5×PBS to fill the downstream microchannel and the nanochannel. At this point, the upstream was filled around 70-95% with nanobeads and the nanochannel and downstream was filled with either DI water or PBS. Electrical continuity through the channels between the inlet and outlet was verified by a Keithley 2401 source meter. A second Keithley 2401 Source Meter was used to source 5 V across the electrodes and the 10 V along the length of the channels. The 10 V generated an electric field of ≈6.1 V/cm across the channels. This served as the driving force of the negatively charged nanobeads. The effective resistance's of the microchannels and nanochannel was 1.9 MΩ and 20.4 kΩ respectively. The source meter across the electrodes was connected to a PC and interfaced with LabTracer 2.9 to plot the output current signal.

Figure 63:
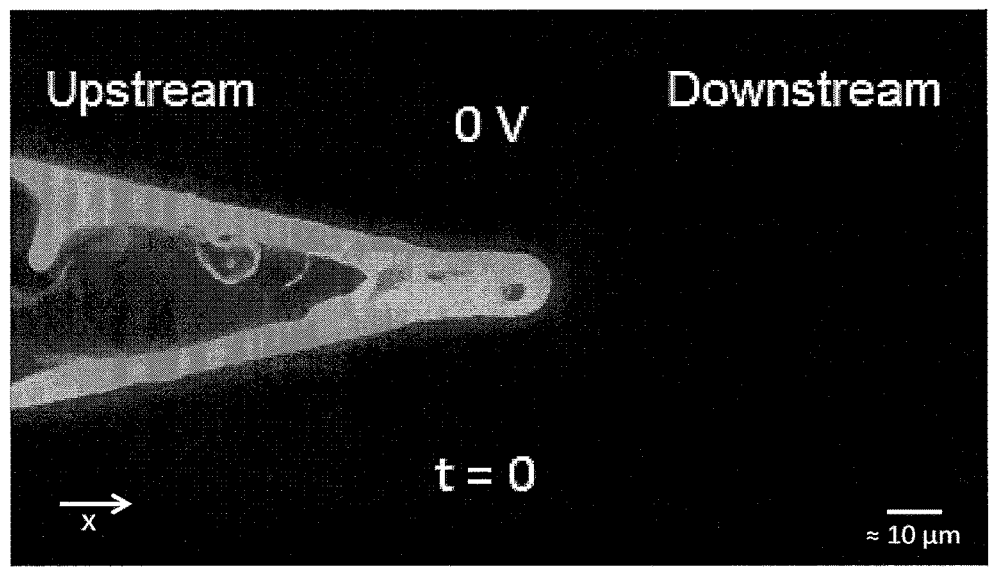
FIG. 63 illustrates an upstream microchannel partially filled with fluorescent nanobeads.
Figure 64:
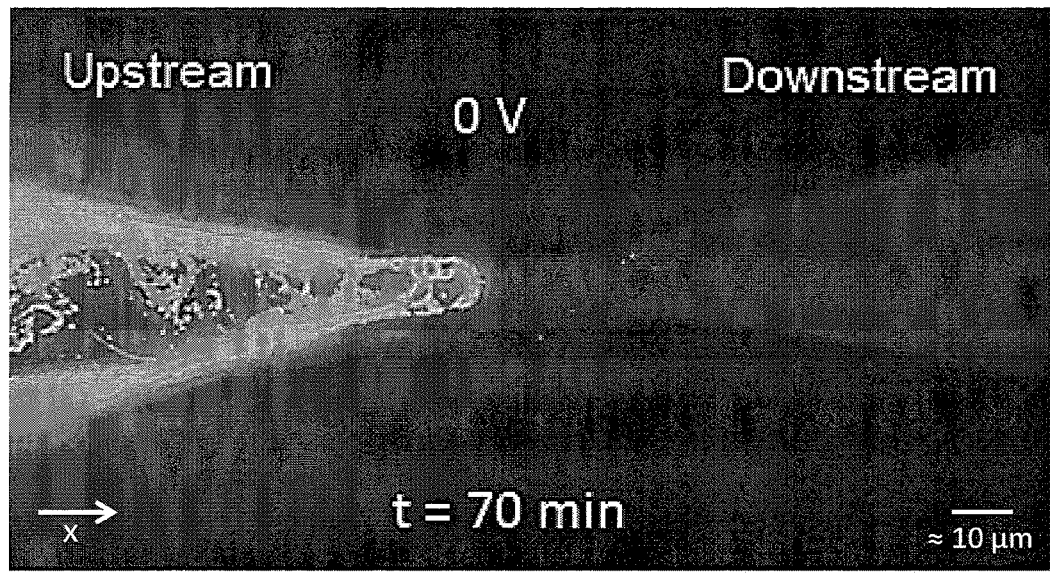
FIG. 64 illustrates nanobead translocation through the nanochannel and into the downstream microchannel.

Before the current across the Pt nanoelectrodes, known as the transverse current, was measured, it was essential to see if the device could translocate nanobeads through the nanochannel first. As shown in FIG. 63 (1 second exposure time), the nanobeads occupied the upstream microchannel while leaving the downstream filled with only 5×PBS. In this case, it took about 5 hours to pump the nanobeads into the upstream microchannel. Even though the entire upstream microchannel was not filled with nanobeads, it did not hinder their translocation through the nanochannel. The nanobeads only occupied about 80% of the upstream microchannel, as the rest of the channel was occupied by air bubbles. After 70 minutes of translocation, the device was inspected under the fluorescence microscope, and the result is displayed in FIG. 64. This image was captured at an exposure time of 5 seconds because the downstream microchannel was not illuminating as brightly in the picture as it was through the microscope lens. As a result, the upstream microchannel illuminated more brightly in FIG. 64 as opposed to FIG. 63. Nevertheless, it was clear that nanobeads had moved through the nanochannel and into the downstream microchannel.

Figure 65:
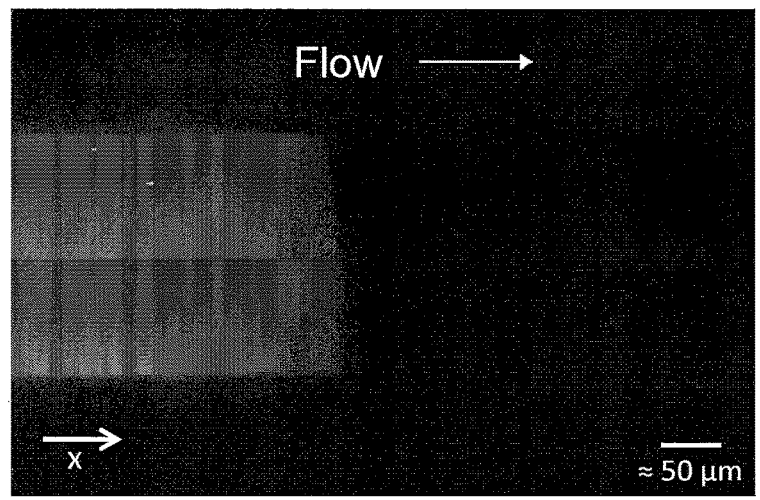
FIG. 65 illustrates the downstream microchannel where the nanobead flow ended.

It was interesting to note that the nanobeads filled the downstream microchannel uniformly. During the FITC flow tests, the fluid was highly attracted to the microchannel walls and filled the edges of the microchannels first. For this experiment, however, the channels were pre-filled with 5×PBS, and the nanobeads were able to fill the downstream microchannel in a uniform manner. Moreover, the upstream microchannel was filled in a non-uniform manner. This was because the fluid was pumped into the upstream microchannel without any pre-filled PBS present. The end of the nanobeads in the downstream microchannel is displayed in FIG. 65 (5 second exposure time). Now that fluid and nanobeads were successfully passed through the nanochannel without any leaking of the nanofluidic device, the output current across the electrodes was monitored.

Figure 66:
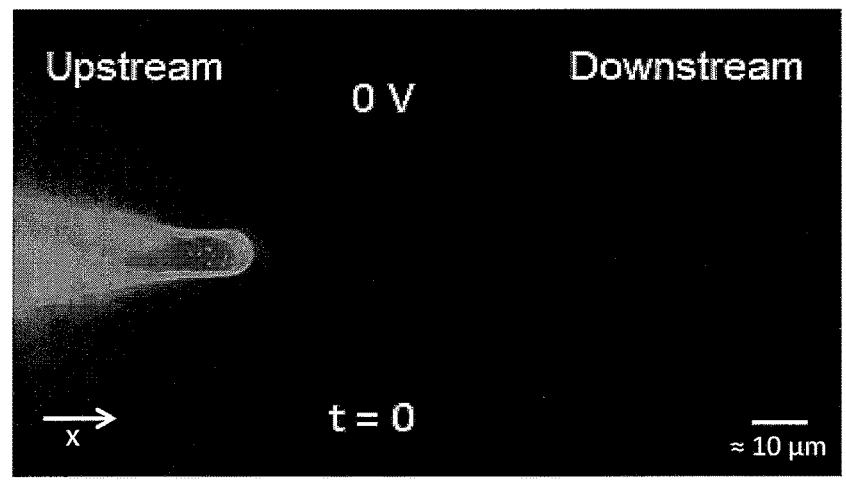
FIG. 66 is a fluorescent image before second nanobead translocation.
Figure 67:
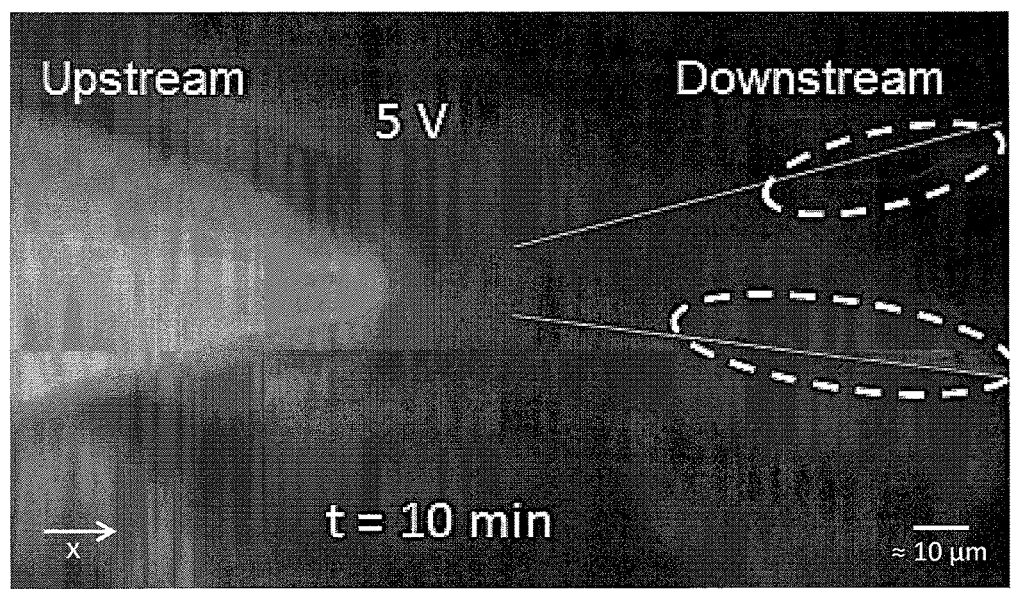
FIG. 67 is a fluorescent image of nanobead translocation where the white ovals represent nanobead clusters in the downstream microchannel.

Transverse Current Measurements: Another nanofluidic device was fabricated by Process D and prepared for nanobead translocation. FIG. 66 displays the upstream microchannel filled with fluorescent nanobeads. For this translocation experiment, the transverse current was measured during nanobead translocation through a nanochannel that was 950 nm wide×105 nm deep×7 µm long±1 nm. This experiment spanned a period of 10 minutes, and pockets of nanobeads were observed in the downstream microchannel as displayed in FIG. 67. By comparing FIGS. 67 and 66, it was evident that the downstream distribution of the translocated nanobeads was not always even. As shown in FIG. 67, in a short translocation event (10 minutes instead of 70 minutes), the nanobeads tended to accumulate along the sidewalls of the downstream microchannel. The solid lines in FIG. 67 indicate sections the downstream microchannel walls. The dashed ovals represent the areas where nanobeads were located in the downstream microchannel. There were a few similar clumps further downstream as well, but there were not any completely filled areas as demonstrated in FIG. 64.

The output current signal across the nanoelectrodes is displayed in FIG. 68. The 10 V power supply was powered on at 30 seconds and powered off at 130 s. It was powered on again at 200 s. This on and off cycle of the DC power allowed a baseline current to be established. The baseline current observed was approximately 5 nA. Around 250 s, the current jumped from 5 nA to around 35 nA. This was speculated to be the point when the nanobeads reached the nanoelectrodes in the nanochannel. The average current during the nanobead translocation period was about 22 nA, varying between 5 nA and 40 nA. At around the 300 s mark, the current dropped down to about 5 nA, which was close to the baseline current when no nanobeads were present in the nanochannel. This indicates that there were very few, if any nanobeads in the nanochannel at this time.

Previous research had been conducted to estimate the tunneling current effects of nanobeads in a nanochannel [61]. The tunneling current through charged nanobeads inside of a nanochannel can be estimated by the following equation, $$I = \frac{q^2 V^2}{4h\phi\lambda^2 d^2} r^2 \qquad \text{Equation 6}$$

where I is the tunneling current, q is the electron charge, V is the applied voltage, h is Plank's constant, $\Phi$ is the tunneling barrier height, $\lambda$ is an experimental parameter related to the location of the nanobead in the nanochannel ($0<\lambda<1$), d is the distance between the electrodes, and r is the average radius of the nanobeads. By using this equation for the nanofluidic system tested in FIG. 68, the tunneling current for one nanobead was estimated to be 28.7 nA. This value was in the same range as the average current value (250 s<t<600 s) from FIG. 68 of 22 nA. Therefore, it was plausible that the current spikes in FIG. 68 were due to quantum tunneling effects through the nanobeads in the nanochannel. The nanobeads were successfully translocated through the nanochannel, but the results were inconsistent. More nanobead translocation experiments need to be conducted to understand the translocation repeatability and the electrical behavior of the transverse current.

Conclusions: This research demonstrated the design and micro/nanofabrication methodologies required to fabricate a transparent nanofluidic system with embedded sensing electrodes. The evaporation of Cr/Au onto a Pyrex® glass 7740 wafer led to successful microchannel and microelectrode fabrication. Platinum sensing electrodes (≈25 nm-1000 nm wide) were then deposited using the FIB to bridge the Cr/Au gaps. The nanochannels were realized through both AFM nanolithography and FIB milling techniques to simultaneously cut through the electrodes in the normal direction and connect the microchannels via a nanochannel. A 100 nm thick layer of amorphous silicon was deposited on a separate Pyrex® glass 7740 substrate by PECVD and used to package the nanochannel chip through anodic bonding.

Nanochannel patency was verified by DI $H_2O$ and FITC flow tests coupled with optical and fluorescent microscopy respectively. The volumetric flow rate and nanochannel fluid velocity were estimated to be 138 µm³/s and 2,830 µm/s respectively through a 910 nm wide×107 nm deep×3 µm±1 nm long nanochannel. The behavior of the Pt nanoelectrodes was acquired through I-V curves. Finally, negatively charged nanobeads (20 nm diameter yellow-green Fluo-Spheres® microspheres) were translocated through the nanochannel by a 6.1 V/cm electric field, and their corresponding electrical signatures were measured by transverse platinum sensing electrodes.

Future Work: There are several steps that could be taken in the future in order to further improve the performance of the nanofluidic device:

(a) The nanochannel geometry needs to be verified. In this research, the FIB milled nanochannels seem to be triangular even though they are designed to be rectangular.

(b) The two or three electrode configuration could be fabricated and tested. This would allow the device to have multiple sensing locations. This would be beneficial during flow tests and nanochannel fluid velocity tests. The distance between each nanoelectrode would be known, and by timing how long it takes for fluid to flow from one contact to the other, the nanochannel fluid velocity could be calculated and compared to the results from this research.

(c) The 100 nm thick layer of a-Si deposited on Pyrex® glass for anodic bonding could likely be decreased by at least 50%. This would allow the device to be even more transparent than this work's devices. As a result, optical microscopy from both sides of the chip would be easier.

(d) The device could be capped off with a thick layer (≈1-5 mm) of PDMS as opposed to another Pyrex® glass chip with a-Si. The $O_2$ plasma cleaner could be used to permanently cap off the device with PDMS instead of using anodic bonding. This would keep the device from being exposed to high temperatures (350-400° C.) for long periods of time (30 minutes-2 hours). By avoiding these high temperatures, the Pt nanoelectrodes will likely stand a better chance of survival during bonding. Therefore, the size of the nanoelectrodes could possibly be reduced from around 500 nm-1 µm wide to <100 nm wide.

(e) The nanochannel dimensions should be fabricated by FIB-milling and made as small as possible. The nanochannel width and depth should be <50 nm each, with the goal being for single digit nanometer dimensions. This would increase the chance of single DNA strand isolation in the nanochannel.

(f) Different concentrations of nanobeads should be translocated through the nanochannel to observe the effect on the output current. The higher concentrations may generate an increase in the frequency and/or the amplitude of the current.

(g) Joule heating through the Pt nanoelectrodes during nanobead translocation needs to be investigated to determine if the Pt will behave as a wire or a fuse over time.

Impact of Research Results on U.S. and Global Society: There is a major impact on the U.S. and global society as a result of this research. A rapid, inexpensive (less than 2 hours and $1,000) method to sequence the entire human genome would completely revolutionize the medical industry. Medical professionals would be able to know all of the information that is genetically stored in each patient. This would allow doctors to better understand why some people are diagnosed with certain diseases and how they react to particular drugs. Moreover, future illnesses such as diabetes, cancer, Alzheimer's, etc. could be predicted and possibly avoided by human genome comparisons and studies. Advancements in this research area could completely change the way health care is administered today.

Impact of Research Results on the Environment: This research does not have any negative impacts of the environment. In fact, the nanofluidic device is extremely small and biocompatible, and it does not require large sample sized during testing. Therefore, there is not much waste associated with this method of DNA sequencing when compared to current methodologies that are present today.

REFERENCES

[1] C. Eijkel, "Nanofluidics: what is it and what can we expect from it?" *Microfluid Nanofluid*, vol. 1, pp. 249-267, 2005.
[2] http://microscopy.uark.edu/5314.php, URL accessed on Feb. 21, 2013.
[3] G. McVean, D. Altshuler, R. Abecasis, et al, "An intergrated map of genetic variation from 1092 human genomes," *Nature*, vol. 491, pp. 56-65, 2012.
[4] K. Patterson, "1000 Genomes: A World of Variation," *Journal of the American Heart Association*, vol. 108, pp. 534-536, 2011.
[5] NLM, "Quantum steps to better sequencing," *Nature Nanotechnology*, vol. 5, pp. 823-833, 2010.
[6] K. Wetterstand, "DNA Sequencing Costs: Data from the NHGRI Genome Sequencing Program (GSP)," *NHGRI*, 2013.
[7] C. Pareek, R. Smoczynski, A. Tretyn, "Sequencing technologies and genome sequencing," *Journal of Applied Genetics*, vol. 52, pp. 413-435, 2011.
[8] J. Schloss, "How to get genomes at one ten-thousandth of the cost," *Nature Biotechnology*, vol. 26, pp. 1113-1116, 2008.
[9] E. Chan, "Mutation Research/Fundamental and Molecular Mechanisms of Mutagenesis," *SciVerse*, vol. 573, pp. 13-40, 2004.
[10] V. Tabar-Cossa, D. Trivedi, M. Wiggin, et al, *Nanotechnology*, vol. 18, 2007.
[11] A. Storm, J. Chen, H. Zandbergen, "Translocation of double-strand DND through a silicon oxide nanopore," *The American Physical Society*, vol. 71, pp. 301-310, 2005.
[12] D. Fologea, J. Uplinger, B. Thomas, et al, "Slowing DNA translocation in a solid-state nanopore," *Nano Letters*, vol. 5, pp. 1734-1737, 2005.
[13] A. Ivanov, E. Instuli, C. Mcgilvery, et al, "DNA Tunneling Detector Embedded in a Nanopore," *Nano Letters*, vol. 11, pp. 279-285, 2011.
[14] X. L. H. Peng, "Reverse DNA Translocation Through a Solid-state Nanopore by Magnetic Tweezers," *Nanotechnology*, vol. 20, 2009.
[15] U. Keyser, B. Koeleman, S. Dorp, et al, "Direct force measurements on DNA in a solid-state nanopore," *Nature Physics*, vol. 2, pp. 473-477, 2006.
[16] M. Bates, M. Burns, A. Meller, "Dynamics of DNA molecules in a membrane channel probed by active control techniques," *Biophysical Journal*, vol. 84, pp. 2366-2372, 2003.
[17] J. G. M. Gershow, "Recapturing and trapping single molecules with a solid-state nanopore," *Nature Nanotechnology*, vol. 2, pp. 775-779, 2007.
[18] S. Min, W. Kim, Y. Cho, et al, "Fast DNA sequencing with a graphene-based nanochannel device," *Nanture Nanotechnology*, vol. 6, pp. 162-165, 2011.
[19] D. Hansford, "Microfabricated nanochannels: new tools for molecular motion control," *ISSN*, vol. 3, pp. 95-100, 2009.
[20] M. B. Stern, M. W. Geis and J. E. Curtin, "Nanochannel fabrication for chemical sensors," *Journal of Vacuum Science & Technology B: Microelectronics and Nanometer Structures*, vol. 15, pp. 2887-2891, 1997.
[21] H. Cao, Z. Yu, J. Wang, J. O. Tegenfeldt, R. H. Austin, E. Chen, Wei Wu and S. Y. Chou, "Fabrication of 10 nm enclosed nanofluidic channels," *Applied Physics Letters*, vol. 81, pp. 174-176, 2002.
[22] J. Haneveld, "Wet anisotropic ething for fluidic 1D nanochannels," *Journal of Micromechanics and Microengineering*, vol. 13, pp. 62-66, 2003.
[23] F. Watt, "Proton Beam Writing," *Materials Today*, vol. 10, 2007.
[24] M. Malloy, "Consortium tests the viability of nanoimprint lithography," *SPIE*, vol. 10, pp. 120-129, 2009.
[25] H. Hoang, I. Segers-Nolten, J. Berenshot, et al, "Fabrication and interfacing of nanochannel devices for single-molecule studies," *Journal of Micromechanics and Microengineering*, vol. 19, pp. 605-617, 2009.
[26] J. Rosa, M. Wendel, H. Lorenz, et al, "Direct patterning of surface quantum wells with an atomic force microscope," *Applied Physics Letters*, vol. 73, pp. 2684-2686, 1998.

[27] J. Regul, U. Keyser, M. Paesler, et al, "Fabrication of quantum point contacts by engraving GaAs/AlGaAs heterostructures with a diamond tip," *Applied Physics Letters*, vol. 81, pp. 2023-2025, 2002.

[28] X. Xie, "Nanoscale materials patterning and engineering by atomic force microscopy and nanolithography," *Materials Science and Engineering*, vol. 54, pp. 1-48, 2006.

[29] 0. Hibbert, T. Busch, S. Tung, "A Pyrex glass Nanochannel Device Fabricated by AFM Nanolithography," *IEEE NEMS*, 2011.

[30] J. Orloff, L. Swanson, M. Utlaut, "Fundamental limits to imaging resolution for focused ion beams," *Journal of Vacuum Science & Technology*, vol. 14, pp. 58-63, 1996.

[31] http://www.eoearch.org/article/Gallium, URL accessed on Feb. 20, 2013.

[32] R. P. S. Reyntjens, "A review of focues ion beam applications in microsystem technology," *Journal of Micromechanics and Microengineering*, vol. 11, pp. 287-300, 2001.

[33] L. G. B. Kempshall, "Comparative evaluations of protective coatings and focused ion beam chemical vapor deposition processes," *Journal of Vacuum Science & Technology*, vol. 20, pp. 286-290, 2002.

[34] J. Lum, R. Wang, K. Lassiter, et al, "Rapid detection of avian influenza H5N1 virus using impedance<br />measurement of immuno-reaction coupled with RBC amplification," *Biosensors and Bioelectronics*, vol. 38, pp. 67-73, 2012.

[35] M. V. M. Zwolak, "Electronic Signature of DNA Nucleotides via Transverse Transport," *Nano Letters*, vol. 5, pp. 421-424, 2005.

[36] S. Huang, J. He, S. Chang, et al, "Identifying single bases in a DNA oligomer with electron tunnelling," *Nanture Nanotechnology*, vol. 10, pp. 868-873, 2010.

[37] Y. Shamoo, "Single-stranded DNA-binding proteins," John Wiley & Sons Ltd, vol. 10, pp. 1038-1045, 2002.

[38] O. Hibbert, "Design and Fabrication of Nanofluidic systems for biomolecule characterizations," 2011.

[39] C. Iliescu, K. Tan, F. Tay, et al, "Deep wet and dry etching of Pyrex glass: a review," *ICMAT*, 2005.

[40] B. M. A. Bahadorimehr, "Fabrication of Glass-based Microfluidic Devices with Photoresist as Mask," *Electronics & Electrical Engineering*, vol. 116, pp. 45-49, 2011.

[41] http://www.latoscientific.com/borosilicate, URL accessed on Feb. 23, 2013.

[42] C. Iliescu, F. Tay, J. Miao, et al, "Characterization of masking layers for deep wet etching of glass in an improved HF/HCl solution," *Surface & Coating Technology*, vol. 198, pp. 314-318, 2005.

[43] C. H. W. Shih, "Collapse of microchannels during anodic bonding: theory and experiments," *American Institute of Physics*, vol. 10, pp. 448-489, 2004.

[44] C. H. N. Li, "Patterning Functional Proteins with High Selectivity for Biosensor Applications," *The Association for Laboratory Automation*, vol. 10, pp. 1016, 2008.

[45] C. Lin, G. Lee, Y. Lin, et al, "A fast prototyping process for fabrication of microfluidic systems on soda-lime glass," *IOP Science*, vol. 11, pp. 726-732, 2001.

[46] E. Francis, H. Tay, C. Iliescue, et al, "Defect-free wet etching through Pyrex glass using Cr/Au mask," *Impact Factor*, vol. 12, pp. 935-939, 2005.

[47] W. Chen, G. Li, Q. Jin, et al, "A Rapid and Low-Cost Procedure for Fabrication of Glass Microfluidic Devices," *Journal of Microelectromechanical Systems*, vol. 16, pp. 1193-1200, 2007.

[48] http://clean room.ien.gatech.edu/media/resources/equipment/instructions/Dektak.pdf, URL accessed on Apr. 5, 2013.

[49] http://www.nanotech.ucsb.edu/index.php?option=com_dektak-profilometer, URL accessed on Apr. 5, 2013.

[50] Y. Mourzina, A. Steffen, A. Offenhausser, "The evaporated metal masks for chemical glass etching for BioMEMS," *Microsystem Technologies*, vol. 11, pp. 135-140, 2008.

[51] C. Iliescu, B. Chen, J. Miao, "On the wet etching of Pyrex Glass," *Sensors and Actuators*, vol. 143, pp. 154-161, 2008.

[52] T. Maleki, S. Mohammadi, B. Ziaie, "A nanofluidic channel with embedded transverse nanoelectrodes," Birck and NCN Publications, vol. 20, 2009.

[53] K. Takimoto, A. Fukuta, Y. Yamamoto, et al, "Linear thermal expansion coefficients of amorphous and microcrystalline silicon films," *Journal of Non-Crystalline Solids*, vol. 299, pp. 314-317, 2002.

[54] www.makeitfrom.com/material-data/?for=soda-lime-glass, URL accessed on Feb. 23, 2013.

[55] www.engineeringtoolbox.com/linear-expansion-coefficients-d_95.html, URL accessed on Feb. 24, 2013.

[56] P. U. E. Noga, "Fluorescein: A Rapid, Sensitive, Nonlethal Method for Detecting Skin Ulceration in Fish," *Vet Pathology*, vol. 39, pp. 726-731, 2002.

[57] E. A. S. Parker, *McGraw Hill Encyclopedia of Science and Technology*. New York: McGraw Hill, 1997.

[58] E. Tamaki, A. Hibara, H. Kim, et al, "Pressure-driven flow control system for nanofluidic chemical process," *Journal of Chromatography*, vol. 1137, pp. 256-262, 2006.

[59] S. White, K. Shih, K. Pipe, "Investigation of the electrical conductivity of propylene glycol-based ZnO nanofluids," *Nanoscale Research Letters*, vol. 6, pp. 346-351, 2011.

[60] S. Chang, S. Huang, Jin He, et al, "Electronic Signautres of all Four DNA Nucleosides in a Tunneling Gap," *Nano Letters*, vol. 10, pp. 1070-1075, 2010.

[61] Z. Wang, "Research on the MEMS and AFM Based Fabrication Method of Nanofluidic Channel Systems," *Graduate School of Chinese Academy of Sciences PhD Dissertation*, 2011.

Insofar as the description above and the accompanying drawings disclose any additional subject matter that is not within the scope of the single claim below, the inventions are not dedicated to the public and the right to file one or more applications to claim such additional inventions is reserved.

The present invention has been described with reference to certain preferred and alternative embodiments that are intended to be exemplary only and not limiting to the full scope of the present invention.

What is claimed is:

1. A method of fabricating a nanochannel system comprising the steps of:
   (a) micropatterning a substrate to form at least one electrode;
   (b) micropatterning said substrate to form a first microchannel portion and a second microchannel portion;
   (c) machining a nanochannel between said first microchannel portion and said second microchannel portion; and
   (d) bonding a cover chip to said substrate.

2. The method of claim 1, wherein said substrate is a silicon chip.

3. The method of claim 1, wherein said at least one electrode is a microelectrode.

4. The method of claim 1, wherein said at least one electrode is a nanoelectrode.

5. The method of claim 1, wherein said substrate comprises a silicon oxide layer.

6. The method of claim 1, wherein said step of machining causes said at least one electrode to be dissected into at least two microelectrodes.

7. The method of claim 1, wherein said step of machining comprises the step of using atomic force microscopy nanolithography.

8. The method of claim 1, wherein said step of machining is performed by a cutting tool, wherein said cutting tool comprises a diamond probe tip with a large spring constant and a nanoscale tip radius, wherein said diamond probe tip is mounted on a cantilever.

9. The method of claim 1, wherein said cover chip is a glass cover chip.

10. The method of claim 1, wherein said bonding is anodic bonding.

11. The method of claim 1, wherein said at least one electrode comprises five electrodes.

12. The method of claim 1, wherein said first microchannel portion is an inlet to said nanochannel and said second microchannel portion is an outlet from said nanochannel.

13. The method of claim 12, wherein said inlet comprises an inlet reservoir and said outlet comprises an outlet reservoir.

14. The method of claim 1, wherein said step of bonding a cover chip to said substrate comprises the steps of:
 (a) placing said substrate on a hot plate;
 (b) linking said substrate to an anode of a current supply;
 (c) placing said cover chip on top of said substrate;
 (d) linking said cover chip to a cathode of said current supply; and
 (e) providing a temperature of said hot plate and a voltage of said current supply sufficient to cause bonding between said substrate and said cover chip.

15. A method of fabricating a nanochannel system comprising the steps of:
 (a) micropatterning a first glass substrate to form a first microelectrode and a second microelectrode;
 (b) micropatterning said first glass substrate to form a first microchannel portion and a second microchannel portion;
 (c) depositing a nanoelectrode on said glass substrate between said first microelectrode and said second microelectrode;
 (d) machining a nanochannel between said first microchannel portion and said second microchannel portion;
 (e) bonding a second glass substrate to said first glass substrate.

16. The method of claim 15, wherein said step of micropatterning said first glass substrate to form a first microchannel portion and a second microchannel portion comprises the step of using photolithography and wet etching.

17. The method of claim 15, wherein said step of depositing a nanoelectrode on said first glass substrate comprises the step of using focused ion beam.

18. The method of claim 15, wherein said step of machining a nanochannel between said first microchannel portion and said second microchannel portion comprises the step of using atomic force microscopy nanolithography and focused ion beam.

19. The method of claim 15, wherein said bonding is anodic bonding.

20. The method of claim 15, wherein said second glass substrate comprises amorphous silicon.

\* \* \* \* \*